(12) United States Patent
Mai

(10) Patent No.: US 7,045,292 B2
(45) Date of Patent: May 16, 2006

(54) METHOD AND MARKER FOR IDENTIFICATION OF PRE-MALIGNANCY AND MALIGNANCY AND THERAPEUTIC INTERVENTION

(75) Inventor: Sabine Mai, Winnipeg (CA)

(73) Assignees: University of Manitoba, Winnipeg (CA); Cancercare Manitoba, Winnipeg (CA)

( * ) Notice: Subject to any disclaimer, the term of this patent is extended or adjusted under 35 U.S.C. 154(b) by 0 days.

(21) Appl. No.: 10/181,583

(22) PCT Filed: Jan. 22, 2001

(86) PCT No.: PCT/US01/02085

§ 371 (c)(1),
(2), (4) Date: Oct. 14, 2002

(87) PCT Pub. No.: WO01/53536

PCT Pub. Date: Jul. 26, 2001

(65) Prior Publication Data

US 2003/0211491 A1 Nov. 13, 2003

Related U.S. Application Data

(63) Continuation-in-part of application No. 09/489,288, filed on Jan. 21, 2000, now abandoned, which is a continuation-in-part of application No. 09/276,281, filed on Mar. 25, 1999, now abandoned.

(60) Provisional application No. 60/079,336, filed on Mar. 25, 1998.

(51) Int. Cl.
*C12Q 1/68* (2006.01)
*C07H 21/02* (2006.01)
*C07H 21/04* (2006.01)

(52) U.S. Cl. .................. 435/6; 536/23.5; 536/24.31
(58) Field of Classification Search ................ 435/6; 536/23.1, 23.5, 24.31

See application file for complete search history.

(56) References Cited

FOREIGN PATENT DOCUMENTS

EP 0 955 383 A 11/1999

OTHER PUBLICATIONS

Von Hoff et al. Proceedings of the National Academy of Sciences. 1992. 89: 8165-8169.*
Goker et al. Blood. Jul. 15, 1995. 86: 677-684.*
Mai et al. Oncogene. 1996. 12: 277-288.*
Riou et al. The Lancet. 1987. 2: 761-763.*
Riou et al. Bull. Cancer (1990) 77: 341-347.*
Taylor et al. Current Topics in Microbiology and Immunology. 1997. 224: 201-207.*
Mai et al. Blood. Nov. 1997. 90(10): 218B, abstract 3715.*
Werner et al. American Journal of Pathology. Aug. 1997. 151: 335-342.*
Riva, et al., Satellite DNA sequences flank amplified DHFR domains in marker chromosomes of mouse fibrosarcoma cells. *Genetica*, , vol. 94, No. 1, pp. 9-16 (1994).
Tlsty T D, Normal Diploid Human and Rodent Cells Lacks a Detectable Frequency of Gene Amplification, *Proceedings of the National Academy of Sciences of the United States*, vol. 87, No. 8, 1990, pp. 3132-3136 (1990).
Lucke-Huhle, C. Permissivity for methotrexate-induced DHFR gene amplification correlates with the metastatic potential of rat adenocarcinoma cells, Carcinogenesis, 1994, vol. 15, pp. 695-700.
Mai, et al., Chromosomal and extrachromosomal instability of the cyclin D2 gene is induced by myc overexpression, Neoplasia, 1999, vol. 1, pp. 241-252.

* cited by examiner

*Primary Examiner*—Carla J. Myers
(74) *Attorney, Agent, or Firm*—Kohn & Associates, PLLC; Kenneth I. Kohn

(57) ABSTRACT

There is provided a method for identifying pre-malignancy, malignancy, and degree of pre-malignancy and malignancy of a cell by detecting extrachromosomal and intrachromosomal gene amplification. Also provided is a marker for the identification of pre-malignancy, malignancy, and degree of pre-malignancy and malignancy of a cell containing extrachromosomal and intrachromosomal gene amplification of a gene. A diagnostic tool for the diagnosis and prognosis or cervical cancer containing extrachromosomal and intrachromosomal gene amplification of a gene.

2 Claims, 27 Drawing Sheets

Model of cyclin D2 gene amplification in CLL.
insert: replicative cycle of extrachromosomal elements (Ecs)

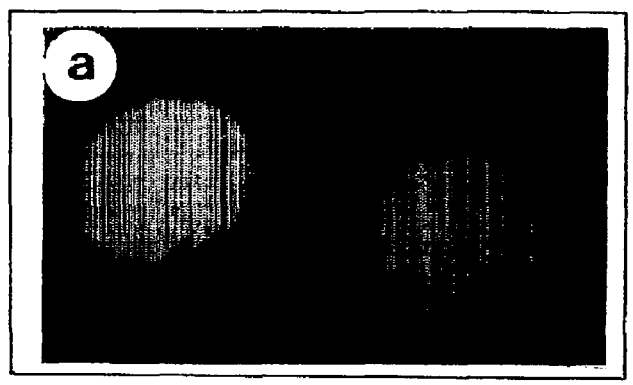
Fig-19A
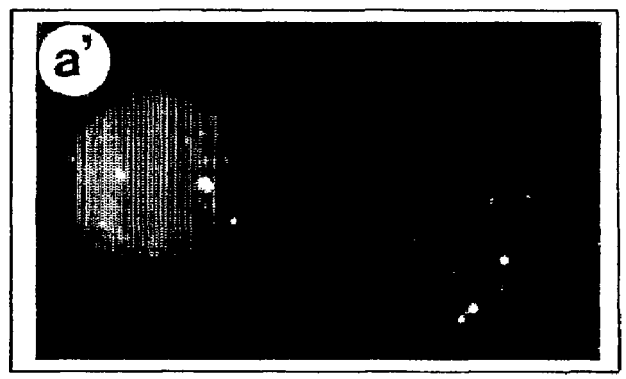
Fig-19A'
Fig-19A"

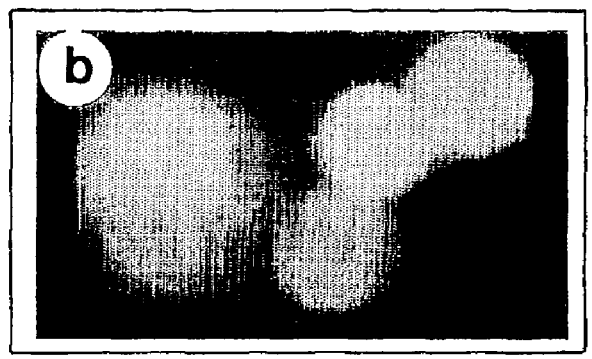
Fig-19B
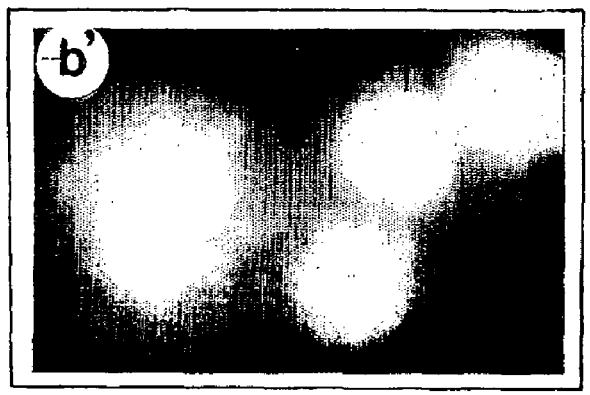
Fig-19B'
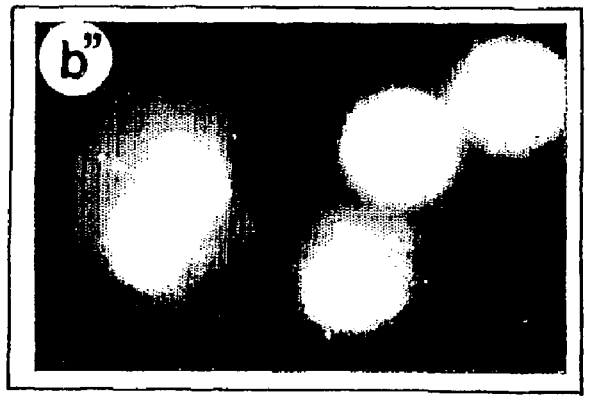
Fig-19"

METHOD AND MARKER FOR IDENTIFICATION OF PRE-MALIGNANCY AND MALIGNANCY AND THERAPEUTIC INTERVENTION

CROSS REFERENCE TO RELATED APPLICATIONS

This patent application is a National Phase Concerning a Filing Under 35 U.S.C 371, claiming the benefit of priority of PCT/US01/02085, filed Jan. 22, 2001, which is a Continuation-In-Part of U.S. Ser. No. 09/489,288, filed Jan. 21, 2000 now abandoned, which is a Continuation-In-Part of U.S. Ser. No. 09/276,281, filed Mar. 25, 1999 now abandoned, which claims the benefit of priority of United States Provisional Application Ser. No. 60/079,336, filed Mar. 25, 1998, all of which are incorporated herein by reference.

BACKGROUND OF THE INVENTION

1. Technical Field

The present invention relates to methods and markers for identification of pre-malignancy and malignancy states utilizing extrachromosomal and intrachromosomal gene amplification. Further the present invention relates to the identification of specific genes which undergo extrachromosomal gene amplification and therapeutic interventions relating to their utility as therapeutic targets.

2. Background Art

The diagnosis of malignant conditions is approached from multiple directions as for example tissue biopsies, serum levels of specific markers (PSA for prostate as an example), mammography and the like. However, most of these methods do not identify pre-malignant cells where early diagnosis can significantly increase treatment potential. Further the identification of a malignant condition does not necessarily identify an underlying genetic abnormality which can be corrected utilizing gene therapy or suggest other points of therapeutic intervention.

Chronic lymphocytic leukemia (CLL), is the commonest leukemia, making up 30% of all cases (O'Brien, et al. 1995), However, the cause of this disease is unknown. The leukemia primarily effects elderly males and is characterized by the accumulation of morphologically mature-appearing B1-lymphocytes in peripheral blood, marrow, spleen and lymph nodes (O'Brien, et al., 1995). Prognosis in CLL is approximately assessed by Rai staging (Table I) and patient survival varies from 2 years (Rai III and IV) to >10 years (Rai 0) (Rai, et al., 1975). However, with each stage there is considerable variation in survival and patients can be further stratified according to the lymphocyte doubling time (Montserrat, et al., 1986). Patients with a short lymphocyte doubling time (<12 months) have a poorer survival rate than those with a longer doubling time (Montserrat, et al., 1986). At the present time, this disease is incurable but remissions can be obtained with alkylating agents, e.g., chlorambucil, or nucleoside analogs, e.g., fludarabine, but relapse and the eventual development of drug resistance is usually observed (O'Brien, et al., 1995).

The normal cellular counterpart of the CLL cell is in the mantle zone of the lymphoid follicle, and, like CLL cells, these lymphocytes are CD5+ B cells and have high levels of bcl-2 (Schena, et al., 1992). It is presumed that a small fraction of CLL cells are proliferating stem cells, possibly located in the lymphoid tissue or marrow, but the majority of cells are non-proliferating and accumulate most likely through defects in apoptosis.

The term genomic instability summarizes a variety of genomic alterations which include the loss or gain of chromosomes as well as genetic changes at the level of single genes, such as rearrangements, translocations, amplifications, deletions and point mutations, and has been considered to be a major driving force of multistep carcinogenesis (Nowell, 1976; Pienta et al., 1989; Temin, 1998; Solomon et al., 1991). Genomic integrity is maintained by checkpoint mechanisms; when cells suffer damage imposed by exposure to genotoxic drugs or microtubule toxins, the cell cycle is halted until the damage is repaired or apoptosis is initiated (for reviews, see Hartwell, 1992; Weinert and Lydall, 1993; Hartwell and Kastan, 1994).

Gene amplification represents one form of genomic instability in mammalian cells, although it can also occur as part of a normal developmental program in insects, amphibia, and lower organisms (Santelli, et al., 1991; Delikadis, et. al., 1989; Start, et. al., 1984). With one published exception (Prody, et al., 1989), gene amplification has not been observed in normal diploid cells (Lucke-Huhle, et al., 1989; Wright, et al., 1990; Tlsty, et al., 1990) and its presence indicates that these cells are genomically unstable, immortalized, transformed and/or tumorigenic. In mammalian cells lines and tumors, gene amplification has been described after drug selection (Stark, et al., 1993; Huang, et al., 1994; Huang, et al., 1994; Shah, et al., 1986), DNA damage (Lucke-Huhle, et al., 1989; Lucke-Huhle, et al., 1990; Yalkinoglu, et al., 1991) and as a result of c-Myc overexpression (Mai, et al., 1994; Denis, et al., 1991). Spontaneous gene amplification has also been reported (Johnston, et al., 1983). Gene amplification can occur in the presence of wildtype p53, but is facilitated by its absence (Yin, et al., 1992; Livingstone, et al., 1992); thus, gene amplification can involve both p53-dependent and -independent pathways (Van Der Bliek, et al., 1986; Zhou, et al., 1996). Gene amplifications often involves oncogenes, and more than 90% of these cases in patients involve c-myc where the degree of amplification correlates with the aggressiveness of tumor growth and poor prognosis (Schwab, et al., 1990).

c-Myc is a key regulator of growth, proliferation, differentiation, and development. Deregulation of the c-Myc oncoprotein has been reported in apoptosis, transformation, and in malignancies of lymphoid and non-lymphoid origin (Marcu, et al., 1992; Cole, et al., 1986). c-Myc plays a role in the modulation (Benevisty, et al., 1992; Bello-Fernandez, et al., 1993; Gaubatz, et al., 1994; Jansen-Durr, et al., 1993; Daksis, et al., 1994; Philipp, et al., 1994; Galaktinov, et al., 1996) and initiation of transcription (Roy, et al., 1993, Li, et al., 1994; Mai, et al., 1995). It is a short-lived nuclear oncoprotein (Cole, et al., 1986), which is strictly regulated during the cell cycle of normal diploid cells (Cole, et al., 1986; Heikkila, et al., 1987; Karn, et al., 1989). Increased half life of the protein is associated with immortalization and transformation (Marcu, et al., 1992; Cole, et al., 1986). The deregulation of c-Myc is a common feature in many tumors (Marcu, et al., 1992; Cole, et al., 1986), where it frequently is translocated (Stanton, et al., 1983; Potter, et al., 1992; Mai, et al., 1995; Marcu, et al., 1992; Cole, et al., 1986) and/or amplified and overexpressed (Marcu, et al., 1992; Cole, et al., 1986; Feo, et al., 1994; Alitalo, et al., 1985). In addition, the c-myc gene is often the site of proviral insertion (Marcu, et al, 1982; Cole, et al., 1986). Chromosomal aberrations involving c-myc are associated with a poor prognosis (Yokota, et al., 1986).

An amplified gene sequence is termed an "amplicon" and can be chromosomal ("homogeneously staining regions", HSR) or extrachromosomal ("extrachromosomal elements", Ees). Extrachromosomal submicroscopic amplicons that replicate are termed "episomes" (250–5,000 kb), and these can increase in size to be visible by light microscopy, at which point they are termed "double minutes" (>5,000 kb) (Stark, et al., 1993; Hahn, et al., 1993). A variety of mechanisms are involved in the production of gene amplification, and it appears likely that different mechanisms can be involved for different genes in the same cell or for the same gene in different cell types (Stark, et al., 1993; Stark, et al., 1989). The "replication models" predict that a localized replication even can allow an isolated part of the chromosome to repeatedly replicate, i.e., onion-skin, double rolling circle or chromosome-spiral models, and these amplified areas can remain intrachromosomal or be released extrachromosomally. The second major group of mechanisms are the "segregation-driven" mechanisms, i.e., deletion-plus-episome and sister chromatid exchange models. The deletion-plus-episome theory predicts that deletion of a portion of chromosome produces Ees which can proliferate and be subsequently incorporated into random sites on a variety of chromosomes (Carroll, et al., 1988; Windle, et al., 1991).

A model of cyclin D2 gene amplification in CLL (FIG. 4A) is an illustration of the dynamic nature of cyclin D2 gene amplification and is based on the data summarized in FIGS. 1–4. Cyclin D2 (on chromosome 12q13) can be amplified on chromosome 12 and thus give rise to an HSR. In addition, or alternatively, cyclin D2 can be found on extrachromosomal elements (Ees). The latter can be directly generated from the original locus. During this process, it is possible (but not obligatory) that one allele of cyclin D2 is detected. The extrachromosomal elements can re-integrate into chromosome 12q13 or into random loci on chromosome 12 or on other chromosomes. Alternatively, or additionally, Ees can remain extrachromosomally, but they can only be maintained as extrachromosomal structures if they contain replication origins. According to the EM studies, the Ees in CLL cells appear to propagate by replication (see FIGS. 4A and 4B). The dosage of cyclin D2 can also be increased due to the duplication of chromosome 12. Trisomy 12 is a frequently acquired aberration that occurs in a fraction of CLL patients (Crossen, et al., 1997; Dohner, et al., 1997).

Hamkalo et al, 1985 first showed using electron microscopy that the dihydrofolate reductase (DHFR) containing Ees in methorexate-resistant murine 3T3 cells are in circles, and numerous loops can be organized together in a rosette like structure. Similar findings have been observed by others in a variety of cell lines (Esnault, et al, 1994; Nonet, et, al., 1993; Sen, et al., 1994; Schneider, et al., 1992; Cohen, et al., 1996; Cohen, et al., 1997). Esnault et al (Esnault, et al., 1994) isolated 630 kb Ees from a methorexate-resistant cell line and demonstrated that each of these Ees contained on DHFR gene. Transfection of the Ees into the methotrexate-sensitive parent cell line can confer methotrexate resistance. The adenosine deaminase containing Ees in cells grown in 2'-deoxycoformycin (Nonet, et al., 1993), c-myc containing Ees in HL-60 cells (Sen, et al., 1994) and N-myc containing Ees from neuroblastoma cells (Schneider, et al., 1992) have been isolated and cloned. In general, the genes remain intact, can be in a high-to-tail or head-to-head configuration (perhaps depending on the duration of time the Ees have existed) and appear to contain additional genomic loci to the studied gene. It has been suggested that these Ees can replicate and different sized molecules can develop through intra-or intermolecular recombination (Esnault, et al., 1994). In addition, the number of Ees can increase in replicating cells, if they are unequally segregated to each daughter cell and provide the cell with a survival advantage (Stark, et al., 1993; Hahn, et al., 1993).

CLL has been studied by comparative genomic hybridization, which detects areas of chromosomal gene amplification or deletions (Bentz, et al., 1995). Abnormalities are detected in 70% of patients and one-third of these will have amplifications of all or part of chromosome 12 (Bentz, et al., 1995). Amplifications at 12q23–24, 12q13–22 and 12q13–15 have been observed by FISH in one patient with CLL (Merup, et al., 1997). To date, extrachromosomal gene amplification has only rarely been observed in CLL, and one patient has been described with extrachromosomal amplification of c-myc (Wang, et al., 1991). Recently, it was demonstrated that amplification of the cyclin D2 gene is a constant finding in all CLL cells, and appears to be extrachromosomal and cyclin D2 sequences are also randomly integrated into multiple chromosomes (FIG. 2). The cause for the amplification is unknown, although by an extrapolation from the present murine studies, it can occur following prolonged m-Myc overexpression in the stem cells. As c-Myc mRNA is not increased in peripheral blood CLL cells (Greil, et al., 1991), the increase can occur in the CLL stem cells in lymphoid tissue or marrow; the cyclin D2 amplification can then persist in the circulating non-proliferating CLL cell, and, if they have replicative capacity, can actually increase in size and number in these cells.

Cyclin D2 is one of three D cyclins which can have an integral role in the cell cycle. The D cyclins increase during G1 and bind to cyclin dependent kinase-4 (CDK4) or CDK6 with the resulting phosphorylation of the retinoblastoma (Rb) protein and the release of the E2F transcription factors (Sherr, 1994; Hirama, et al., 1995). These factors can then induce the transcription of a variety of genes, e.g., c-myc, DHFR and myb, which area involved in DNA synthesis. It is likely that the three D cyclins have equivalent activities, although their predominant expression depends on the cell type, with cyclins D2 and D3 being primarily present in lymphoid tissue.

While there are some protocols available for providing prognosis but within each stage there is considerable variation in survival. Therefore a better protocol for providing a prognosis and for making decisions on therapeutic strategies is needed.

SUMMARY OF THE INVENTION

According to the present invention, there is provided a method for identifying pre-malignancy, malignancy, and degree of premalignancy and malignancy of a cell by detecting extrachromosomal and intrachromosomal gene amplification. Also provided is a marker for the identification of pre-malignancy, malignancy, and degree of premalignancy and malignancy of a cell containing extrachromosomal and intrachromosomal gene amplification of a gene. A diagnostic tool for the diagnosis and prognosis or cervical cancer containing extrachromosomal and intrachromosomal gene amplification of a gene.

DESCRIPTION OF THE DRAWINGS

Other advantages of the present invention are readily appreciated as the same becomes better understood by reference to the following detailed description when considered in connection with the accompanying drawings wherein:

FIG. 4 shows the amplification of cyclin D2 in CLL cells: Working model (A) and electron microscopy (EM) data (B);

FIG. 19 shows representative images showing c-Myc expression levels and gene amplification within the same cells in vivo using CPFA analyses (Materials and methods); (a) $p53^{-/-}$ fibroblasts (passage 0) were immunostained with anti-c-Myc antibody, two nuclei are shown that overexpress c-Myc fourfold; (a') The same cells show DHFR and c-myc amplification by FISH analysis, the nuclei are stained with DAPI; (a") This image allows one to visualize all FISH hybridization signals obtained for c-myc and DHFR in (a') in the absence of DAPI staining; (b) $p53^{-/-}$ fetal liver-derived hematopoietic cells were immunostained with anti-c-Myc antibody, note a four- to fivefold c-Myc overexpression in the nuclei; (b') shows the overlay image of c-Myc staining and DAPI staining of the nuclei shown in (b); (b") FISH analysis with a CAD probe was performed on the same cells, the nuclei are counterstained with propidium iodide.

DETAILED DESCRIPTION OF THE INVENTION

Figure 1A:
FIG. 1 shows extrachromosomal cyclin D2 gene amplification in interphase CLL cells; A and B show control B cells from a healthy donor; C and D show CD5+/CD19+ cells from a CLL patient; A and C show cyclin C signals, this gene is present as single copy gene in both normal B cells and in CLL cells; B and D show cyclin D2 signals; B shows a single copy cyclin D2 signals in normal B cells, amplified cyclin D2 signals in CLL patient and also shows hybridization efficiency was 30% and >80% for cyclin C and cyclin D2 respectively.
Figure 1B:
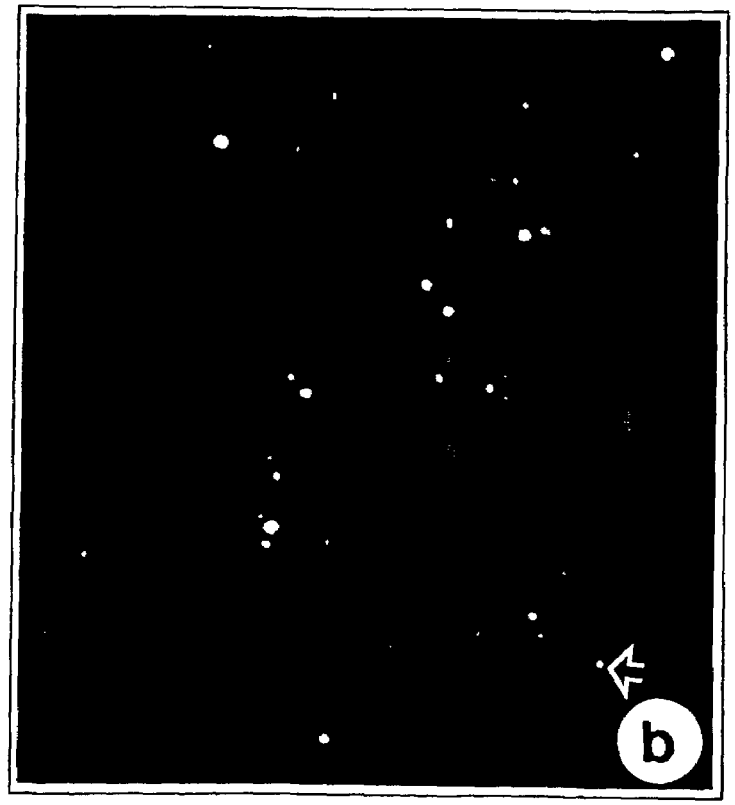
Figure 1C:
Figure 1D:

The present invention provides a method of identifying pre-malignant and malignant cells in cells and tissues. For example the present invention allows identification of micrometastasis, plasmacytomas, cervical cancer, head and neck cancer and CLL and other B-cell leukemias. More specifically, the method includes detecting the presence of extrachromosomal gene amplification in a cell. Additionally, a marker is disclosed which is used in the above method for identifying pre-malignancy and malignancy states in a cell by determining if extrachromosomal gene amplification of the marker is present.

The method of the present invention uses as a marker the presence of extrachromosomal gene amplification as the marker. Further, the present invention has unexpectedly determined that the specific genes that are amplified extrachromosomally are involved in initiation of tumorigenesis and therefore provide therapeutic targets. Therapeutic treatment including gene therapy as for example utilizing suicide genes targeted to the extrachromosomal elements or antisense therapy targeted to the identified genes can be utilized.

By extrachromosomal, it is meant a factor which exists, at least for a time, independent of the chromosome. Accordingly, the extrachromosomal factor is not a part of the chromosome, however these factors can be considered a genetic unit fully equal to those in the chromosomes.

Standard molecular biology techniques known in the art and not specifically described are generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989). Additionally, standard methods in immunology known in the art and not specifically described are generally followed as in Stites et al. (eds), *Basic and Clinical Immunology* (8$^{th}$ *Edition*), Appleton & Lange, Norwalk, Conn. (1994) and Mishell and Shiigi (eds), *Selected Methods in Cellular Immunology*, W.H. Freeman and Co., New York (1980).

Cloning techniques are provided by the present invention. Immunoassays are also provided by the present invention. In general, ELISAs are the preferred immunoassays employed to assess a specimen. Both polyclonal and moloclonal antibodies can be used in the assays. The specific assay to be used can be determined by one skilled in the art.

Antibody production is provided by the present invention. Antibodies can be prepared against the immunogen, or any portion thereof, for example a synthetic peptide based on the sequence. As stated above, antibodies are used in assays and are therefore useful in determining if the appropriate enzyme has been isolated. Antibodies can also be used for removing enzymes from red cell suspensions after enzymatic conversion. Immunogens can be used to produce antibodies by standard antibody production technology well known to those skilled in the art as described generally in Harlow and Lane, *Antibodies: A Laboratory Manual*, Cold Springs Harbor Laboratory, Cold Spring Harbor, N.Y., 1988 and Borrebaeck, *Antibody Engineering-A Practical Guide*, W.H. Freeman and Co., 1992. Antibody fragments can also be prepared from the antibodies and include Fab, F(ab')$_2$, and Fv by methods known to those skilled in the art.

In an embodiment, the present invention provides for the identification of the cyclin D2 gene extrachromosomal amplification. It has been determined that all leukemia cells from patients with CLL have this abnormality and that the extent of amplification increases with duration and stage of disease (see Examples). The overexpression of cyclin D2 is involved in the pathogenesis of the disease. Therefore control of cyclin D2 expression, with for example antisense, can provide a point of therapeutic intervention. Additional genes have been identified such as DHFR, c-MYC, immunoglobulin genes, anti-apoptosis genes, drug-resistance genes, that are amplified and play a role in the pathogenesis of other cancers such as plasmacytomas.

Figure 2A:
FIG. 2 shows extrachromosomal cyclin D2 gene amplification in CLL metaphase and interphase; A shows cyclin D2 signals; B shows chromosome 12 paint; C shows overlay of cyclin D2 hybridization signals (red) as obtained by FISH and chromosome 12 signals (green) as obtained by chromosome painting.
Figure 2B:
Figure 2C:

Referring specifically to the genes relating to CLL, the CLL cells are non-proliferating, Delmer et al, 1995 has recently made the intriguing observation that cyclin D2 mRNA is elevated in this disease. In contrast, cyclin D1 and D3 are not increased in CLL (Delmer, et al, 1995). Whether the increase in cyclin D2 mRNA is related to amplification of the cyclin D2 gene was examined. Twenty-four patients with CLL have been studied and their clinical and laboratory details are shown in Tables 1 and 2. Cyclin D2 gene copy number was studied by FISH and Southern blot analysis. Using FISH, amplification of the cyclin D2 gene was observed in all examined patients, whereas this was not observed in normal B cells. As shown in FIG. 1, multiple cyclin D2 signals were detected suggesting the presence of extrachromosomal elements (Ees), which was confirmed in CLL-metaphases (FIG. 2). CLL metaphases, concomitantly painted with chromosome 12 and probed with cyclin D2 by FISH, demonstrate that cyclin D2 can be lost from its original site on one allele and can be integrated into loci on other chromosomes, including new locations on chromosome 12. Additionally, chromosome 12 derived Ees are observed alone, as well as in conjunction with cyclin D2. This suggests that additional genes on chromosome 12, apart from cyclin D2, undergo amplification.

Figure 3:
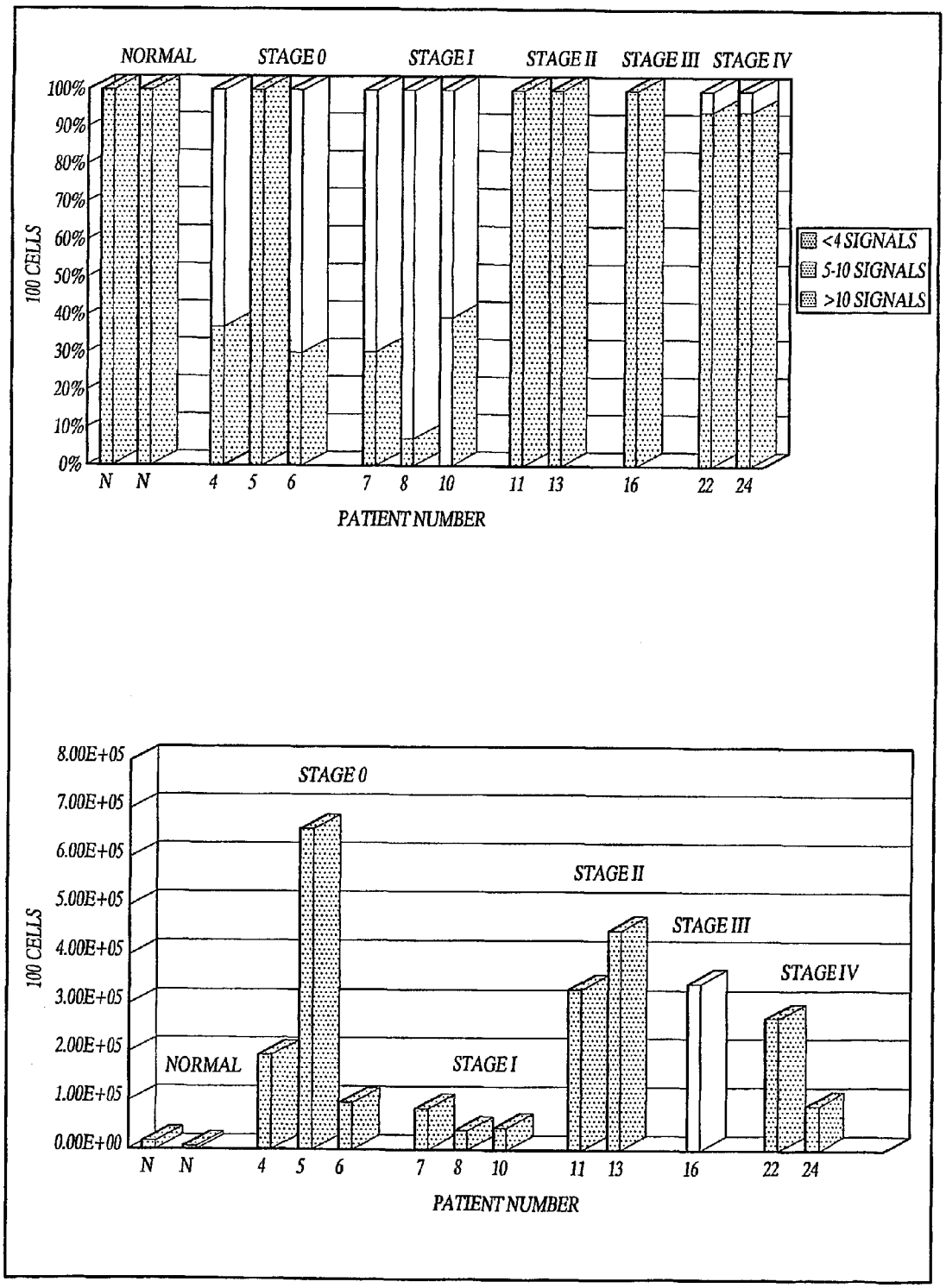
FIG. 3A shows a histogram of fluorescence in situ hybridization (FISH) analysis, and a plot of cyclin D2 signals per 100 cells per CLL stage as detected by FISH and measured by IPLab 3.1 software; as CLL disease stage increases, the number of individual cyclin D2 signals increases per cell.
FIG. 3B shows a histogram of fluorescence in situ hybridization (FISH) analysis wherein total cyclin D2 signal per 100 cells as detected by FISH and measured using IPLab 3.1 software (Signal Analytics), and as CLL disease stage increases the fluorescence intensity of cyclin D2 signals increases.
Figure 4A:
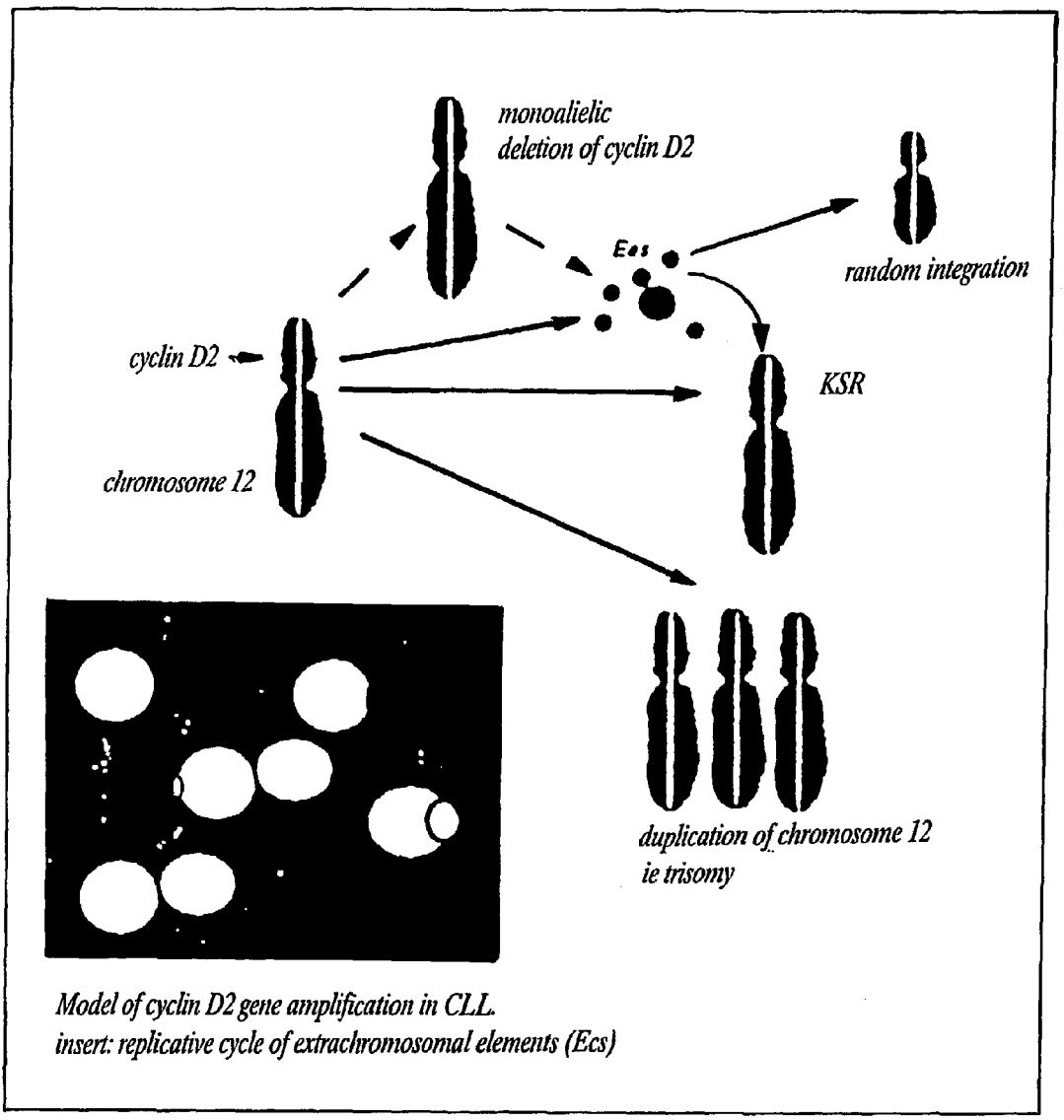
FIG. 4A shows a model of cyclin D2 gene amplification in CLL; the scheme of cyclin D2 amplification is based on the results obtained in CLL patients; cyclin D2 (chromosome 12p13) amplification generates extrachromosomal elements (Ees) or homogeneously staining regions (HSRs) on chromosome 12; HSRs can result from cyclin D2 gene amplification at the original locus, however, 12p13-HSRs can also be generated through the re-integration of cyclin D2 containing Ees into the original locus; the generation of Ees can lead to the loss of one cyclin D2 allele, Ees can re-integrate into random chromosomes; the data also suggest the amplification-independent increase of cyclin D2 gene dosage by the duplication of chromosome 12; Trisomy 12 is an acquired event and has been observed in a fraction of patients (see text), further the insert in this scheme shows the putative replicative cycle of the cyclin D2 containing Ees.

Importantly, all of the leukemia cells from patients with Rai stage 0 disease showed cyclin D2 amplification indicating that this is an early genomic change in CLL. The degree of amplification, as reflected by the number and size of the cyclin D2 signals, increased with the duration and stage of disease (FIGS. 3A and 3B). When examined by electron microscopy (EM), the Ees were found to be in a circular conformation and also showed replication intermediates (FIGS. 4A and B).

Figure 5:
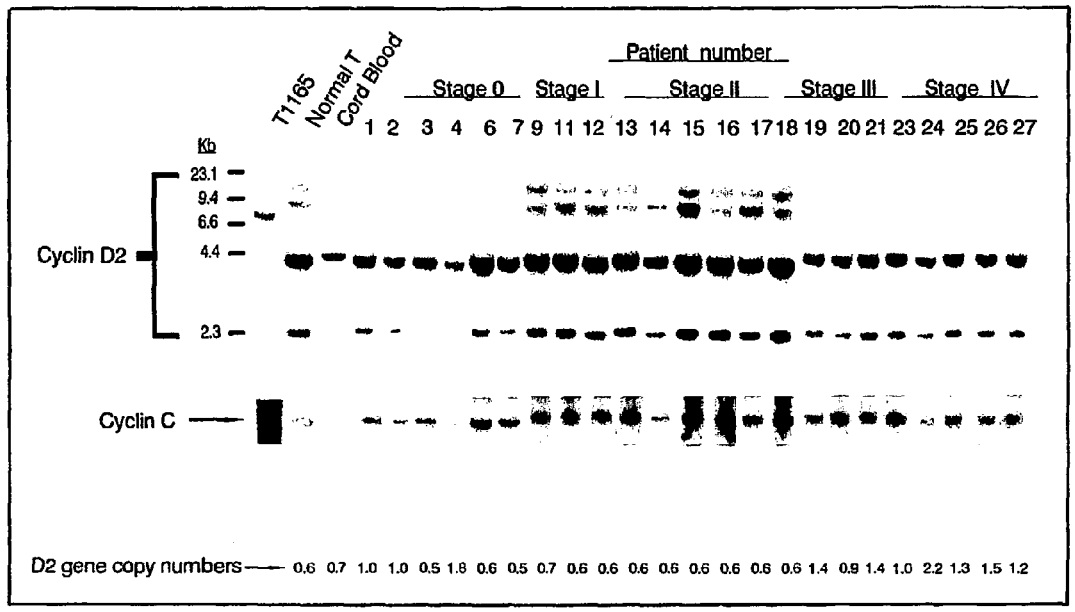
FIG. 5 snows a Southern analysis of DNA samples isolated from 19 CLL patients and control; the DNA was digested with EcoRI and separated on a 0.8% agarose gel, following blotting onto Hybond-N membrane, the filter was hybridized with 600bp NcoI—fragment of human cyclin D2 cDNA, the signal intensity was normalized with the β-actin hybridization signals. The amplification factors obtained were 1.5 to 2.5.
Figure 6:
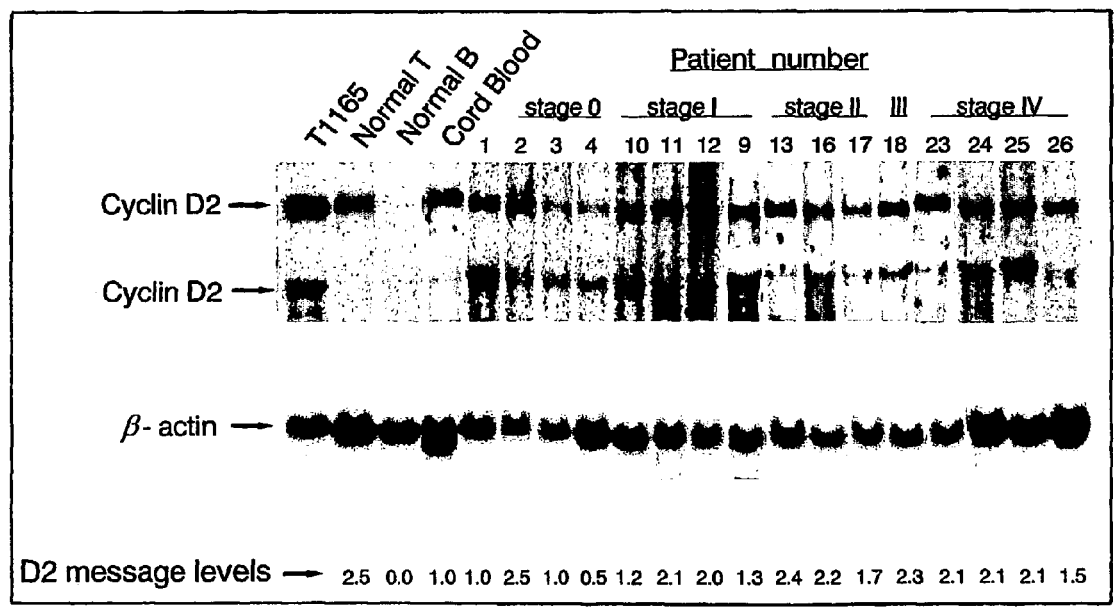
FIG. 6 shows a Northern analysis of total RNA isolated from 16 CLL patients and control (normal B); the RNA (25 ug) was separated on a 1.0% agarose gel, blotted onto Hybond-N membrane and hybridizations were performed with a human cyclin D2 cDNA (as described in FIG. 5), hybridizations were normalized with β-actin; all CLL patients express cyclin D2, but not normal B cells; T1165 is a positive control showing cyclin D2 mRNA levels in a mouse plasmacytoma, normal T and human cord blood express a cyclin D2 transcript.
Figure 7:
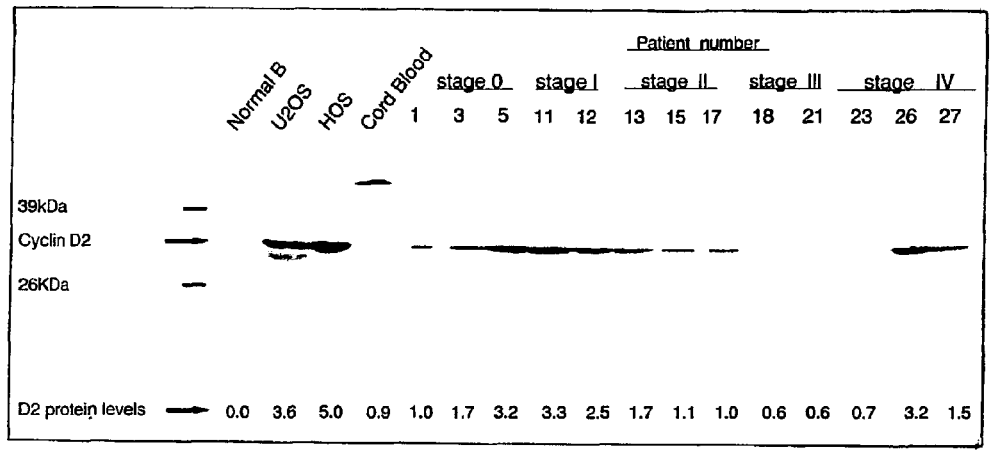
FIG. 7 shows a Western analysis of CLL patients (Rai stages 0–IV) and normal B lymphocytes; 100 ug protein were loaded per lane onto a 10% SDS-polyacrylamide gel, after blotting onto a Hybond C-super membrane, the membrane was probed with cyclin D2 antibody (Santa Cruz, rabbit polyclonal IgG) and detected with peroxidase labeled anti-rabbit antibody (Amersham) using the ECL detection kit (Amersham), the 35 kDa cyclin D2 protein is shown by an arrow; control B cells and cord blood do not show detectable levels of cyclin D2 protein; all CLL patients show cyclin D2 protein, the level increases as the disease progresses, stage III and IV patients show also cyclin D2 protein degradation.

Southern blotting showed an increase in cyclin D2 hybridization signals in 50% of the patients (FIG. 5). As Ees are not detected with a Southern Blot, this indicates that part of the amplification is related to trisomy 12 and/or amplification of the cyclin D2 locus on 12p.13 (Inaba, et al., 1992). Cyclin D2 mRNA and proteins levels were increased in most patients, with the highest levels being seen in patients with advanced or prolonged disease (FIGS. 6 and 7).

These findings suggest that cyclin D2, and/or other genes on chromosome 12, can play an important role in the initiation of CLL. In addition, cyclin D2 overexpression provides the cells with a survival advantage, as the degree of cyclin D2 amplification increases with disease duration and stage. This is supported by the observation that trisomy 12 is a common acquired abnormality in CLL, which will increases cyclin D2 expression. Evidence also suggests a role for cyclin D2 in CLL cell survival, as flavopiridol, an inhibitor of CDK2 and CDK4, is highly cytotoxic to CLL cells in vitro (Byrd, et al., 1997).

Overexpression of cyclin D2 is involved in the initiation of CLL, either through its effects on differentiation or apoptosis. For example, the murine 32Dc13 non-leukemic myeloid cell line grows in blastic phase in vitro in the presence of IL3 and undergoes apoptosis when IL3 is withdrawn (Ando, et al. 1993). However, following transfection of D cyclins these cells can survive longer on withdrawal of IL3. In the same cells, differentiation to mature neutrophils occurs when the cells are incubated with G-CSF. However, when these cells are transfected with cyclin D2, differentiation with G-CSF is prevented (Kato, et al., 1993). In addition, overexpression of cyclin D2 can cause tumor progression and transformation through its effects on genomic instability, as has been observed with cyclin D1 (Zhou, et al., 1996). When cyclin D1 was overexpressed in a rat epithelial cell line, these cells showed a marked increase in amplification of the CAD gene when cells were exposed to the drug, PALA (Zhou, et al., 1996). Thus, overexpression of cyclin D2 leads to the accumulation of specific genetic changes, e.g., 13q14 del or 17 del, which are associated with disease progression and transformation.

Although the levels of cyclin D2 protein are increased in CLL, it has not yet been established that the protein is functional. The SDKs are inhibited by a variety of proteins and it has recently been shown that one of these, $p27^{kip1}$, is increased in CLL (Vrhovac, et al., 1997). $p27^{kip1}$ can inactivate several cyclin/CDK complexes, including cyclin D2/CDK4 (Hirama, et al, 1995; Muller, et al., 1997; Blain, et al., 1997). In proliferating cells, upregulation of p27kip1 can induce G1 arrest (Kawamata, et al., 1998) and apoptosis (Wang, et al., 1997), but whether the level of p27kip1 in CLL cells is sufficient to abrogate cyclin D2 activity requires further study. Interestingly, p27kip1 is located at 12p.12.3 (Hoglund, et al., 1996), close to cyclin D2 at 12p13 (Inaba, et al., 1992), and can be coamplified.

The extrachromosomal gene amplification is an early event during the induction of murine malignancies and that cyclin D2 gene amplification occurs in a variety of murine B cell malignancies, particularly those with overexpression of c-Myc. More recently, the unique observation was made that extrachromosomal amplification of the cyclin D2 gene occurs in CLL, and that all leukemia cells from patients with newly diagnosed and early stage disease have this abnormality. As the amplification is also associated with an increase in cyclin D2 mRNA and protein, these findings suggest that overexpression of cyclin D2 plays a role in the pathogenesis of this disease. The extent of amplification increases with duration and stage of disease, suggesting that the cyclin D2 provides a survival advantage. The cyclin D2 gene is located on chromosome 12p13 and this also explains why trisomy 12 is a relatively common abnormality in CLL, particularly in patients with advanced disease.

However, studies have also demonstrated that there is extrachromosomal amplification of other genes apart from cyclin D2 and other genes can be coamplified with cyclin D2.

Inducible transfectants have been generated that allow the experimental overexpression of the c-Myc oncoprotein (Mai, 1994). The inducible overexpression of c-Myc is followed by the enhanced binding of the c-Myc/Max heterodimer (Mai, 1994; Mai, et al., 1996). Furthermore, the DHFR gene is amplified following the inducible overexpression of c-Myc and the increase in the c-Myc/Max heterodimer formation at the DHFR E-box motifs (Mai, 1994; Mai, et al., 1996). c-Myc overexpression thus affects the genomic stability of the DHFR locus.

The amplification of the DHFR gene occurs within three cell doublings and increases 1.8- to 4.2-fold during this time period. The amplification is locus-specific, since other loci are unaffected irrespective of c-Myc overexpression coincides with the elevated expression of the DHFR enzyme (Luecke-Huhle, et al., 1996). The amplification of the DHFR locus is transient if c-Myc overexpression is induced for a single time (Mai, et al., 1996). Constitutive c-Myc overexpression is associated with both the amplification and the rearrangement of the DHFR gene (Mai, et al., 1996). In agreement with these findings, it was observed that the prolonged induction of c-Myc in inducible lines is accompanied with ongoing amplification and rearrangements of the DHFR gene (Mai, et al., 1996). Moreover, the prolonged induction of c-Myc overexpression induces a significant increase in the formation of telomere-centromere-fusions and of extrachromosomal elements (Mai, et al., 1996).

Recent studies have also shown that DHFR gene amplification occurs in association with c-Myc upregulation in p53 deficient mice in vivo (Fukasawa, et al., 1997). However, using p53-deficient mice as an experimental model does not resolve the question as to whether c-Myc overexpression precedes the amplification of the DHFR gene. The present work was initiated to determine whether the locus-specific amplification of the DHFR gene occurred as a result of induced c-Myc overexpression in vivo.

To this end, an animal model of c-Myc-dependent neoplasia was examined, the mouse plasmacytoma. Plasmacytomagenesis is the neoplastic development of mouse B lineage cells (Potter et al., 1992). Four criteria generally define a plasmacytoma (PCT) cell: i) It has a well developed Golgi and is rich in endoplasmic reticulum; ii) It predominantly secretes IgG and IgA. IgM and IgD were reported in a few cases; iii) It commonly displays a translocation between c-Myc (chromosome 15) and immunoglobulin (Ig) loci (chromosomes 12, 6, 16), and iv) c-Myc is constitutively expressed due to the juxtaposition of myc and Ig loci. PCTs can be experimentally induced in the mouse, with a strain specific predisposition (Potter, et al., 1992). Balb/c and NZB mice strains are susceptible to PCTgenesis, whereas DBA/2, C57BL/6 and C3H mice are not (<5% develop paraffin oil induced PCTs). Susceptibility loci are located on chromosome 4 and 1, respectively (Mock, et al., 1993; Potter, et al., 1994). The experimental induction of PCTs is achieved with paraffin oils and pristane or plastic implants; in rare cases, plasmacytomas can arise spontaneously (Potter, et al., 1992; Silva, et al., 1997).

To examine whether c-Myc-dependent DHFR gene amplification occurred in vivo, PCT-susceptible Balb/c mice were analyzed following the i.p. injection of pristane that leads to the induction of PCTs in these mice (Potter, et al., 1992). The c-Myc overexpression associated amplification of the DHFR gene in pristane-injected Balb/c mice is shown. This amplification does not involve the polyploidization of the DHFR carrying chromosome 13 and is predominantly observed on extrachromosomal elements.

The focus of the experimental work herein has been on MYC-dependent genomic instability. The c-Myc overexpression is associated with the non-random amplification and rearrangement of the dihydrofolate reductase (Dhfr, ref. Mai 1994 and Mai et al., 1996) gene and the gene encoding the R2 subunit of ribonucleotide reductase, RNR2, but not the RNR1 gene (T. I. Kuschak et al., submitted).

In the present study, evidence is shown of MYC-dependent amplification of the cyclin D2 locus and attendant increased cyclin D2 gene products. These findings link c-Myc overexpression and cell cycle regulation for the first time at the level of genomic instability of this GI cyclin. Based on these findings, a model of MYC-dependent genomic instability and neoplasia is established.

Constitutive Myc expression is a key element in the induction of mouse plasmacytomas and human Burkitt lymphomas. The mechanism through which Myc over-expression contributes to this and other forms of carcinogenesis remains elusive. One consequence of Myc overexpression is a shortening of the G1 phase of cell cycle, these elements that regulated this phase were studied and cloned cDNAs for the 3 mouse D cyclins. Northern blots of RNAs from B-cell tumors showed that plasmacytomas have not only abundant c-Myc transcript but also high levels of cyclin D2 transcripts. In the genomic clone a 4 CACGTG "EMS (E-box Myc Site) motifs" was found upstream of the cyclin D2 coding region. These EMS motifs bind Myc/Max heterodimers, suggesting that constitutive Myc expression can cause cyclin D2 overexpression. Cyclin D2 DNA and mRNA were examined in established mouse and human tumors that expressed high levels of Myc. Also examined was the substantial amplification of the cyclin D2 gene by Southern blotting and by FISH.

To follow the Myc/cyclin D2 connection in vitro, Myc activity was upregulated in two cell lines using an expression vector making a Myc-ER chimera that is activated by 4-hydroxytamoxifen (4HT). In mouse pre-B cells and fibroblasts that bear Myc-ERTM, cyclin D2 mRNA rose after three to four days of 4HT activation of Myc. Simultaneously, evidence of amplification: in the form of extrachromosomal elements was seen by FISH. Thus, one important action of Myc seems to be the induction of gene amplification, a form of genomic instability. The associated increase in cyclin D2 gene products, apparently due to the amplification, rather than upregulated transcription, can contribute to uncontrolled growth.

The dihydrofolate reductase (DHFR) gene is a target of c-Myc in genomic instability. The induced overexpression of c-Myc in cell lines is followed by the amplification and rearrangement of the DHFR gene. Furthermore, the constitutive upregulation of c-Myc protein coincides with genomic instability of the DHFR gene in lymphoid, non-lymphoid and in tumor lines. The amplification of the DHFR gene is locus-specific and independent of species origins. The question has been addressed whether inducible deregulation of c-Myc is followed by DHFR gene amplification in vivo. Therefore, the DHFR gene is a target of c-Myc-dependent neoplasia in vivo and plays a role in genomic instability during the initiation of neoplastic transformation.

The present invention also provides that the DHFR gene is a marker or indicator of pre-malignant and malignancy states. More specifically, the DHFR gene is amplified in cervical cancer. It has additionally been established that the degree of DHFR gene amplification can be used as a measurement of the degree of premalignancy and malignancy. Thus, based on the amount of DHFR gene amplification found in a lesion, it can be determined the stage of the cancer. Specifically, there is a direct correlation between the amount of DHFR gene amplification and the tumor stage, such that as DHFR gene amplification increases the corresponding tumor stage also increases. Therefore, DHFR amplification can be used as a sensitive biomarker for all stages of cervical cancer.

It has also been established that the loss of p53 tumor suppressor functions results in genetic instability, characteristically associated with changes in chromosome ploidy and gene amplification. In vivo, cells from various organs of four to six-week old p53-nullizygous (p53$^{-/-}$) mice display aneuploidy and frequent gene amplification as well as evidence of apoptosis. Regardless of tissue types, many p53$^{-/-}$ cells contain multiple centrosomes and abnormally formed mitotic spindles. Thus, chromosome instability in vivo is associated with abnormal centrosome amplification. Moreover, a significant increase in the number of cells overexpressing c-Myc in p53$^{-/-}$ mice is observed. Consistent with previous studies showing that c-Myc overexpression is associated with gene amplification in vitro, many of the p53$^{-/-}$ cells exhibited, in the same cell, c-Myc overexpression and amplified c-myc, dihydrofolate reductase (DHFR), and carbamoyl-phosphate syntehtase-asparate transcarbamoyl-dihydroorotase (CAD) genes. Furthermore, apoptosis was frequently observed in cells isolated from p53$^{-/-}$ mice. The apoptotic cells contained abnormally amplified centrosomes, displayed aneuploidy, high levels of c-Myc expression, as well as gene amplification. These results indicate that a high number of aberrant cells is eliminated by p53-independent pathways in vitro.

In another embodiment of the present invention there is provided a kit for identifying pre-malignancy and malignant states of a cell. The kit contains a device for detecting extrachromosomal gene amplification. More specifically, the kit detects extrachromosomal gene amplification of genes such as DHFR, C-Myc, immunoglubulin genes, anti-apoptosis genes and drug-resistance genes. The process for detecting the gene amplification uses a combined protein and FISH analysis. Such analysis includes a detecting gene amplification using quantitative fluorescence immunohistochemistry. The kit can also include items for therapeutic intervention of cells having such extrachromosomal gene amplification Such therapeutic intervention includes therapeutically targeting the genes which have extrachromosomal amplification. Such therapy includes gene therapy such as suicide genes which are targeted toward extrachromosomal elements or antisense therapy targeted to the identified gene.

The methods used with and the utility of the present invention can be shown by the following non-limiting examples and accompanying figures and incorporated by reference in their entirety.

The above discussion provides a factual basis for the use of markers for the identification of pre-malignancy and malignancy of cells. The methods used with and the utility of the present invention can be shown by the following non-limiting examples and accompanying figures.

EXAMPLES

General Methods:

General methods in molecular biology: Standard molecular biology techniques known in the art and not specifically described are generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989). Polymerase chain reaction (PCR) is carried out generally as in *PCR Protocols: A Guide To Methods And Applications*, Academic Press, San Diego, Calif. (1990). Reactions and manipulations involving other nucleic acid techniques, unless stated otherwise, are performed as generally described in Sambrook et al., 1989, *Molecular Cloning: A Laboratory Manual*, Cold Spring Harbor Laboratory Press, and methodology as set forth in U.S. Pat. Nos. 4,666,828; 4,683,202; 4,801,531; 5,192,659 and 5,272,057 and incorporated herein by reference. In-situ (In-cell) PCR in combination with Flow Cytometry can be used for detection of cells containing specific DNA and mRNA sequences (Testoni et al, 1996, Blood 87:3822.)

General methods in immunology: Standard methods in immunology known in the art and not specifically described are generally followed as in Stites et al.(eds), Basic and Clinical Immunology (8th Edition), Appleton & Lange, Norwalk, Conn. (1994) and Mishell and Shiigi (eds), Selected Methods in Cellular Immunology, W.H. Freeman and Co., New York (1980).

Immunoassays In general, ELISAs are the preferred immunoassays employed to assess a specimen. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, *Molecular Cloning: A Laboratory Manual*, Cold Springs Harbor, New York, 1989.

Transgenic and Knockout Methods

The present invention can provide for transgenic gene and polymorphic gene animal and cellular (cell lines) models as well as for knockout models. These models are constructed using standard methods known in the art and as set forth in U.S. Pat. Nos. 5,487,992, 5,464,764, 5,387,742, 5,360,735, 5,347,075, 5,298,422, 5,288,846, 5,221,778, 5,175,385, 5,175,384, 5,175,383, 4,736,866 as well as Burke and Olson (1991), Capecchi (1989), Davies et al. (1992), Dickinson et al. (1993), Duff and Lincoln (1995), Huxley et al. (1991), Jakobovits et al. (1993), Lamb et al. (1993), Pearson and Choi (1993), Rothstein (1991), Schedl et al. (1993), Strauss et al. (1993). Further, patent applications WO 94/23049, WO 93/14200, WO 94/06908, WO 94/28123 also provide information.

For gene therapy: By gene therapy as used herein refers to the transfer of genetic material (e.g DNA or RNA) of interest into a host to treat or prevent a genetic or acquired disease or condition phenotype. The genetic material of interest encodes a product (e.g. a protein, polypeptide, peptide or functional RNA, antisense) whose production in vivo is desired. For example, the genetic material of interest can encode a hormone, receptor, enzyme, polypeptide or peptide or antisense sequence of therapeutic value. For a review see, in general, the text "Gene Therapy" (Advances in Pharmacology 40, Academic Press, 1997).

Two basic approaches to gene therapy have evolved: (1) ex vivo and (2) in vivo gene therapy. In ex vivo gene therapy cells are removed from a patient, and while being cultured are treated in vitro. Generally, a functional genetic sequence is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to have the transfected genetic sequence expressed in situ.

In in vivo gene therapy, target cells are not removed from the subject rather the genetic sequence to be transferred is introduced into the cells of the recipient organism in situ, that is within the recipient. Alternatively, if the host gene is defective, the gene is repaired in situ (Culver, 1998). These genetically altered cells have been shown to express the transfected gene sequence in situ.

The gene expression vehicle is capable of delivery/transfer of heterologous nucleic acid into a host cell. The expression vehicle includes elements to control targeting, expression and transcription of the nucleic acid in a cell selective manner as is known in the art. It is noted that often the 5'UTR and/or 3'UTR of the gene can be replaced by the 5'UTR and/or 3'UTR of the expression vehicle. Therefore as used herein the expression vehicle can, as needed, not include the 5'UTR and/or 3'UTR of the gene of interest and only include the specific amino acid coding region of the gene of interest.

The expression vehicle can include a promotor for controlling transcription of the heterologous material and can be either a constitutive or inducible promotor to allow selective transcription. Enhancers that can be required to obtain necessary transcription levels can optionally be included. Enhancers are generally any non-translated DNA sequence which works contiguously with the coding sequence (in cis) to change the basal transcription level dictated by the promoter. The expression vehicle can also include a selection gene as described herein below.

Vectors can be introduced into cells or tissues by any one of a variety of known methods within the art. Such methods can be found generally described in Sambrook et al., *Molecular Cloning: A Laboratory Manual*, Cold Springs Harbor Laboratory, New York (1989, 1992), in Ausubel et al., *Current Protocols in Molecular Biology*, John Wiley and Sons, Baltimore, Md. (1989), Chang et al., *Somatic Gene Therapy*, CRC Press, Ann Arbor, Mich. (1995), Vega et al., *Gene Targeting*, CRC Press, Ann Arbor, Mich. (1995), *Vectors: A Survey of Molecular Cloning Vectors and Their Uses*, Butterworths, Boston Mass. (1988) and Gilboa et al (1986) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods.

Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

A specific example of DNA viral vector for introducing and expressing recombinant sequences is the adenovirus derived vector Adenop53TK. This vector expresses a herpes virus thymidine kinase (TK) gene for either positive or negative selection and an expression cassette for desired recombinant sequences. This vector can be used to infect cells that have an adenovirus receptor which includes most cancers of epithelial origin as well as others. This vector as well as others that exhibit similar desired functions can be used to treat a mixed population of cells and can include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefore a means by which infection can be controlled because it provides inducible suicide through the addition of antibiotic. Such protection ensures that if, for example, mutations arise that produce altered forms of the viral vector or recombinant sequence, cellular transformation will not occur.

Features that limit expression to particular cell types can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention will depend on desired cell type to be targeted and are known to those skilled in the art. For example, if breast cancer is to be treated then a vector specific for such epithelial cells can be used. Likewise, if diseases or pathological conditions of the hematopoietic system are to be treated, then a viral vector that is specific for blood cells and their precursors, preferably for the specific type of hematopoietic cell, can be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

The recombinant vector can be administered in several ways. If viral vectors are used, for example, the procedure can take advantage of their target specificity and consequently, do not have to be administered locally at the diseased site. However, local administration can provide a quicker and more effective treatment, administration can also be performed by, for example, intravenous or subcutaneous injection into the subject. Injection of the viral vectors into a spinal fluid can also be used as a mode of administration, especially in the case of neuro-degenerative diseases. Following injection, the viral vectors will circulate until they recognize host cells with the appropriate target specificity for infection.

An alternate mode of administration can be by direct inoculation locally at the site of the disease or pathological condition or by inoculation into the vascular system supplying the site with nutrients or into the spinal fluid. Local administration is advantageous because there is no dilution effect and, therefore, a smaller dose is required to achieve expression in a majority of the targeted cells. Additionally, local inoculation can alleviate the targeting requirement required with other forms of administration since a vector can be used that infects all cells in the inoculated area. If expression is desired in only a specific subset of cells within the inoculated area, then promoter and regulatory elements that are specific for the desired subset can be used to accomplish this goal. Such non-targeting vectors can be, for example, viral vectors, viral genome, plasmids, phagemids and the like. Transfection vehicles such as liposomes can also be used to introduce the non-viral vectors described above into recipient cells within the inoculated area. Such transfection vehicles are known by one skilled within the art.

Antisense Therapy: Many reviews have covered the main aspects of antisense (AS) technology and its enormous therapeutic potential (Wright and Anazodo, 1995). There are reviews on the chemical (Crooke, 1995; Uhlmann et al, 1990), cellular (Wagner, 1994) and therapeutic (Hanania, et al, 1995; Scanlon, et al, 1995; Gewirtz, 1993) aspects of this rapidly developing technology. Within a relatively short time, ample information has accumulated about the in vitro use of AS nucleotide sequences in cultured primary cells and cell lines as well as for in vivo administration of such nucleotide sequences for suppressing specific processes and changing body functions in a transient manner. Further, enough experience is now available in vitro and in vivo in animal models and human clinical trials to predict human efficacy.

Antisense intervention in the expression of specific genes can be achieved by the use of synthetic AS oligonucleotide sequences (for recent reports see Lefebvre-d'Hellencourt et al, 1995; Agrawal, 1996; Lev-Lehman et al, 1997). AS oligonucleotide sequences can be short sequences of DNA, typically 15–30 mer but can be as small as 7 mer (Wagner et al, 1996), designed to complement a target mRNA of interest and form an RNA:AS duplex. This duplex formation can prevent processing, splicing, transport or translation of the relevant mRNA. Moreover, certain AS nucleotide sequences can elicit cellular RNase H activity when hybridized with their target mRNA, resulting in mRNA degradation (Calabretta et al, 1996). In that case, RNase H will cleave the RNA component of the duplex and can potentially release the AS to further hybridize with additional molecules of the target RNA. An additional mode of action results from the interaction of AS with genomic DNA to form a triple helix which can be transcriptionally inactive.

Phosphorothioate antisense oligonucleotides do not normally show significant toxicity at concentrations that are effective and exhibit sufficient pharmacodynamic half-lives in animals (Agarwal et al., 1996) and are nuclease resistant. Antisense induced loss-of-function phenotypes related with cellular development were shown for the glial fibrillary acidic protein (GFAP), for the establishment of tectal plate formation in chick (Galileo et al., 1991) and for the N-myc protein, responsible for the maintenance of cellular heterogeneity in neuroectodermal cultures (ephithelial vs. neuroblastic cells, which differ in their colony forming abilities, tumorigenicity and adherence) (Rosolen et al., 1990; Whitesell et al, 1991). Antisense oligonucleotide inhibition of basic fibroblast growth factor (bFgF), having mitogenic and angiogenic properties, suppressed 80% of growth in glioma cells (Morrison, 1991) in a saturable and specific manner. Being hydrophobic, antisense oligonucleotides interact well with phospholipid membranes (Akhter et al., 1991). Following their interaction with the cellular plasma membrane, they are actively (or passively) transported into living cells (Loke et al., 1989), in a saturable mechanism predicted to involve specific receptors (Yakubov et al., 1989).

Instead of an antisense sequence as discussed herein above, ribozymes can be utilized. This is particularly necessary in cases where antisense therapy is limited by stoichiometric considerations (Sarver et al., 1990, Gene Regulation and Aids, pp. 305–325). Ribozymes can then be used that will target the same sequence. Ribozymes are RNA molecules that possess RNA catalytic ability (see Cech for review) that cleave a specific site in a target RNA. The number of RNA molecules that are cleaved by a ribozyme is greater than the number predicted by stochiochemistry. (Hampel and Tritz, 1989; Uhlenbeck, 1987).

Ribozymes catalyze the phosphodiester bond cleavage of RNA. Several ribozyme structural families have been identified including Group I introns, RNase P, the hepatitis delta virus ribozyme, hammerhead ribozymes and the hairpin ribozyme originally derived from the negative strand of the tobacco ringspot virus satellite RNA (sTRSV) (Sullivan, 1994; U.S. Pat. No. 5,225,347, columns 4–5). The latter two families are derived from viroids and virusoids, in which the ribozyme is believed to separate monomers from oligomers created during rolling circle replication (Symons, 1989 and 1992). Hammerhead and hairpin ribozyme motifs are most commonly adapted for trans-cleavage of mRNAs for gene therapy (Sullivan, 1994). The ribozyme type utilized in the present invention is selected as is known in the art. Hairpin ribozymes are now in clinical trial and are the preferred type. In general the ribozyme is from 30–100 nucleotides in length.

The present invention provides pharmaceutical compositions for the delivery of the oligonucleotides of the present invention. The pharmaceutical compositions contain active ingredients as described herein and a pharmaceutically suitable carrier or diluent. The compositions can be administered orally, subcutaneously or parenterally including intravenous, intraarterial, intramuscular, intraperitoneally, and intranasal administration as well as intrathecal and infusion techniques as required by the cells being treated. For delivery within the CNS intrathecal delivery can be used with for example an Ommaya reservoir or other methods known in the art. The pharmaceutically acceptable carriers, diluents, adjuvants and vehicles as well as implant carriers generally refer to inert, non-toxic solid or liquid fillers, diluents or encapsulating material not reacting with the active ingredients of the invention. Implants of the compounds are also useful. In general the pharmaceutical compositions are sterile.

Modifications or analogues of nucleotides can be introduced to improve the therapeutic properties of the nucleotides. Improved properties include increased nuclease resistance and/or increased ability to permeate cell membranes.

Nuclease resistance, where needed, is provided by any method known in the art that does not interfere with biological activity of the antisense oligodeoxynucleotides and/or ribozymes as needed for the method of use and delivery (Iyer et al., 1990; Eckstein, 1985; Spitzer and Eckstein, 1988; Woolf et al., 1990; Shaw et al., 1991). Modifications that can be made to oligonucleotides in order to enhance nuclease resistance include modifying the phophorous or oxygen heteroatom in the phosphate backbone. These include preparing methyl phosphonates, phosphorothioates, phosphorodithioates and morpholino oligomers. In one embodiment it is provided by having phosphorothioate bonds linking between the four to six 3=-terminus nucleotide bases. Alternatively, phosphorothioate bonds link all the nucleotide bases. Other modifications known in the art can be used where the biological activity is retained, but the stability to nucleases is substantially increased.

The present invention also includes all analogues of, or modifications to, an oligonucleotide of the invention that does not substantially affect the function of the oligonucleotide. The nucleotides can be selected from naturally occurring or synthetic modified bases. Naturally occurring bases include adenine, guanine, cytosine, thymine and uracil. Modified bases of the oligonucleotides include xanthine, hypoxanthine, 2-aminoadenine, 6-methyl, 2-propyl and other alkyl adenines, 5-halo uracil, 5-halo cytosine, 6-aza cytosine and 6-aza thymine, psuedo uracil, 4-thiuracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine.

In addition, analogues of nucleotides can be prepared wherein the structure of the nucleotide is fundamentally altered and that are better suited as therapeutic or experimental reagents. An example of a nucleotide analogue is a peptide nucleic acid (PNA) wherein the deoxyribose (or ribose) phosphate backbone in DNA (or RNA0 is replaced with a polyamide backbone which is similar to that found in peptides. PNA analogues have been shown to be resistant to degradation by enzymes and to have extended lives in vivo and in vitro. Further, PNAs have been shown to bind stronger to a complementary DNA sequence than a DNA molecule. This observation is attributed to the lack of charge repulsion between the PNA strand and the DNA strand. Other modifications that can be made to oligonucleotides include polymer backbones, cyclic backbones, or acyclic backbones.

The active ingredients include oligonucleotides that are nuclease resistant needed for the practice of the invention or a fragment thereof shown to have the same effect targeted against the appropriate sequence(s) and/or ribozymes. Combinations of the active ingredients can be used.

The antisense oligonucleotides (and/or ribozymes) of the present invention can be synthesized by any method known in the art for ribonucleic or deoxyribonucleic nucleotides.

For example, an Applied Biosystems 380B DNA synthesizer can be used. When fragments are used, two or more such sequences can be synthesized and linked together for use in the present invention.

The nucleotide sequences of the present invention can be delivered either directly or with viral or non-viral vectors. When delivered directly the sequences are generally rendered nuclease resistant. Alternatively the sequences can be incorporated into expression cassettes or constructs such that the sequence is expressed in the cell. Generally the construct contains the proper regulatory sequence or promotor to allow the sequence to be expressed in the targeted cell.

Delivery of gene products/therapeutics (compound): The compound of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

Isolation of EEs. $1-5\times10^7$ cells are lysed in 0.6% SDS/0.OIM EDTA (pH 7.5) for 20 minutes at room temperature. The lysate is then brought to a final concentration of 1M NaC1 and left overnight at 40C. The insoluble NaC1/SDS/chromatin fraction is pelleted by centrifugation at 17,000 rpm for 30 minutes at 4° C. The supernatant is the so-called Hirt extract and is collected. It contains the bulk of the EBs, but it can also contain contamination with small linear fragments of genomic DNA (Ref. 2) and apoptotic DNA fragments.

Fixation of EEs. The Hirt extract is mixed with an equal volume of freshly prepared methanol:acetic acid (3:1). This mixture can be stored at 4° C. for months.

Dropping of EEs onto slides and their fixation. The following protocol allows the fixation of the EEs onto glass slides, and it guarantees that the EEs are well-spread, but contained within a small area. Briefly: 40 p1 of fixed Ees (Wit extract in fixative) are dropped onto precooled slides (20 seconds on dry ice), and the slides are immediately moved onto a slide warmer (37° C.). When almost dry, the slides are dipped into 50% acetic acid and then dried to completion on the slide warmer (370 C). The area onto which the EEs were dropped is marked with a diamond pen.

Analysis of the EEs sample under the fluorescent microscope. 4'6' diamidino-2-phenylindole (DAPI) (Ipg/ml in PBS) is used to stain both the DNA in the, EEs and any genomic DNA contaminants. Anti-bleach (Ref. £5.) is added to preserve the fluorescence of the sample and as a mount for the cover slip. Under a 63x oil immersion objective and a UV filter, the sample is examined using a fluorescent microscope. DAPI-stained EEs are visible as distinct dots, while genomic DNA appears as DAPI-stained fibres (FIG. 1).

FISH analysis of EEs (FISH-EEs). FISH is carried out according to previously published protocols (Refs. 4. 5 .9 Briefly: the slides are treated with RNAse and pepsin as described for metaphase chromosomes and interphase cells. DNA probes are labeled with haptens by random priming as described, and hybridizations are performed in 50% formamide/2xSSC/50 mM phosphate pH 7/10% dextran sulfate overnight at 37° C. in a humidified incubator. Post-hybridization washes are carried out as follows: 3x5 minutes at 42° C. in 50%, formamide/2xSSC; 5x2 minutes at room temperature in 2xSSC. Prior to the use of antibodies, the slides are blocked in 100% serum. Anti-hapten antibodies, conjugated with fluorescein (FITC) or Texas Red (TR), are used to visualize the hapten-labeled probes. The antibody incubation is carried out for 30 minutes at 37° C. The unbound antibodies are washed off at 42° C. in 4xSSC/0.1% Tween 20 for 3x5 minutes. DAPI (Ip.g/ml in PBS, 5 minutes) is used to stain the DNA and the slides are mounted in anti-bleach. In the examples shown in FIG. 2, the following probes have been used: human c-myc cDNA (Ref. 4.~1)~ human cyclin C cDNA (Ref. ~), mouse cyclin D2 genomic DNA (Ref. j), mouse ribonucleotide reductase Ri and R2 (Ri and R2) cDNA (Ref. fID~ all of which were labeled with digoxigenin. After hybridization, the annealed probe is visualized by incubation with anti-digoxigenin-fluorescein antibody (Boehringer Mannheim). An additional probe, a mouse dihydrofolate reductase (DHFR) cDNA (Ref. 4~), was labeled with biotin, detected with a monoclonal mouse anti-biotin antibody (Boehringer Mannheim), and visualized by goat anti-mouse-IgG-Texas Red (Southern Biotechnology, Ass., Inc.).

Products used.

| | |
|---|---|
| 4-hydroxytamoxifen (4HT) | Research Biochemical International |
| sheep anti-digoxigenin fluorescein | Boehringer Maunheim |
| monoclonal mouse anti-biotin antibody | Boehringer Mannheim |
| goat anti-mouse-IgG-Texas Red | Southern Biotechnology Ass., Inc. |
| DAPI | Sigma |
| microscope | Zeiss Axiophot |
| CCD camera | Photometrics |
| IPLab Spectrum (version 3.1) | Signal Analytics |

Example 1

Although peripheral blood CLL cells are non-proliferating, overexpression of cyclin D2 mRNA has been observed in these cells (Blood 85:2870, 1995). In the present study cyclin D2 protein levels are examined to determine whether the increase in cyclin D2 mRNA in CLL can be attributed to gene amplification. By Western blot analysis, cyclin D2 protein was undetectable in normal B or cord blood CD5+/CD19+ cells, whereas the protein was detectable in 12 of 14 CLL patients, with the highest levels being observed in patients with advanced Rai staging. In addition, degradation of the protein was observed, with the extent of protein turnover being greatest in cells with the highest levels of cyclin D2. Immunohistochemistry showed sub-populations of cells with elevated cyclin D2. Cyclin D2 mRNA levels were increased in 12 of 14 CLL patients, when compared with normal B cells. CLL cells have been examined by dispersed cell assay (DCA) (12 patients) and fluorescent in situ hybridization (FISH) (5 patients) to asses gene copy number. An increase in cyclin D2 hybridization signals was detected with both techniques and multiple cyclin D2 signals were observed by FISH in all patients studied. This was not observed with a control gene (cyclin C). Ongoing studies are assessing whether the multiple signals are related to chromosomal or extrachromosomal gene amplification or to the presence of trisomy 12. Thus, cyclin D2 is overexpressed at the RNA and protein levels in most patients with CLL and preliminary studies indicate that this can be related to gene amplification.

The cyclin D2 gene is amplified in all CLL cells, primarily as a result of the presence of multiple cyclin D2 containing Ees. These Ees can contain other genes, apart from cyclin D2, and can independently increase in size, divide and become incorporated back into chromosomes. The cyclin D2 mRNA can be derived from all these sites of amplified cyclin D2.

Overexpression of cyclin D2 in CD19+/CD5+ cells can cause a block at a specific window of B cell differentiation, and cells can accumulate in this window through defects in apoptosis. Cyclin D2 overexpression in these cells can then cause genomic instability leading to specific genomic changes which lead to tumor progression and transformation.

To analyse the size, structures and replicative/transcriptional potentials of the cyclin D2 containing extrachromosomal elements (Ees) in CLL cells tests were conducted to determine whether they contain other genes in addition to cyclin D2.

Tests were conducted to assess the functional activity of cyclin D2 in CLL cells and to determine whether overexpression of cyclin D2 in normal B cells leads to enhanced cellular proliferation, changes in genome stability and enhanced cell survival.

Samples are obtained by Dr. Johnston from CLL patients followed at the Manitoba Cancer Foundation. The patients are staged using the Rai classification (Table 3) and their initial doubling time calculated, as previously described (Montserrat, et al., 1986). Patients are only studied if they had no treatment or have been off all chemotherapy for >1 month.

Isolation of CLL and mouse B cells. The leukemia cells are isolated from marrow and peripheral blood using a Ficoll-Hypaque gradient (Johnston, et al., 1997). Monocytes are removed using anti-CD33 antibodies coupled to magnetic beads (Dynabeads), and T cells depleted by sheep red cell resetting (Johnston, et al, 1997). Similarly, anti-B220 antibodies coupled to Dynabeads are used to isolate mouse spleen-derived B lymphocytes.

Combined Protein/FISH Analysis (CPFA). This assay is used to quantitate protein levels and determine gene amplification within the same cells (Fukasawa, et al., 1997.). In this study, the assay is used to demonstrate the cell surface markers characteristic for human CLL cells, namely CD5+ and CD19+ (O'Brien, et al., 1995), and examine the gene copy number of cyclin D2 within the same cells. Using this assay, one can assure that no normal B cells (CD5−/CD19+) or T cells CD5+/CD19−) interfere with the analysis.

Cytogenetics and FISH. CLL metaphases are induced by the phorbol ester TPA (1.6×10–7 m) (Juliusson, et al., 1993) and metaphase spreads are prepared and evaluated as described (Mai, et al., 1986; Fukasawa, et al., 1997), following the separation of normal T and B cells from CLL cells. Gene copy numbers (amplified vs. Single copy gene, e.g. cyclin C) are quantitated using IPLab Spectrum software (version 3.1) (Signal Analytics, USA). Chromosome painting (CedarLane) is performed to determine whether cyclin D2 and/or additional sequences from chromosome 12 are amplified or rearranged and whether these structures are found on extrachromosomal elements (Ees) (76; FIG. 2).

Figure 4B:
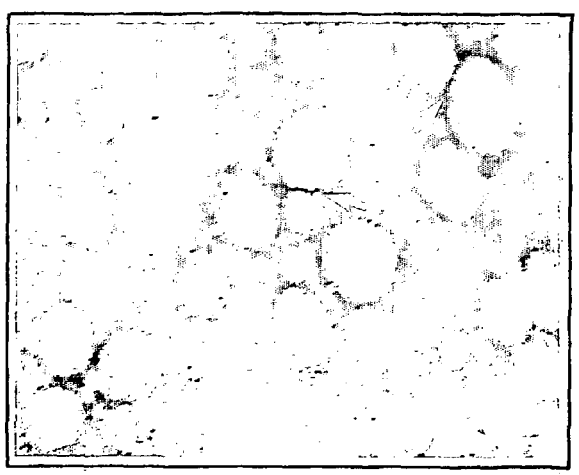
FIG. 4B shows an electron microscopic (EM) analysis of extrachromosomal DNA molecules, this demonstrates the replication intermediates of Ees as schematically shown in FIG. 4A, arrow/arrowheads point to replication intermediates,; the earliest stage of the replicative cycle of Ees is the initiation of a replication bubble (stage 1, small arrowhead), this bubble then grows (stage 2, big arrowhead) and separates from the original bubble which can at this time have initiated another replication cycle (stage 3, arrow); extrachromosomal DNA (1 μ/ml) was dissolved in 30 mM triethanolamine buffer 10 ng of the sample was placed onto a formvar/carbon grid followed by the addition of 2% uranyl acetate, the analysis was carried out with Philips EM 420 TEM microscope; Scale bar: 0.1μ.

Isolation and analysis of Ees. Ees are isolated according to the method of Hirt et al., 1967. To examine their size and replicative potential, they are analyzed by one dimensional and neutral-neutral two dimensional gel electrophoresis respectively (Cohen, et al., 1996; Cohn, et al., 1997). Additionally, they are studied by electron microscopy to examine the presence of replication intermediates (FIG. 4).

Cloning of Ees. Cloning of the Ees into the pcDNA3 vector (INVITROGEN) are performed following isolation of the Ees (see above). Sequencing of the Ees are carried out following PCR amplification (De Cremoux, et al., 1997) of the Ees using Sp6 and T7 (INVITROGEN).

In situ hybridization of pre-mRNA. In situ hybridization of pre-mRNA is used to localize the pre-mRNA transcript to chromosomes, Ees or both. Nascent RNA (pre-mRNA) in situ hybridization and FISH on interphase cells are carried out as previously described (Lawrence, et al., 1989; Wijgerde, et al., 1996; Ashe, et al., 1997). Briefly, 24–50 nucleotide long sequences of the intron-exon boundaries of cyclin D2 are hybridized onto interphase CLL cells. The RNA in situ analysis are followed by FISH as described (Mai, et al., 1996; Fukasawa, et al., 1997) with a cyclin D2 probe (Lukas, et al., 1995) (FIG. 3) and chromosome 12 painting (FIG. 3).

Proliferation, differentiation, apoptosis. Cellular proliferation are determined after pulse-labeling with bromodeoxyuridine (BrdU) (Boechringer Mannheim), apoptosis measured by the TUNEL assay (Fukasawa, et al., 1997) and differentiation of CLL cells measured by IgM production and morphology (Larsson, et al., 1991). Cell cycle analysis is carried out by flow cytometry using Hoechst-staining of total DNA combined with BrdU-incorporation into replicating DNA (Kubbies, et al., 1985; Schindler, et al., 1987).

Abrogation of cyclin D2 protein expression. Cyclin D2 antisense oligonucleotides are synthesized by standard phosphoramidite chemistry and purified by high-performance liquid chromatography. The oligonucleotides (20 mer) are designed according to the OLIGO primer analysis software (version 3.4), which determines the potential dimer formation and self complementary properties as well as the melting temperature and duplex formation (Anazodo, et al., 1996) (see letter). Control oligonucleotides are cyclin D2 sense, single base mutated and scrambled.

Gel retardation analysis. Whole cell extracts and gel retardation studies are carried out as described earlier (Mai, et al., 1994). E2F sites from the DHFR promoter are used in gel retardation studies to determine E2F complex formation (Fry, et al., 1997).

Transfection studies on B cells. Transfection studies on B cells are carried out by electroporation (Zheng, et al., 1996) and immunoprecipitation and Western blotting performed as described (Harlow, et al., 1988).

Amplification of cyclin D2 is a constant feature of CLL, and the size of these amplicons and whether they are primarily extrachromosomal or are reincorporated into specific chromosomes are assessed. In addition, the structure is examined and the replicative/transcriptional potential of the cyclin D2 containing Ees and determine if other genes are also present in these Ees.

Ees from CLL cells are isolated and separated on agarose gels to assess molecular weight ranges. Using this approach, the preliminary studies have indicated a size range from 5 to 25 kb. Gels are then blotted and filters hybridized with a human cyclin D2 cDNA (Lukas, et al., 1995) to assess which DNA bands contain cyclin D2 and to obtain an approximate size distribution of these bands. If additional bands are observed that do not hybridize with the cyclin D2 cDNA, this will suggest the presence of Ees that contains other genes. To confirm this: a) bands which do not hybridize with cyclin D2 are isolated, the DNA cloned and sequenced, and b) DNA purified from the same bands are labeled for FISH and hybridized onto metaphases and interphases from CLL cells. DNA isolated from the same bands are hybridized onto normal B cell metaphases and the loci involved in the formation of these Ees identified by classical cytogenetics and FISH. As the Ees in CLL cells are very small, they are more easily cloned and sequenced than the much larger Ees usually observed in tissue culture.

Ees are digested with a rarely cutting restriction enzyme, e.g., Not I or Xho I, and ligated into pcDNA3, and will then be transformed into *E. coli* (DH5✕). A cloning vector, rather than a cosmid or YAC, has been chosen based on the size of the Ees. Resulting bacterial colonies are replica plated and probed for cyclin D2 to identify colonies with cyclin D2 carrying sequences. The remaining colonies will harbour non-cyclin D2 carrying sequences. Initially the sequence DNA is derived from colonies that hybridize with cyclin D2 cDNA and determine whether the cyclin D2 gene is rearranged, e.g., inverted. If the sequences of more than one cyclin D2 gene is rearranged, e.g., inverted. The number and position of the restriction enzyme sites can be able to determine whether they are in a head-to-head or head-to-tail orientation. Additionally, assessments are made regarding whether other genes, e.g., p27kip1, are present within the cyclin D2-containing Ees and also sequence the non-cyclin D2 containing Ees.

The EM studies have suggested that the Ees in CLL can replicate, and to confirm this the Ees are subjected to two dimensional (2D) gel electropheresis. If replication of cyclin D2-containing Ees is occurring, then replication arcs are visible after specific hybridization for cyclin D2. Similarly, the same blots can be hybridized with non-cyclin D2-containing DNA, purified from non-cyclin D2 hybridizing bands (see 1a), to determine if these Ees are also replicating.

Cyclin D2 mRNA is detectable in CLL (FIG. 6). To determine whether the cyclin D2 mRNA is being transcribed from the Ees, nascent pre-mRNA is carried-out in in situ hybridization followed by FISH (Lawrence, et al., 1989; Wijgerde, et, al., 1996; Ashe, et al., 1997). 24–50 nucleotide long sequences derived from cyclin D2 exon/intron boundaries (Jun, et al., 1997) are used to detect the nascent pre-mRNA. The published exon/intron sequences are for the mouse cyclin D2 gene (Jun, et al., 1997). However, the human cyclin D2 exon/intron boundaries are similar, since the 5' and exon sequences from the mouse and human cyclin D2 genes are homologous (Jun, et al., 1997; Brooks, et al., 1996). If problems are encountered in the hybridization efficiency using these sequence motifs, PCR is used to amplify the human exon/intron boundaries. In in situ hybridization, control samples are processed after RNAseH digestion or in the presence of actinomycin D, which blocks de novo transcription. There is no risk of hybridization of short oligonucleotides to genomic DNA during the in situ RNA hybridization (Lawrence, et al., 1989). To confirm this, FISH analyzes are done with these oligonucleotides in interphases and metaphases of CLL cells. The RNA in situ analysis are followed by FISH with a cyclin D2 probe (Wijgerde, et al., 1996) (FIGS. 1 and 2) and chromosome 12 painting. Localization of the origin of the cyclin D2 pre-mRNA transcript will confirm whether cyclin D2 is being produced by the Ees and/or chromosomal DNA.

Cyclin D2 is overexpressed at the mRNA and protein levels in CLL (FIGS. 6 and 7) but have not yet determined whether cyclin D2 is active. Thus it is determine whether: a) cyclin D2 is associated with CDK4 or CDK6 and able to phosphorylate Rb; b) abrogation of cyclin D2 protein expression in CLL cells influences survival, differentiation and/or cell proliferation, and c) cyclin D2 overexpression on normal B cells effects apoptosis, differentiation and genomic stability.

If cyclin D2 is functional in CLL, it will bind CDK4 or CDK6 and this can lead to the phosphorylation of Rb. Recent studies have shown that p27kip1, an inhibitor of the cyclin E/CDK2, cyclin A/CDK2 and cyclin D/CDK4 complexes (Hirama, et al., 1995; Blain, et al., 1997; Kawamata, et al., 1998; Wang, et al., 1997; Reynisdottir, et al., 1997) can also be overexpressed in CLL (Vrhovac, et al., 1997). Whether cyclin D2 is active can thus depend on the relative levels of specific cyclin/CDK complexes, p27kip1 and/or other CDK inhibitors. In this study the focus is on cyclin D2 activity in CLL cells; the presence of cyclin D2/CDK complexes is determined by co-immunoprecipitations followed by Western blotting and examine the abilities of the complexes to phosphorylate a GST-Rb protein in vitro (Bosc, et al., 1995) can lead to the phosphorylation of Rb. In parallel, the cellular levels of p27kip1 protein are determined. Assessments are also be made regarding whether p27kip1 is associated with the cyclin D2/CDK complexes and correlate this finding with the in vitro kinase activities, as determined above.

Although isolated cyclin D2/CDK complexes can be active, their effects in the cell can depend on the relative amounts of the Rb protein, which has been shown to be low or absent in 18–42% of patients (Neubauer, et al., 1991; Kornblau, et al., 1994). To directly assess this possibility, the dissociation of E2F from Rb is examined by immunoprecipitation and Western blotting and the binding of E2F complexes to E2F sites on the promoters of target genes, e.g., DHFR (Sherr, 1994; Hirama, et al., 1995; Fry, et al., 1997), by gel retardation analysis (Mai, et al., 1994). Apart from the potential pathway through the Rb/E2F pathway, it is possible that cyclin D2 directly regulate transcription and thus cellular function. This speculation is based on the recent report that cyclin D2 represses v-Myb (Ganter, et al., 1998).

To further assess the role of elevated cyclin D2 protein levels in CLL cells, cyclin D2 antisense oligonucleotide studies are conducted with Dr. Jim A. Wright, who has extensive experience with this technology. CLL cells are treated in vitro with the antisense and control olignonucleotides. The readout to document the successful administration of the antisense oligonucleotides can initially be the decreasing levels of cyclin D2 protein in the antisense treated, but not control-treated cells. If successful, cellular proliferation are examined, differentiation and apoptosis are altered by the drop in cyclin D2. To confirm the data that are obtained in these antisense experiments, microinjection studies are conducted using anti-cyclin D2 antibodies (Pharmingen).

The above studies show that cyclin D2 plays a role in proliferation, differentiation or apoptosis, direct assessments of the effect of cyclin D2 overexpression on normal non-cycling B cells are conducted. It has been shown that overexpression of cyclin D2 can prevent differentiation and apoptosis in myeloid cells (Ando, et al., 1993; Kato, et al,. 1993), but the effect in lymphoid cells is not yet known. In addition, assessments regarding whether cyclin D2 overexpression affects genomic stability are also conducted, as has been observed in epithelial cell line with overexpression of cyclin D1 (Zhou, et al., 1996).

Because of the difficulty in obtaining large numbers of normal human B cells, initial examinations of normal spleen-derived mouse B cells are conducted. This shows that 98% of these cells are in $G_0$ and they are thus an appropriate model for the CLL cells. The mouse B cells are transfected or electroporated with a murine cyclin D2 carrying B-cell expression vector (Cµ-driven, pMKµm1; kindly provided by Dr. Konrad Huppi, NIH) and the green fluorescent protein (GFP) (pEGFP-N1, Clontech). This vector has been used to generate transgenic mice. However, if the transfection efficiency is too low, infection of the B cells with Abelson murine leukemia virus with or without the cyclin D2 containing plasmid takes place (Rosenber, et al., 1976). B cells are isolated and the transfected B cells identified due to the expression of the GFP. At different time points the cyclin D2 levels in transfection B cells are measured by Western blot analysis, cell cycle analysis is also carried out and the fraction of apoptotic cells calculated. In parallel, genomic instability are assessed by FISH looking for the typical chromosomal changes that have been identified in CLL. Control cells are transfected with the vector alone.

This study is unique in that it is the first to characterize the formation, structure and significance of Ees in primary tumor cells from patients. The results will provide information as to the genes present in Ees in CLL cells and whether these Ees replicate and transcribe. Furthermore, they will provide insight into the role of cyclin D2 in CLL and normal B cells. Overexpression of cyclin D2 is shown to induce cyclin D2 transfected B cells into SCID mice to determine if the cells are transformed and give rise to B-cell tumors. To ensure the relevance of these studies to human cells, cyclin D2 and/or non-cyclin D2 containing Ees will also be introduced into normal human B cells using an adenoviral vector and their tumorigenicity are assessed in SCID mice (Graham, et al., 1991).

Example 2

Mice. Balb/c mice were obtained from Dentistry (University of Manitoba) and kept according to the international standards of Central Animal Care. All experiments performed were in accordance with the approved animal protocol (95–441). An age group of 406 week old Balb/c mice (20 mice each) received i.p. injections of 0.5 ml pristane (2,6,10,14-tetramethylpentadecane (Sigma)) or LPS (lipopolysaccharide (Sigma)) at 125 µg/ml (20 mice each). At the time points indicated in the text, samples were taken from the peritoneal cavity of the experimental mice. To this end, the mice were anesthesized using avertin (2,2,2-tribrom-ethanol (Aldrich)). 1 g avertin was dissolved in 0.5 ml liquid tertiary amyl alcohol (Aldrich). 0.5 ml of this solution was diluted with 39.5 ml warm (37° C.) phosphate buffered saline (PBS) and used to anesthesize the mice. The average dose per mouse was dependent on the body weight of the animal; a mouse of 20 g received 0.35 ml. After anesthesia, peritoneal cavity cells were collected with 8–10 ml of 37° C. prewarmed sterile culture medium that did not contain fetal calf serum.

Cells directly isolated from the experimental mice were immobilized on microscopic slides using a cytospin centrifuge. Fluorescent immunohistochemistry was carried out using a mouse anti-c-Myc antibody (3C7, reef. 13) at 20 mg per slide, followed by a goat anti-mouse IgG-Texas Red antibody (Southern Biotechnology Associates, Inc., USA) at 10 µg per slide. The fluorescence intensity was quantitated using the Multiprobe 1.1E software (Signal Analytics, USA) (Mai, et al., 1996). One hundred to three hundred cells were evaluated per sample.

Fluorescent in situ hybridization (FISH) was used to determine gene copy numbers on a single cell level. The DHFR probe used for hybridization as well as the hybridization conditions and the image analysis have been described earlier (Mai, 1994; Mai, et al., 1996). The mouse total chromosome 13 paint was purchased from Cambio (CedarLane Laboratories Limited, Hornby, Ontario, Canada). The evaluation of metaphase spreads and interphase nuclei was performed using a Zeiss Axiophot microscope and a CCD camera (Photometrics/Optikon). Image analysis was performed using IPLab Spectrum H-SU2 (Signal Analytics, USA) and Gene Join (Yale University, USA) on a Power Macintosh 8100 computer. 100–150 interphases were evaluated in three independent experiments. Hybridization signals were measured with IPLab Spectrum/Multiprobe (Signal Analytics, USA), using the fine measurement function. Relative fluorescent intensity per pixel (1 pixel=6.8 µm) was used to determine both single copy and amplified fluorescent signals. A signal is classified as amplified if the ratio between the relative fluorescent intensity per pixel of amplified vs. The relative fluorescent intensity per pixel of single copy signals is >2.

Western blot analysis. Peritoneal cavity cells were isolated one week LPS or pristane-treatment. Cells of control, LPS or pristane-treated mice were pooled for further analysis. 100 µg protein was loaded per lane and separated on a 10% SDS-PAGE gel (Mai, et al., 1994; Mai, 1994). Western blots were carried out using the ECL protocol as described (Mai, et al., 1994; Mai, 1994) and the 3C7 anti-c-Myc antibody (Evan, et al., 1985) as primary antibody at 200 ng per blot. The secondary antibody was a peroxidase labeled anti-mouse antibody (Amersham) and was used at 1:20000 dilution. Densitometry was performed using the "box function" of the Sigma gel™ gel analysis program (Jandel, Scientific Software, USA).

Southern blot analysis. Peritoneal cavity cells were isolated one week after LPS or pristane-treatment. The cells of control, LPS or pristane-treated mice (6 mice per group) were pooled for further analysis. DNA was isolated as described (Mai, 1994) and 10 µg DNA was digested with EcoRI (Boehringer Mannheim, Canada) according to the manufacturer's protocol. Blotting, transfer and hybridization were carried out as outlined earlier (Mai, 1994). Equal loading and uniform transfer of the DNA were controlled by ethidium bromide staining. The filter was hybridized with a 1.2 kb PstI-fragment of the hamster DHFR gene (Chang, et al., 1978).

As shown recently, lymphoid and non-lymphoid cell lines amplify the DHFR gene as a result of c-Myc overexpression (Mai, et al,. 1996). Moreover, p53-deficient mice show DHFR gene amplification and c-Myc upregulation within the same cells (Fukasawa, et al., 1997). However, in this latter system, it was not possible to directly assess whether c-Myc overexpression was the cause of DHFR gene amplification. To directly determine whether DHFR gene amplification occurred as a result of c-Myc overexpression in vivo, plasmacytoma (PCT)-susceptible Balb/c mice was examined that were injected i.p. with pristane (Potter, et al., 1992, Materials and Methods). Control Balb/c mice received i.p. injections of LPS (lipopolysaccharide) that elicites the transient activation of B cells concomitant with a transient upregulation of c-Myc protein levels, but does not lead to PCT genesis which requires the constitutive overexpression of c-Myc (Potter, et al., 1992).

Cells directly derived from the peritoneal cavity, the site of PCT diagnosis (Potter, et al., 1992), were analyzed for their c-Myc protein levels by quantitative fluorescent immunohistochemistry (Materials and Methods). Pristane elicited the elevation of c-Myc protein levels. When examined on a single cell level by quantitative fluorescence immunohistochemistry, the induction level of c-Myc protein reached 4- to 10-fold three days post pristane injection and remained elevated for the next four weeks. LPS induced a similar, but transient upregulation of c-Myc protein levels in B lineage cells. Non-treated peritoneal cavity cells exhibited low c-Myc protein levels. When the upregulation of c-Myc was analyzed in the total cell population of the peritoneal cavity by Western blots, the upregulation was visible, however less pronounced, with 2.6- and 1.4-fold induction for LPS vs. pristane-treatments, respectively.

Next examined is the genomic stability of the DHFR gene in the above groups of pristane-treated, LPS-treated and untreated Balb/c mice. Conventional Southern blot analysis did not show chromosomal amplification of the DHFR gene in the total genomic DNA of pristane- or LPS-treated cells isolated from the peritoneal cavity. Similar to previous findings (Mai, et al., 1996), Southern analysis suggested the partial rearrangement of the DHFR locus. This was only observed in pristane-treated mice. Since fluorescent in situ hybridization (FISH) is the most sensitive technique for the detection of genomic instability on a single cell level, being even more sensitive than the PCR (polymerase chain reaction)-based detection of chromosomal aberrations, and since it is therefore becoming the method of choice in clinical studies (Eckschlager, et al., 1996; White, et al., 1997; Afify, et al., 1997), this approach is used to evaluate genomic instability of the DHFR gene in peritoneal cavity cells. An increase in hybridization signals of the DHFR gene was observed after a single i.p. injection of pristane. LPS did not lead to an increase in fluorescent hybridization signals of the DHFR gene.

The relative fluorescent intensities of DHFR signals were measured using IPLab Spectrum software (Materials and Methods). The mean increase in DHFR signals in pristane-treated mice was 4.3-fold and affected 20–60% of all peritoneal cavity cells. The distribution of the signals suggested the presence of extrachromosomal elements carrying the DHFR gene.

Next, a test is run regarding whether the increase in DHFR hybridization signals was due to the increase in chromosome 13, the carrier of the mouse DHFR gene, or due to DHFR gene amplification. To distinguish between those two possibilities, a total chromosome 13-specific paint (Materials and Methods) is used and painted the peritoneal cavity interphase cells. In almost all interphases analyzed (>97%), chromosome 13 was present in two copies. Trisomy of chromosome 13 was observed din the remaining cells (<3%). The chromosome 13 paint also stained extrachromosomal elements that hybridized with DHFR confirming the data.

In the present report, pristane-treated Balb/c mice are shown to display an increase in c-Myc protein levels and DHFR hybridization signals as determined by FISH. In the majority of the analyzed cells (>97%), the latter can be attributed to DHFR gene amplification, with >97% of all cells exhiting two copies of chromosome 13. <3% of all cells exhibited three copies of chromosome 13.

The above in vivo findings allow two conclusions: i) the DHFR gene is a molecular marker of c-Myc-dependent genomic instability following pristane-induction in plasmacytoma-susceptible mice in vivo, and ii) one can speculate that the amplification of the DHFR gene can be functionally important in c-Myc-induced genomic instability and neoplasia. While the first alternative is well documented in cell lines that overexpress c-Myc (Denis, et al., 1991; Mai, 1994; Mai,et al., 1996) and now also in the c-Myc overexpression-dependent mouse plasmacytoma, the second alternative remains hypothetical. As shown earlier, DHFR gene amplification and DHFR enzyme overexpression coincide (Luecke-Huhle, et al., 1996). One can therefore speculate that the amplification and overexpression of the DHFR enzyme, which is a key enzyme of folate metabolism, will lead to changes in the deoxynucleotide pool sizes, especially in the level of deoxythymidine triphosphate (dTTP). Changes in the nucleotide pool enhance mutation frequencies (Kunz, et al., 1994). Thus, DHFR overexpression can account in part for the accelerated acquisition of mutations and of further genomic instability. In addition, cellular proliferation and thus the statistically increased chance to generate a malignant clone can be enhanced due to DHFR overexpression. Interestingly, the potential to amplify the DHFR gene as well as the levels of DHFR gene amplification observed correlated with the metastatic potential in a rat tumor model (Luecke-Huhle, 1994).

In conclusion, the findings presented in this report confirm the previous in vitro data on c-Myc-dependent DHFR gene amplification in non-lymphoid and lymphoid cell lines of mouse, hamster, rat and human (Mai, 1994; Mai, et al., 1996) and show for the first time c-Myc-dependent DHFR gene amplification in vivo.

Example 3

Cell lines and tissue culture. Human brest ductal adenocarcinoma T47D and mouse B lymphoma WEH1 231, were obtained from the American Type Culture Collection, Rockville, Md. Mouse plasmacytomas, MOPC 265 and MOPC 460D, the human colorectal carcinoma line, COLO320HSR, and primary human fibroblasts, GL30/92T, have been previously described (Jaffe et al., 1969; Mai et al., 1996; Mushinski, 1988). The spectrum of mouse B-lymphocytic cells lines has been presented in detail earlier (Mushinski et al., 1987). Cells were propagated in RPMI 1640 (Biofluids, Inc., Rockville, Md.) supplemented with 10% heat-inactivated (30 minutes, 56° C.) fetal bovine serum (Gibco/BRL, Germantown, Md.), 2 mM glutamine, penicillin and streptomycin. Culture media for B-lymphoid cell lines also contained 5×10–5 M 2-mercaptoethanol. In vitro line of mouse pre-B lymphocytes is generated by transformation of BALB/c bone marrow cells with A-MuLV (Rosenberg and Bltimore, 1976). These cells were subsequently transfected with pLXSN-bcl-2, a mouse bcl-2-expressing vector (Gurfinckel, et al. 1987), and pBabePuroMyc-ERTM, an expression vector (Littlewood et al., 1995) with which the human MYC protein can be activated by 100 nM 4-hydroxytamoxifen (4HT, Research Biochemicals International, Natick, Mass.). Also produced is a line of mouse fibroblasts in which MYC is upregulated by 4HT due to stable transfection of pBabePuroMyc-ERTM into y2 cells (Mann, et al., 1983).

Cloning and sequencing of mouse cyclin D2 cDNA and 5' genomic flank A cDNA library of the mouse pre-B cell, 18–81, in lambda ZAP-2, was screened under relaxed conditions with Cyl1 (Matsushime et al., 1991), a partial cDNA for murine cyclin D1, from Dr. Charles Sherr. Several clones that encoded mouse cyclin D2 were isolated, rescued as pBlueScript clones, characterized and sequenced. A probe derived from the clone with the longest (1255 bp) insert was sequenced and found to have a coding region identical to the mouse cyclin D2 cDNAs in the literature (Kiyokawa et al., 1992). This probe was used to screen a partial EcoRI library of BALB/c liver DNA in EMBL-4 arms, from Drs. Linda Byrd and Konrad Huppi. One positive clone that contained a 17.1-kb insert was isolated, purified and digested to completion with EcoRI. Only one of the 3 EcoRI fragments that were generated from 2 internal EcoRI sites, a 5.4-kb fragment, hybridized with the 5' end of the cyclin D2 cDNA probe, and it was subcloned into pBlueScript for further study. Partial sequencing of this fragment revealed that the 3' 505 base pairs were identical to the 5' portion of the cyclin D2 cDNA and that of Kiyokawa et al. (1992). The 3' 194 base pairs contained the AUG and an open reading frame, and the adjacent 301 upstream base pairs contained the 5' untranslated sequence of the cDNA. The remainder was considered 5' flank in which regulatory motifs might be expected. The complete sequence of the mouse 5' flank is being generated and are reported elsewhere.

Electrophoretic mobility shift and supershift assays. Whole cell extracts were prepared as described (Mai and Jalava, 1994) from WEHI 231 mouse B-lymphoma cells and the mouse plasmacytomas MOPC 265 and MOPC 460D. All mobility shift reactions as well as supershifts were performed at room temperature. If not indicated differently, 5 mg of cellular protein were incubated for 5 minutes with 1 mg of non-specific competitor DNA (salmon sperm DNA) followed by a 30-minute incubation with 0.3 ng 32P-end-labeled oligonucleotides E1, E2, E3, and y (FIG. 9), in low salt buffer (10 mM HEPES-NaOH, pH 7.9, 60 mM KCl, 1 mM EDTA, 1 mM DTT, 1 mM protease inhibitor AEBSF (Calbiochem, San Diego, Calif.), and 4% Ficoll 400. Gell electrophoresis was performed on 5% non-denaturing polyacrylamide gels in 22.5 mM Tris-borate/0.5 mM EDTA (Sambrook et al., 1986) at 8V for 4 hours. The gels were dried and subjected to autoradiography. Supershift analyses were carried out as follows: 5 mg of whole cell extracts were incubated with 1 mg non-specific competitor DNA (salmon sperm DNA) in low salt buffer (see above). Thereafter, antibodies were added at the concentrations indicated below for 30 minutes at room temperature prior to the addition of 32P-end-labeled oligonucleotides. Gel electrophoresis was performed as above. All antibodies were purchased from Santa Cruz Biotechnology Inc., Santa Cruz, Calif., except the monoclonal anti-MAX antibody, which was obtained from Dr. Achim Wenzel, Deutsches Krebsforschungszentrum, Heidelberg, Germany and the anti-c-MYC polyclonal antibody and antiserum, which were kind gifts from Dr. U. Deutschel, Basel Institute for Immunology, Basel, Switzerland. Purified antibodies were used at 100 ng per reaction; the polyclonal anti-c-MYC antiserum and the respective pre-immune serum at 1 ml per reaction.

Assays for genomic instability and gene amplification. Gene dosage was examined using Southern blot analysis (Southern et al., 1975) and fluorescent in situ hybridization (FISH) of metaphase chromosomes (Mai et al., 1995). Evaluation of metaphase spreads and interphase nuclei was performed using a Zeiss Axiophot microscope and a CCD camera (Optikon/Photometrics). 100–500 metaphases and interphases were evaluated in each of three independent experiments. Extrachromosomal fluorescent signals were considered specific when they also stained with 4', 6' diamidino-2-phenylindole (DAPI) (1 mg/ml) or propidium iodide (PI) (1 mg/ml) (Mai et al., 1996).

RNA isolation and northern blotting. Total RNA or Poly (A)+RNA was isolated from cells as previously reported (Mushinski, et al., 1987). 5 mg of Poly(A)+RNA or 15 mg of total RNA were fractionated on a 1% agarose gel containing formaldehyde. The RNA was transferred to a HybondN membrane (Amersham, Arlington Heights, Ill.) by capillary blotting and hybridized with 32P-labeled cDNA probes as indicated in the figure legends. Radioactive labeling was performed with the Nick Translation System (GIBCO/BRL, Germantown, Md.) according to the manufacturer's protocol. The membranes were hybridized overnight with 3×106 dpm/ml probe, washed with 0.1×SSC, 0.1% SDS at 20° C. and exposed to X-ray film overnight. For sequential hybridization of the same blot with different probes, membranes were stripped with boiling water.

Probes. A 700-bp PstI-fragment of the mouse cyclin D2 cDNA was used to probe Southern and northern blots, and the genomic clone was used as a probe for FISH. A similar strategy was used to isolate cDNAs for mouse cyclins D1 and D3 (Hamel and Hanley-Hyde, 1997, generous gifts from Paul Hamel, University of Toronto). The human cyclin D2 cDNA was from Gordon Peters. It was used as a 1.2-kb NotI-XhoI-fragment. The ribonucleotide reductase R1 (RNR1) probe was a 1.5-kb BamHI fragment of mouse RNR1 cDNA (Thelander and Berg, 1986). The cDNA clone pMc-myc54 (Stanton et al., 1983) for mouse c-Myc was from Kenneth B. Marcu, from which a 0.6-kb Sst 1-Hind III fragment was used as an exons2+3 probe for the Myc sequences expressed in pBabePuroMyc-ERTM (Littlewood et al., 1995). Mouse cyclins C and E probes were gifts of Steven Reed. The cDNA for the "housekeeping gene" glyceraldehyde phosphate dehydrogenase (GAPDH) was from Dr. Marc Piechaczyk (Fort et al., 1993).

Western blotting. Western blots were performed on lysates of pre-B cell cultures as previously described (Mischak et al., 1993) except that protein concentration was determined using the BCA Protein Assay (Pierce), and 10 mg were loaded per lane. The immunoreactive bands were recognized by the ECL Western blotting detection system (Amersham, Arlington Heights, Ill.). The anti-cyclin D2 (M-20) was purchased from Santa Cruz Biotechnology (Santa Cruz, Calif.). The anti-actin (clone AC-40) was from Sigma ImmunoChemicals (St. Louis, Mo.). The HRP-Goat anti-Rabbit IgG and HRP-Goat anti-Mouse IgG and IgM were purchased from Axell (Westbury, N.Y.).

Figure 8:
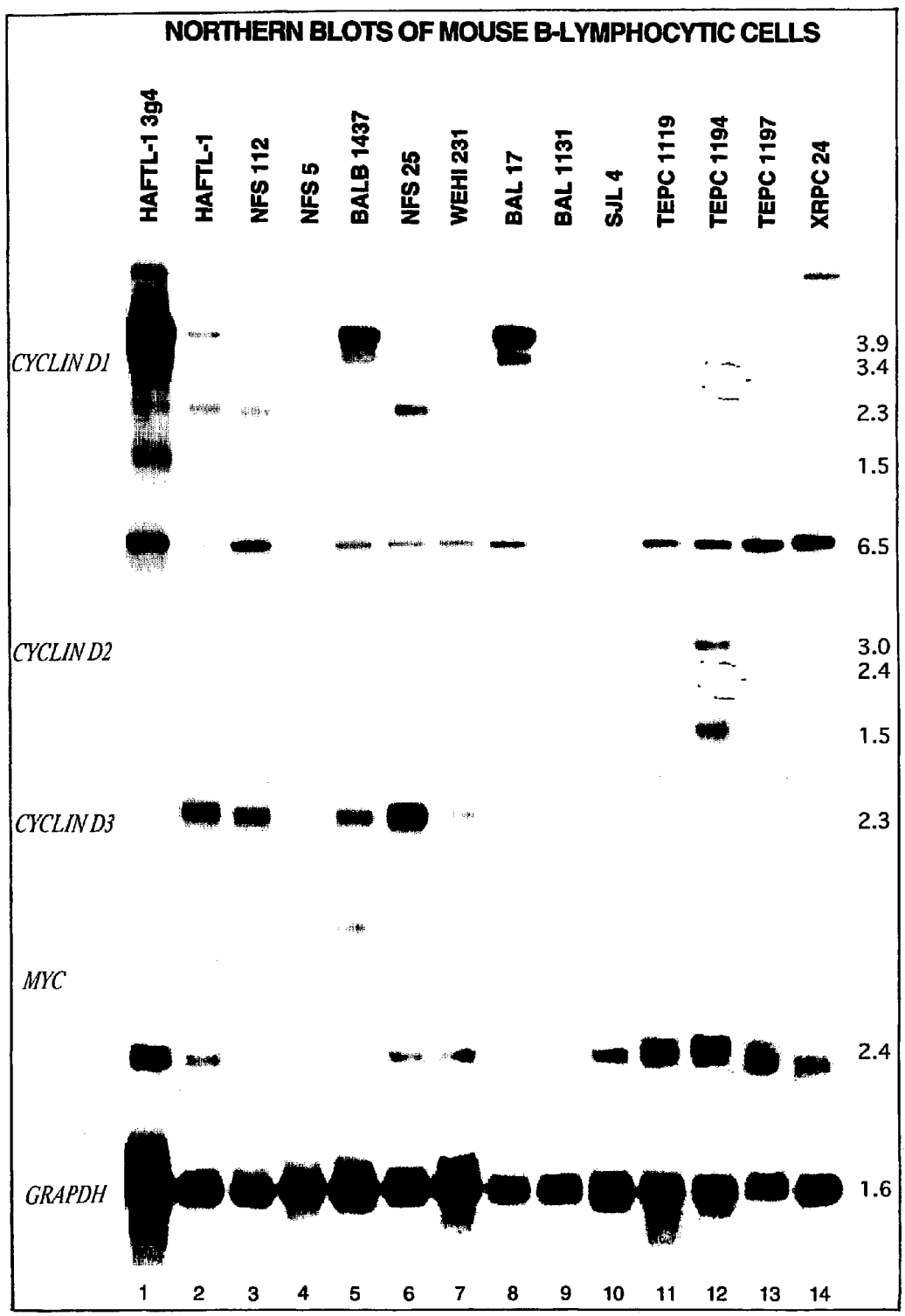
FIG. 8 shows cyclin expression in mouse B-lymphocytic tumors; Poly(A)+RNAs (5 μg) from a series of mouse B-lymphocytic cell lines (Mushinski et al., 1988) are arranged from left-to-right in increasing degree of maturation, HAFTL-1 3g4 and HAFTL-1 are 2 related clones of pro-B lymphocytes, the former having more myeloid characteristics than B-cell characteristics; NFS 112, NFS 5 and BALB 1437 are pre-B cell lines; NFS 25, WEHI 231, BAL 17 and BAL 1131 are mature B-cell lines, SJL 4 is a plasmablastic line; and TEPC 1119, TEPC 1194, TEPC 1197 and SRPC 24 are plasmacytoma lines; the blot was hybridized first with cyclin D2 cDNA and then sequentially with the other hybridization probes indicated along the left margin, following stripping, sizes of major hybridizing bands are indicated on the right.

Northern blot analysis of cyclin D2 expression in murine B-lymphocytic lines with different degrees of B-cell maturation. FIG. 8 shows a blot of poly(A)+ RNA from a series of mouse B-cell lymphoma cell lines of increasing maturation from left to right (Mushinski et al., 1987). When normalized to the GAPDH control hybridization signals, the highest level of expression of the predominant cyclin D2 mRNA (6.5-kb) was seen in the four plasmacytomas (lanes 11–14). In addition, several smaller cyclin D2 mRNAs are prominent, chiefly in these four lanes. These four lanes are the B cells with the highest Myc mRNA content. This blot was stripped and rehybridized with other murine cyclin D probes. The cyclin D3 probe revealed strong 2.3-kb bands in 4 cell lines of early B lymphocytes, but barely detectable levels in plasmacytomas. The cyclin D1 probe showed a very strong 3.8-kb band in the myeloid-pro-B line in lane 1, strong bands in 2 B-cell lines, lanes 5 and 8, but very low levels in the remaining RNA samples. Cyclin E transcripts were virtually undetectable. This pattern of high levels of Myc and cyclin D2 mRNA was also seen in Northern blots of RNA from 45 additional plasmacytomas that included tumors with t(12;15) and t(6;15) translocations and tumors without translocations but with Myc upregulation due to stable integration of Myc-expressing recombinant retroviruses (Mushinski, 1988).

Figure 9:
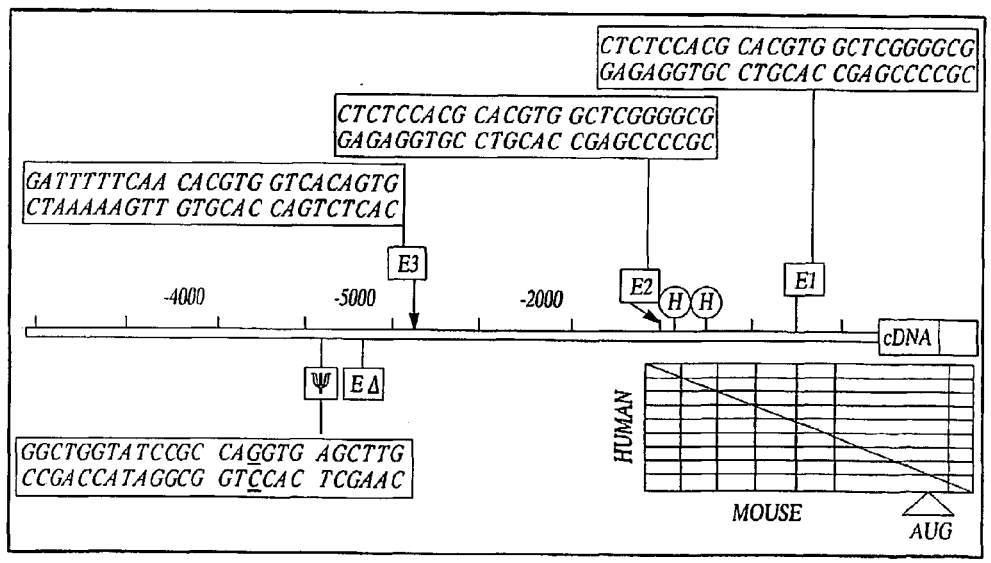
FIG. 9 shows EMS motifs in mouse cyclin D2 5' flank, exon 1 is shown as a box, with the open reding frame shown in black, the mouse 5'flank is indicated by a line to the left, positions of E-box motifs E1, E2, E3, and E4 and y are indicated; sequences of the oligonucleotides that surround E1, E2, E3 and y and which were used for mobility-shift experiments are shown, the portion of the human 5' flank that has been sequenced is indicated by a line of double thickness, a dot-matrix plot of identical bases in the mouse and human 5' flanks is also included; H indicates the positions of the two CACGTG motifs present in the first 1624 5' of exon 1 in the human cyclin D2 gene (Brooks et al., 1996)

The 5' flanking region of the cyclin D2 gene has several CACGTG-motifs that bind c-MYC/MAX. Partial sequencing of the 5' flank revealed four CACGTG motifs, putative "EMS (E-box MYC Sites)" (E1–E4) at positions −867, −1487, −2988 and −3201 from the translation start site, as well as a variant motif, CAGGTG (y) at position −3475. The positions and adjacent sequence of three of the EMS motifs and y are indicated in FIG. 9. A dot-matrix display shows bases that are identical in mouse cyclin D2 5' flank and the published 1624 bases upstream of the human AUG translation start site in the human cyclin D2 gene (Brooks et al., 1996), indicating a strong similarity between the mouse and human 5' flanks. Note that the 5' flank of the human cyclin D2 gene also contains at least two cacgtg motifs. These findings prompted analysis of three of the EMS motifs in the 5' flank of mouse cyclin D2 for their ability to bind MYC/MAX (Blackwood and Eisenman 1991), and to study whether the cyclin D2 locus can be amplified, overexpressed or both, under conditions of c-Myc overexpression.

Figure 10:
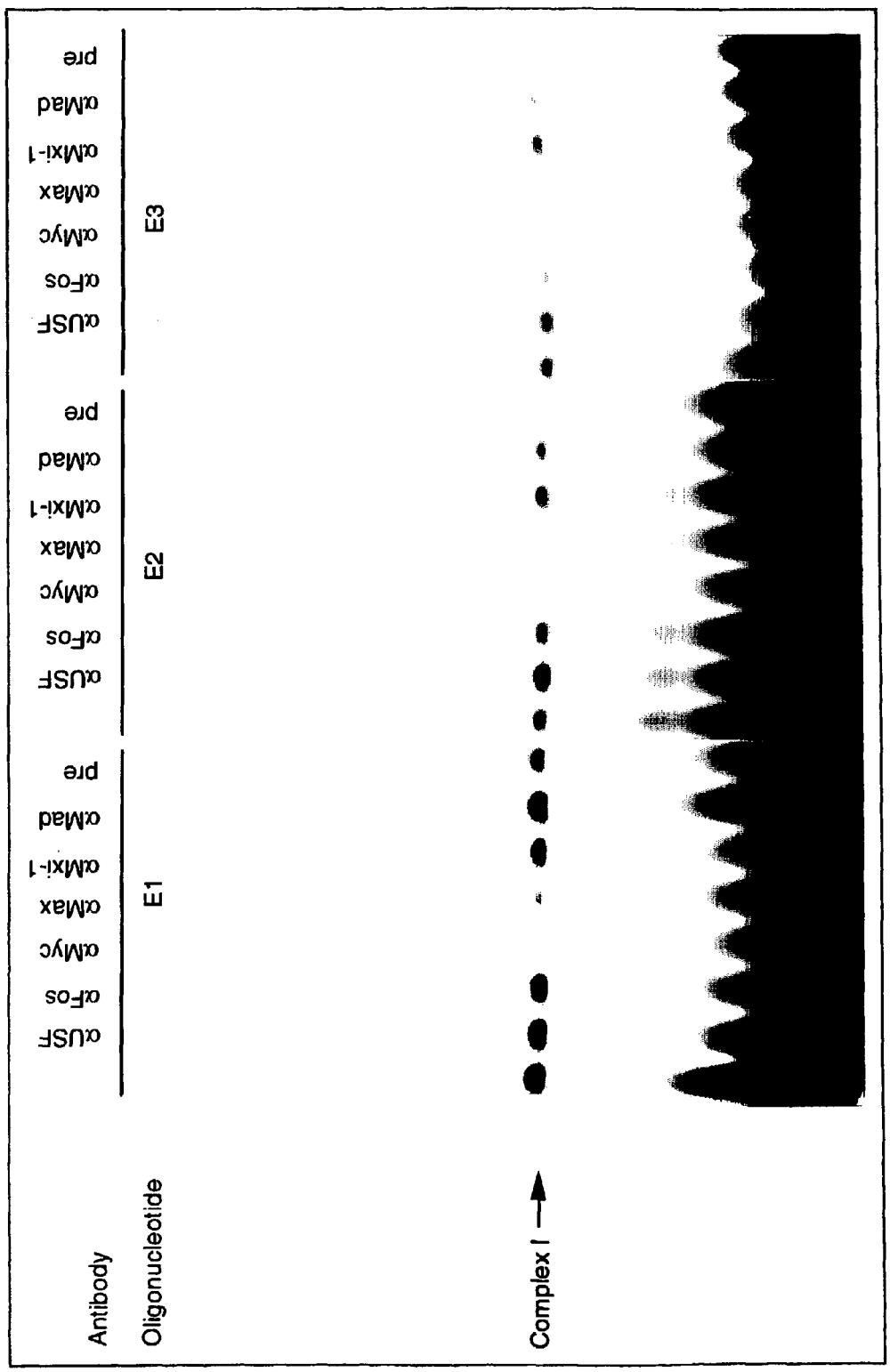
FIG. 10 shows mobility "super-shift" analysis using E1, E2, and E3 olignucleotides, 5 mg whole cell extracts of plasmacytoma MOPC 265 cells were incubated with the indicated antibodies or pre-immune serum (Pre) followed by the 32P-end-labeled oligonucleotides E1–E3 (FIG. 8); 1 mg of non-specific competitor DNA was used per reaction, the arrow points to the specific complex that does not form with bacterial protein alone; "Supershifted" bands appear at the top of the anti-MYC and anti-MAX lanes, non-specific high-molecular weight bands appear in all lanes that use oligonucleotide E2, the antibody concentrations are indicated in Materials and Methods.

Oligonucleotides containing four of the above-mentioned five E boxes were chosen for the mobility-shift analyses: oligonucleotides E1–E3 (EMS motifs 1–3) and y (the variant motif). Purified MYC and MAX bound to E1–E3 but not y. In "super-shift" experiments, the DNA-protein complex I was found to contain both MYC and MAX in logarithmically growing plasmacytoma MOPC 265 cells (FIG. 10). Under these conditions, antibodies directed against c-Fos, Mad, Mxi-1 or USF, an unrelated E-box-binding protein, did not disrupt or supershift complex I, whereas antibodies directed against MYC and MAX did. These data suggested that, under proliferative conditions, MYC and MAX were present in plasmacytoma cells, bound to canonical EMS motifs, and appeared as complex I in mobility shifts and supershifts.

Figure 11A:
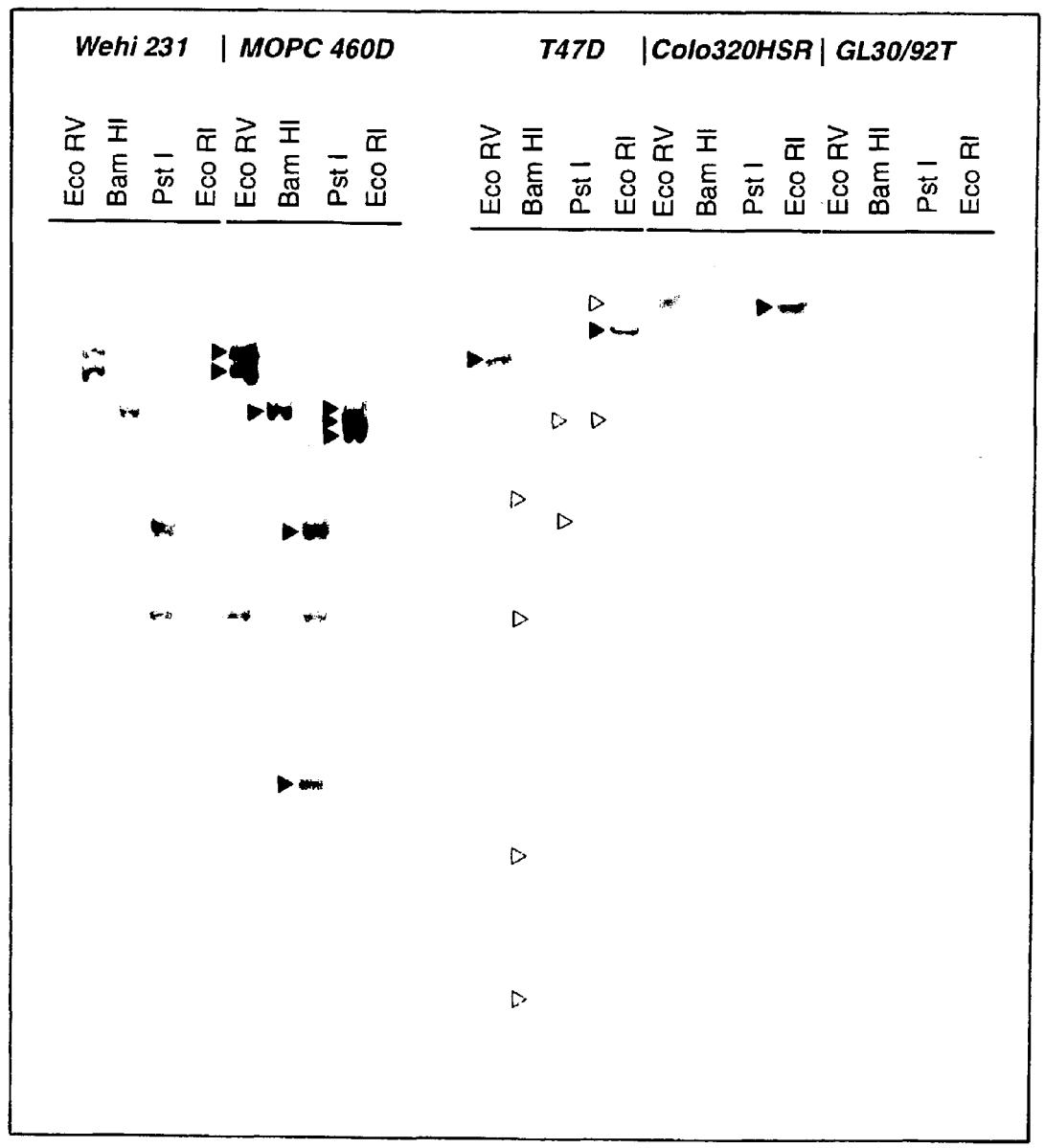
FIG. 11 shows Southern blot analyses of mouse and human cell lines hybridized with murine and human cyclin D2 cDNA probes, as indicated (panel A), mouse lines: WEHI 231 B-cell lymphoma (low MYC) and MOPC 460D plasmacytoma (high MYC); Human lines: GL30/92T primary fibroblasts (low MYC), T47D brest carcinoma cells (high MYC), and COLO320HSR colorectal carcinoma cells (very high MYC); digests were carried out with the enzymes indicated. 10 mg DNA were loaded per lane, equal amounts of DNA were loaded as confirmed by rehybridization of the filters with the mouse ribonucleotide reductase subunit 1 (RNR1) or the human cyclin C genes (panel B); filled arrowheads point to amplified cyclin D2 bands; empty arrowheads indicate lost bands that suggest another form of genomic instability in this tumor.
Figure 11B:
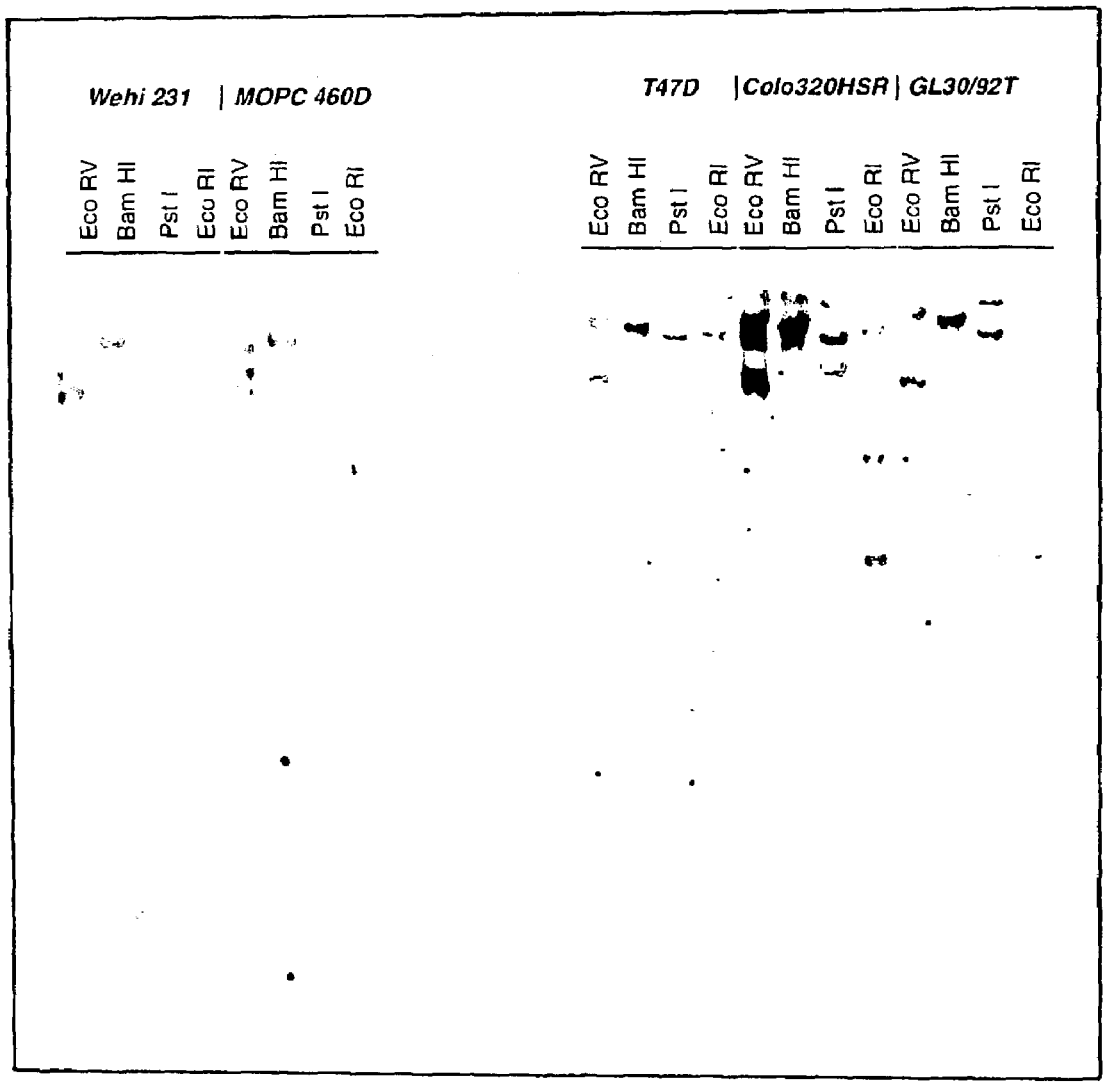
Figure 12A:
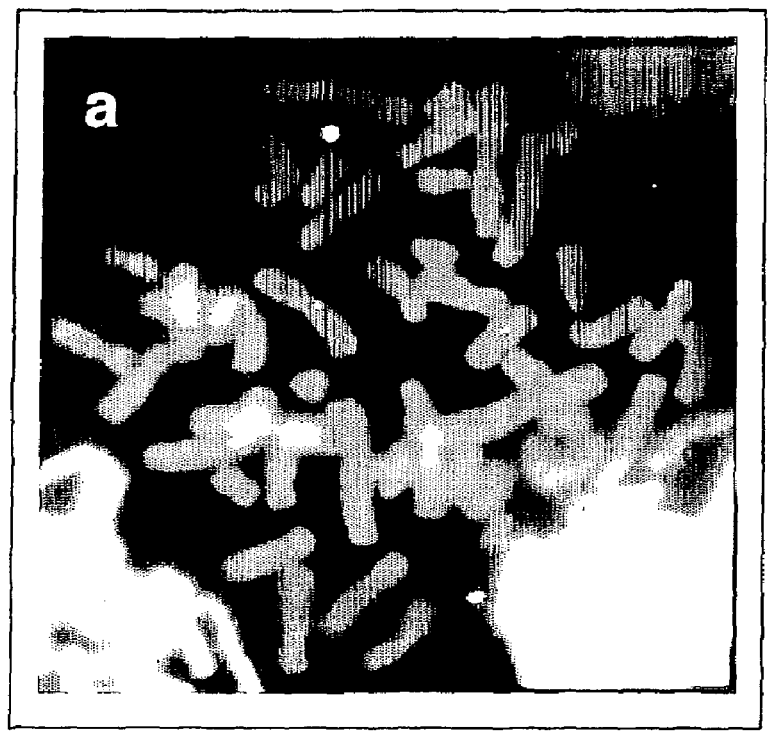
FIG. 12 shows fluorescent in situ hybridization (FISH) studies with a cyclin D2 probe and detection with FITC-labeled anti-digoxigenin antibody; A. COLO320HSR metaphase chromosomes stained with PI (human cyclin D2 cDNA hybridization is seen as fluorescing spots or dark dots); B. MOPC 460 metaphase chromosomes stained with PI (mouse cyclin D2 genomic DNA hybridization is seen as fluorescing spots or dark dots); the arrows point to paired dark dots that indicate the position of the cyclin D2 locus, single dots seen elsewhere in the spread are interpreted as ECEs that randomly reintegrated on other chromosomes; C and D. Metaphase chromosomes from mouse pre-B lymphoma cells that bear the 4HT-activatable pBabePuroMyc-ERTM expression vector were hybridized with the 5.4-kb mouse genomic clone of cyclin D2 on a DAPI background; Cells in panel C were not stimulated with 4HT; those in panel D were grown in 100 nM 4HT for 3 days, arrows point to single-copy cyclin D2 in C and to extrachromosomal elements in panels D; E–H. Metaphase chromosomes from y2 fibroblasts hybridized with the 5.40 kb mouse genomic clone of cyclin D2 on a DAPI background; the image in panel E shows a negative control of FISH analysis of 4HT-treated (3 days) y2 chromosomes from cells that have not received the MYC expression vector; Panels F, G and H show metaphase and interphase chromosomes from cells bearing stable integration of the 4HT-activatable pBabePuroMyc-ERTM expression vector; Cells in panel F were not stimulated with 4HT; those in panels G and H were grown in 100 nM 4HT for 3 days.
Figure 12B:
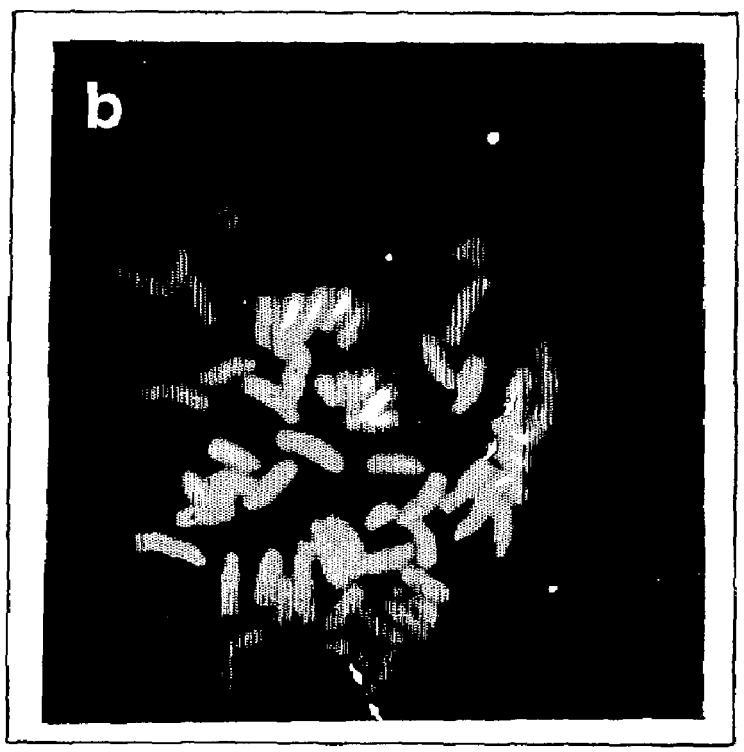
Figure 12C:
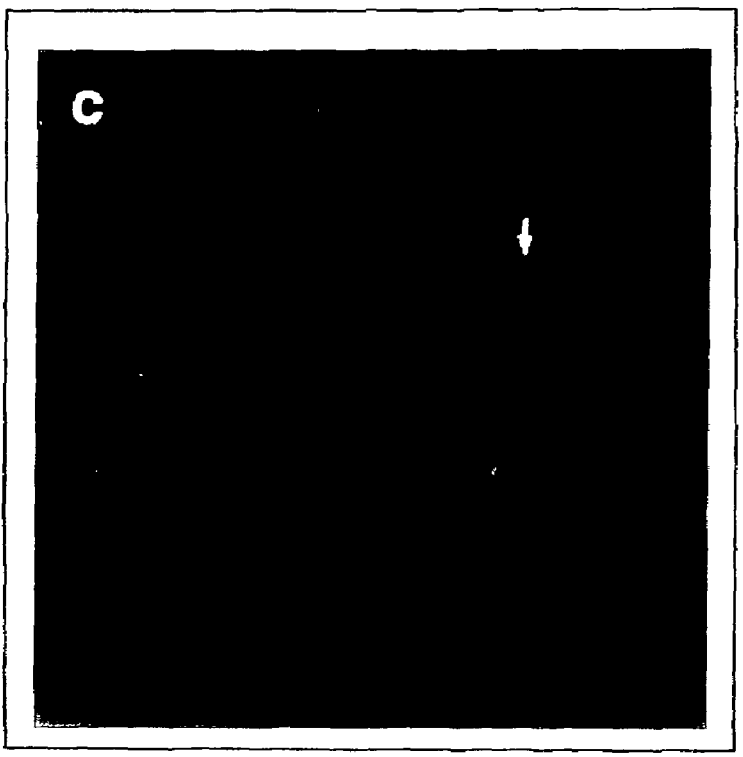
Figure 12D:
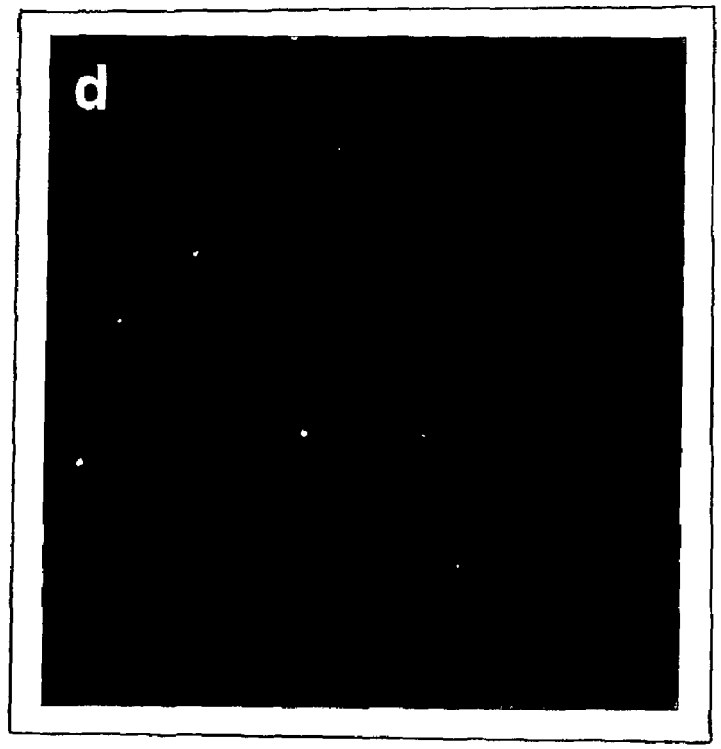
Figure 12E:
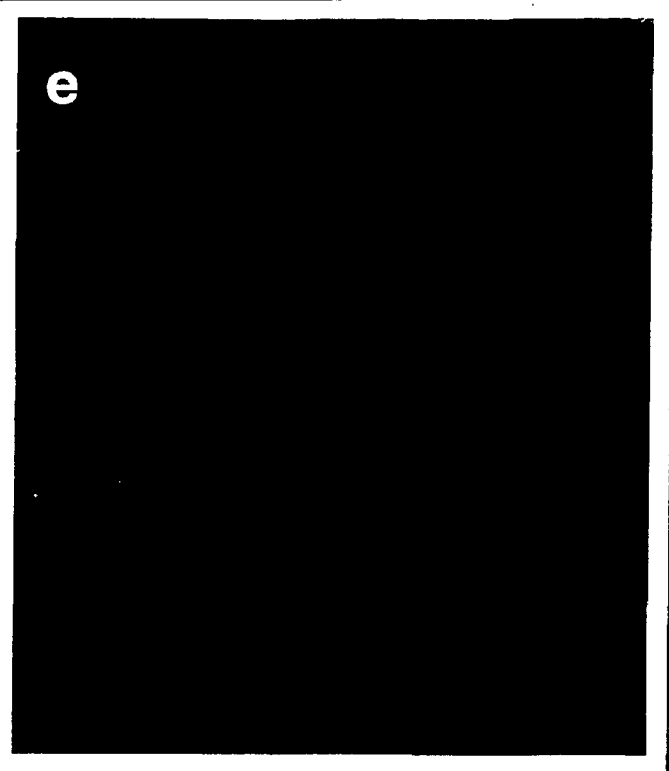
Figure 12F:
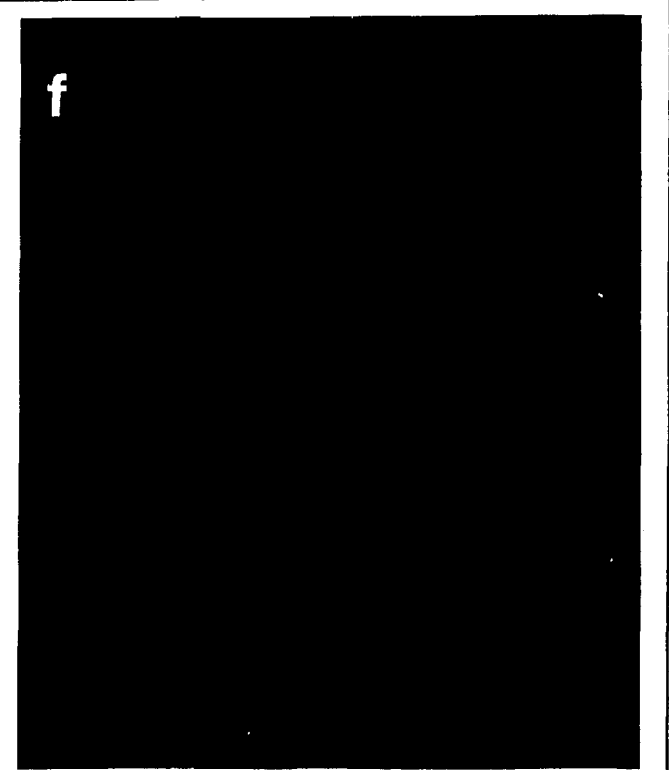
Figure 12G:
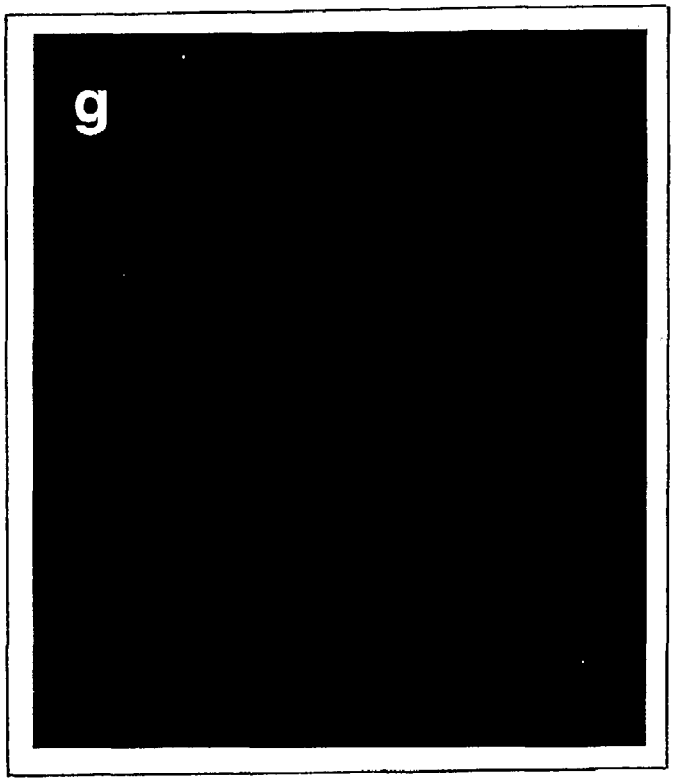
Figure 12H:
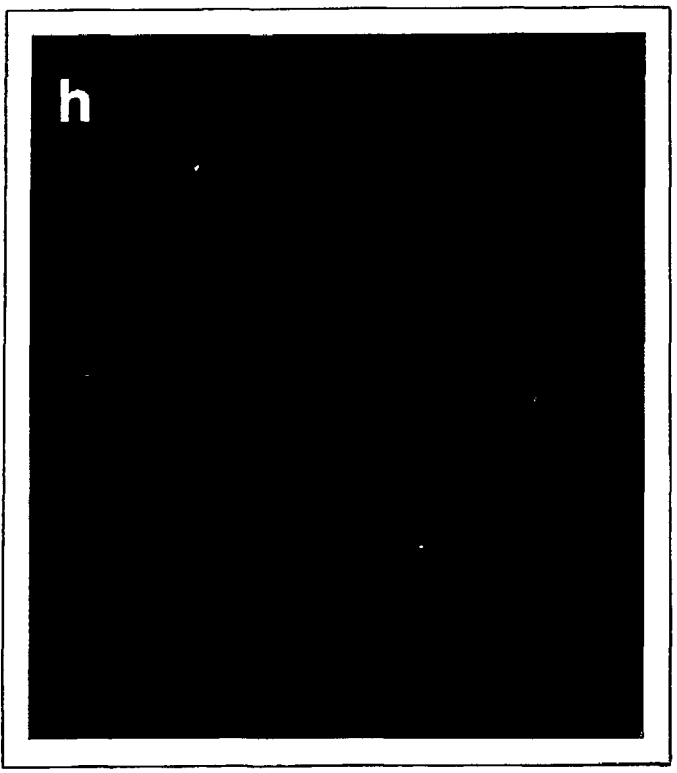

Mouse and human tumors with c-Myc overexpression have Southern blot evidence of amplification of the cyclin D2 locus. The stability of the cyclin D2 locus was characterized in two mouse B-lymphoid lines, MOPC 460D, a plasmacytoma that constitutively overexpresses c-Myc due to Myc/Ig chromosome translocation (Mushinski, 1988), and WEH1 231, a lymphoblastoid tumor with low MYC protein levels (Mai et al., 1996). Southern blot analyses showed that the cyclin D2 gene was amplified in MOPC 460D (FIG. 11, panel A, filled arrowheads), but not in WEH1 231 cells. As in the previous studies, mouse ribonucleotide reductase R1 (RNR1), a gene that is retained as single copy gene irrespective of MYC protein levels, was used as a reference gene (FIG. 11, panel B).

These analyses were extended to human cell lines: the colon carinoma line COLO320HSR, a classic example of c-Myc gene amplification and overexpression (28-fold higher MYC protein levels than GL30/92T primary human fibroblasts); and the breast cancer line T47D, which expresses 11 times higher c-MYC protein levels than GL30/92T (Mai et al., 1996). As in the previous studies, human cyclin C, a gene that is retained as single copy gene irrespective of MYC protein levels, was used as a reference gene. The cyclin C gene was not amplified in any of the human cell lines (FIG. 11, panel B). COLO320HSR and T47D displayed amplified bands of cyclin D2 gene hybridization (FIG. 11, panel A, filled arrowheads), while primary human fibroblasts did not. In T47D, the gene for cyclin D2 is partially deleted as indicated by missing genomic bands in the Southern blot (see open arrowheads in FIG. 11). Such deletions can reflect an additional form of genomic instability of this locus in cells that overexpress Myc.

Cyclin D2 amplification involves the generation of extrachromosomal elements in COLO320HSR and MOPC 460D. DAPI or PI staining of metaphase chromosome spreads of COLO320HSR, a human adenocarcinoma line, showed the presence of extrachromosomal elements (ECEs). Fluorescent in situ hybridization (FISH) showed amplified signals of the cyclin D2 gene on chromosomes and the ECEs (FIG. 12). A similar analysis of the BALB/c plasmactoma MOPC 460D also showed ECEs that contained cyclin D2 sequences (FIG. 12). In agreement with the Southern data (FIG. 11), FISH hybridization of COLO320HSR and MOPC 460D showed neither evidence of amplification of the RNR1gene nor extrachromosomal elements that hybridized with an RNR1 probe.

Induced upregulation of MYC activity in mouse pre-B cells results in cyclin D2 amplification and increased mRNA and protein after three days. A mouse pre-B cell line derived from bone marrow cells by transformation with Abelson-murine leukemia virus (A-MuLV) was stably transfected with pBabePuroMyc-ERTM, an inducible MYC expression vector that is activated by 4HT. After three days of stimulation by 4HT, numerous ECEs can be staining of chromatin and DNA. Several of the ECEs were shown to contain extra copies of the cyclin D2 gene by FISH analysis (FIG. 12). This evidence of genomic instability and of cyclin D2 gene amplification was not seen in the same cells without prolonged tamoxifen stimulation (FIG. 12).

Figure 13A:
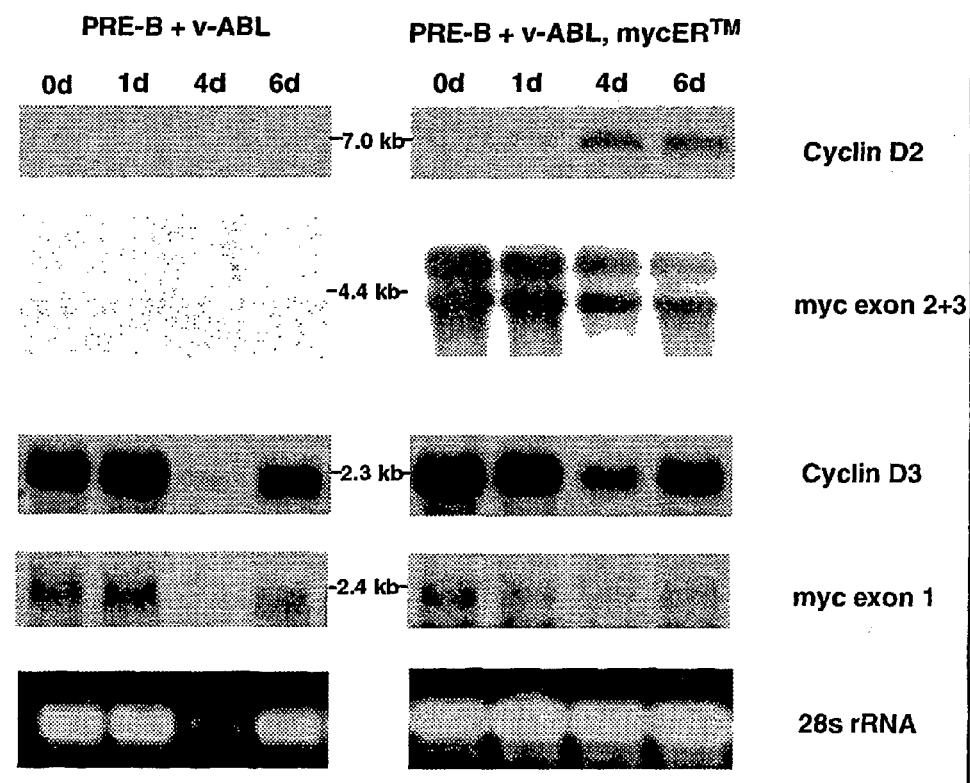
FIG. 13 shows cyclin D2 expression after MYC activation; A. Northern blots of total RNA (15 mg) from bulk cultures of mouse pre-B cells stably transduced with v-Abl (A-MuLV) or with v-Abl plus murine bcl-2 plus pBabePurorMycERTM, both cell lines were treated with 4HT for 0, 1, 4 and 6 days, as indicated, each blot was hybridized first with cyclin D2 cDNA and then sequentially with the other hybridization probes indicated along the right margin following stripping, sizes of major hybridizing bands are indicated between panels, ethidium-bromide-stained 28S ribosomal RNA bands are shown as loading controls; B. Western blots of 10 μg protein per lane, isolated from pre-B cells, with and without pBabePuroMycERTM, after different periods of stimulation with 4-HT, antibody specificity and size of detected protein bands are indicated between panels, actin probing of duplicate blots is shown as loading control; C. Northern analysis of total RNA (conditions as in A) from mouse fibroblasts (y2 cells) with and without stable integration of pBabePuroMyc-ERTM, after different numbers of days of stimulation with 4-HT, GAPDH hybridization is included as a loading control.
Figure 13B:
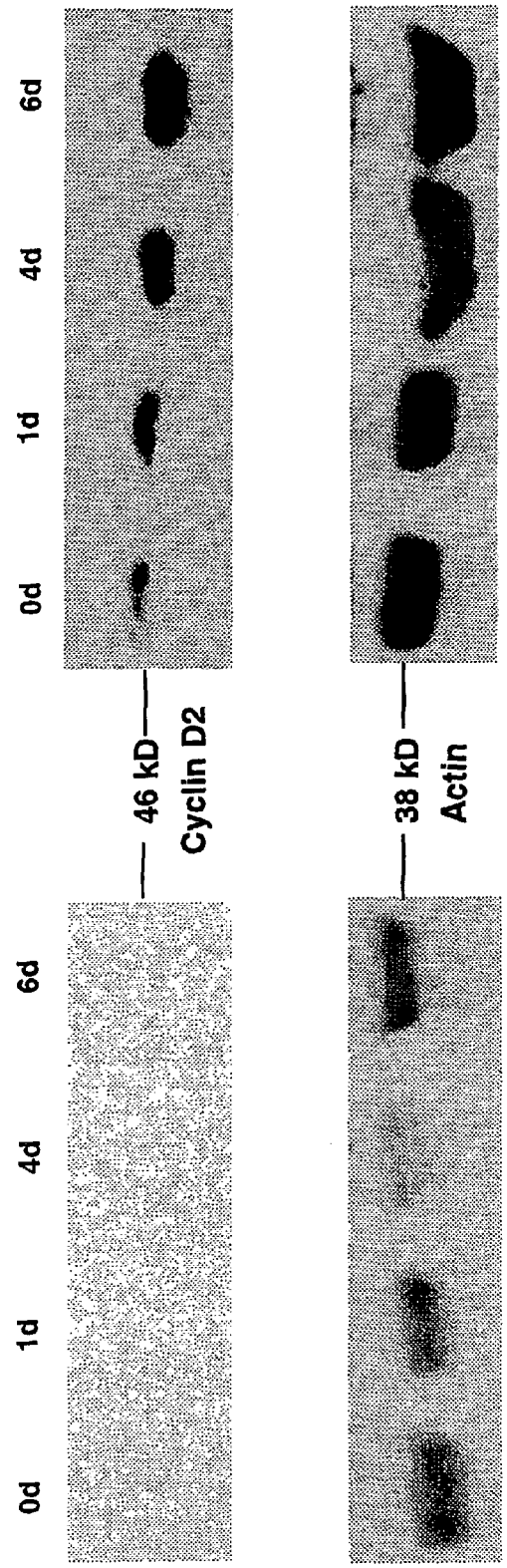
Figure 13C:
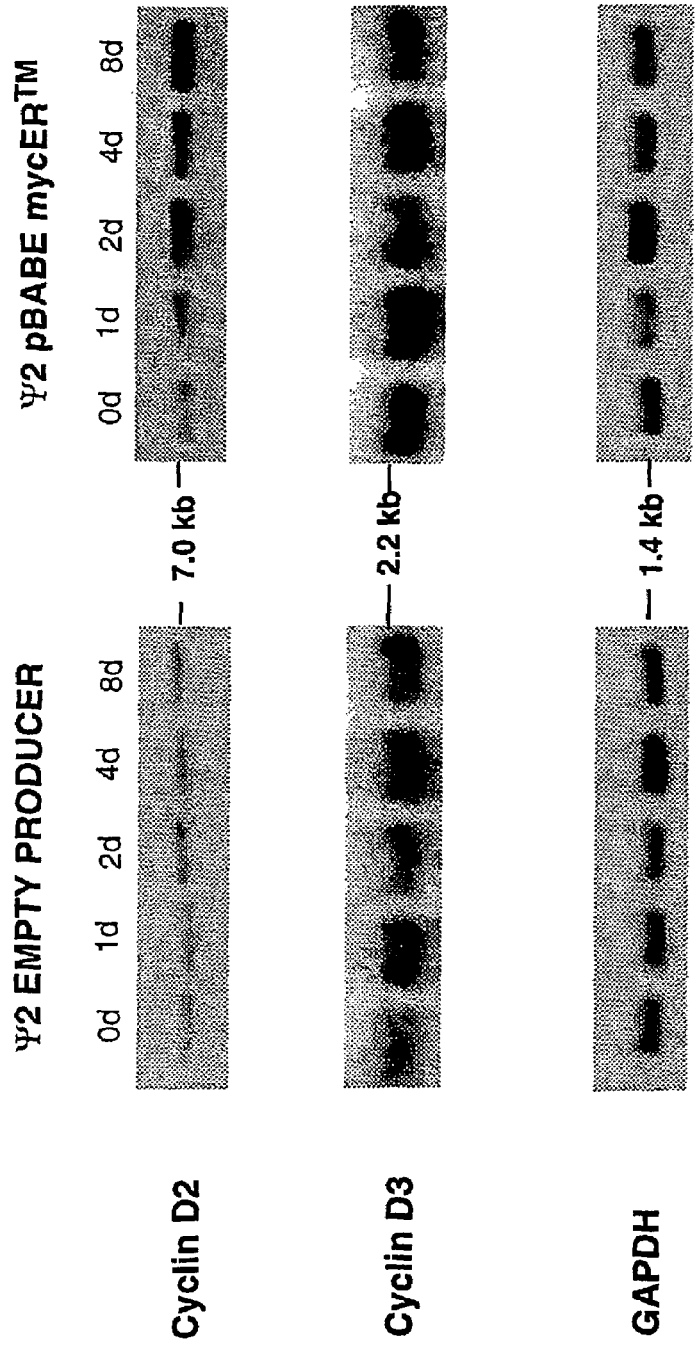
Figure 14:
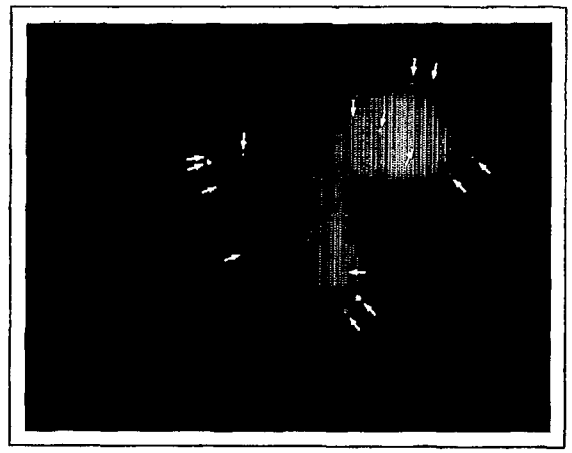
FIG. 14 shows DHFR gene amplification in fully developed plasmacytoma. Arrows point to amplified DHFR sequences as detected by FISH. Nuclei are counterstained with DAPI (4',6'-diamidino-2-phenylindole)

Northern blots were prepared from total RNA from the A-MuLV-transformed pre-B cells before and after stable introduction of pBabePuroMyc-ERTM, and after different periods of stimulation by 4HT. FIG. 13 shows the results of successive hybridizations of this blot with cyclin D2 and other germane probes. Cyclin D2 message expression is clearly elevated after 4 and 6 days of MYC activation by 4HT when compared to the ethidium bromide-stained 28S ribosomal RNA bands in each lane. Transcripts from the retroviral pBabePuroMyc-ERTM in the stably transfected line, shown in the right panels, are detected with a Myc exon 2+3 probe. Endogenous 2.4-kb c-Myc expression was repressed after activation of the exogenous MYC-ER by 4HT, as shown by hybridization with Myc exon 1 probe, since exon 1 is not present in the MYC-ER-containing expression vector. There was no detectable mRNA for cyclin D1, and no significant change in mRNA level of cyclin D3 was seen during the treatment with 4HT.

Western blots of lysates from the 4HT-treated cells described in the preceding paragraph were probed with anti-cyclin D2 antibody and, as a loading control, with anti-actin antibody. As shown in FIG. 13, cyclin D2 protein levels gradually rose in parallel with the levels of cyclin D2 mRNA after MYC activation by 4HT in the pBabePuroMyc-ERTM-containing cells but not in the pre-B cells that lack this vector.

Inducing upregulation of MYC activity in mouse fibroblasts also leads to cyclin D2 amplification and increased cyclin D2 mRNA. A mouse fibroblast line, derived by transfection of y2 cells with pBabePuroMyc-ERTM, was stimulated with 4HT to induce increased MYC activity. After three days of stimulation by 4HT, numerous cyclin D2-containing ECEs are seen in metaphase chromosome spreads and in interphase nuclei (FIG. 12). This evidence of genomic instability and of cyclin D2 gene amplification were not seen in the same cells without prolonged tamoxifen stimulation (FIG. 12). A control FISH study of 4HT-stimulated y2 cells that do not bear the MYC-ERTM expression vector showed no cyclin D2-hybridizing ECEs (FIG. 12). Northern blots were prepared from total RNA from the fibroblasts with and without stable integration of pBabePuroMyc-ERTM, and after different periods of stimulation by 4HT. FIG. 13 shows the results of successive hybridization of this blot with cyclin D2 and other probes. As with the B cells, cyclin D2 message expression is clearly elevated after several days of MYC activation by 4HT, when compared to the GAPDH loading control.

The data presented in this report indicate that the mouse cyclin D2 gene has at least four MYC-MAX-binding EMS motifs 5' of its first exon. Oligonucleotides that contain any of these motifs bind purified MYC and MAX proteins, as well as MYC and MAX proteins that are present in lysates of mouse plasmacytoma cells. The presence of at least two CACGTG motifs upstream of the human cyclin D2 coding region suggests that these motifs have been evolutionarily conserved due to some essential role in normal cell physiology. This region of high structural homology has been recently suggested to play a role in regulation of cyclin D2 expression, but the role of MYC in genomic instability or cyclin D2 expression was not addressed directly (Jun et al., 1997). The details of how MYC/MAX binding to each individual EMS motif affects cyclin D2 transcription are the subject of another report (J. Hanley-Hyde, in preparation).

A direct role for MYC in cyclin D2 gene amplification was first suspected when a coupling was observed between Myc overexpression and amplification of the cyclin D2 gene in established tumors. Amplification of cyclin D2 was first seen in Southern blots of two human cell lines, COLO320HSR and T47D, which were known to have c-Myc amplification and overexpression. Similar evidence of cyclin D2 amplification was also found in mouse plasmacytomas that did not have c-Myc gene amplification but which did have c-Myc overexpression, due to chromosomal translocations. Extracts from these cells were shown to contain MYC/MAX complexes that bound in vitro to three of the CACGTG-containing oligonucleotides that is identified on the 5' of cyclin D2.

The cyclin D2 amplification that was detected in mouse plasmacytomas is associated with enhanced mRNA levels on RNA blots; more transcripts are found in plasmacytomas than in other cell lines that do not have c-Myc-activating chromosome translocations. Such increased expression of other members of the G1 cyclins, D1, D3 and E was not found in plasmacytomas, indicating that this was a special attribute of cyclin D2. Since cyclin D1 is not thought to be expressed in normal B lymphocytes (Sinclair et al., 1994), it can be noteworthy that two mouse B-cell lines exhibit substantial cyclin D1 expression: BALB 1437 and BAL 17. The mechanisms responsible for the overexpression of cyclin D1 in these lines have not been investigated.

To directly implicate MYC levels in the induction of cyclin D2 amplification, the effects of inducible overexpression of Myc in mouse pre-B cells is studied using a tamoxifen-activated pBabePuroMyc-ERTM chimeric expression vector. Since amplification of genes occurs gradually, over successive replication cycles. Instead, concentration is on the state of the locus and its expression over several days of 4HT stimulation. 4HT had no effect on the cyclin D2 of parent A-MuLV-transformed pre-B cells. In situ hybridization showed no evidence of genomic instability, and mRNA expression remained very low. In the cells with activated MYC-ERTM chimera, extrachromosomal elements, also called double-minutes or polydispersed circular DNA, episomes and extrachromosomal DNA (Cohen et al., 1997), that hybridized with the cyclin D2 probe, appeared after three to four days, indicating increased genomic instability. At these same time points, blots of RNA and cell lysates isolated from these cells began to show increased expression of cyclin D2 mRNA and protein. The data obtained to date do not require upregulation of either RNA transcription or changes in RNA stability. Simple status-quo rates of expression can yield increased steady-state levels of mRNA and protein if the template were increased, such as by the amplification that is demonstrated. Such a mechanism is also be responsible for the high levels of cyclin D2 mRNA in plasmacytomas, secondary to their constitutive expression of high levels of c-Myc mRNA and protein. It is interesting to note that Southern blots of DNA from pre-B cells after 3 days of 4HT-induction did not show increased cyclin D2 hybridization signals like those that were seen in well-established tumor cells that have experienced high MYC levels for many generations. This can be connected with the nature of DNA in extrachromosomal elements that have been amplified for a short time. This is not surprising, since it has been well documented in the literature that FISH analysis is a much more sensitive technique for identification of amplification of genes than Southern blotting (Cohen et al., 1997).

Such a connection between MYC expression and cyclin D2 amplification is probably not limited to B lymphocytic tumors, because amplified cyclin D2 in human colorectal and breast carcinomas is seen. In addition, a gradual increase in cyclin D2 expression in mouse fibroblasts is found when MYC is overexpressed and activated by 4HT treatment of cells that bear the pBabePuroMyc-ERTM expression vector.

This MYC-associated genomic instability can have another possible consequence: the frequent aneuploidy seen in plasmacytomas (and other cancer cells) that express high MYC levels and have been passaged for extended periods of time in vivo or in vitro. It has been reported that tumor-specific initiating non-random chromosome translocations become increasingly difficult to recognize with repeated passages due to accumulations of additional, presumably random, chromosomal aberrations (Coleman et al., 1997). However, it is important to emphasize that this MYC-associated tendency to amplification is locus-specific. It has been demonstrated previously for Dhfr and in this paper for cyclin D2, but is has been determined that high Myc expression produces no such amplification in the genes encoding ornithine decarboxylase, syndecan-2, glyceraldehyde-3-phosphate-dehydrogenase and cyclin C (Mai et al., 1996).

It possible to construct a hypothetical model for how Myc overexpression and the genes that are amplified in its presence might work together toward neoplasia. It is their common role in promoting cell cycle progression and cell proliferation that produces a potent combination favoring induction, promotion or progression of neoplastic transformation. Overexpression of Myc has been shown to shorten the G1 phase of the cell division cycle (Karn et al., 1989), which favors further mutations by curtailing the period available for cells to assess and repair DNA damage before it is duplicated in S phase. A similar effect can be expected from overexpression of cyclin D2, an important G1 cyclin. High levels of such cyclins are also foreshorten G1 and rush cells prematurely into S by titrating out cdk inhibitors such as p21 and p27. Perhaps such changes are responsible for the transformed characteristics that are induced by overexpression of cyclin D1 in fibroblasts (Jiang et al., 1993). Cyclin D1 amplification and overexpression is a well-known step in various cancers (Motokura and Arnold 1993; Wang et al., 1994; Zho et al., 1995). Amplification and/or overexpression of cyclin D2 can have similar effects. Overexpression of cyclin D2, along with D1 and D3, has been found in mouse skin neoplasms and has been associated with tumor progression (Zhang et al., 1997). Similar to the finding of cyclin D2 gene amplification in COLO320HSR, Leah et al. (1993) reported the amplification of this cyclin in a subgroup of colorectal carcinomas. What is more, inappropriate expression of cyclin D2 also occurs as a result of retroviral integration in retrovirus-induced rodent T-cell lymphomas (Hanna et al., 1993). Finally, the expression of G1 cyclins and their control of the cell division cycle is known to vary between normal and transformed cells (Hamel and Hanley-Hyde 1997).

As mentioned above, amplification associated with Myc overexpression is not random, but is locus-specific. Another gene that is amplified by Myc overexpression, Dhfr, is a key enzyme of folate metabolism, and it is essential for DNA synthesis. High levels of the product of this gene can contribute to maintenance of cell proliferation. High copy number of Dhfr genes, e.g., following amplification, have been correlated with the metastatic potential of tumor cells in a rat carcinoma model (Lueke-Huhle, 1994). Similarly, the gene encoding ribonucleotide reductase R2 subunit, which is required for dNTP (deoxynucleoside triphosphate) synthesis, is amplified as a result of c-Myc deregulation (T. I. Kuschak et al., submitted) Furthermore, it has been reported recently that the R2 protein is a malignancy determinant in neoplastic cells (Fan et al., 1996).

A model in which MYC promotes genomic instability fits the data reported here and offers a potential explanation for the frequent observation that high expression of c-Myc contributes to neoplastic development. Not only does it force cells through the G1 phase of the cell cycle abnormally rapidly, but also, if they escape apoptosis, these cells can suffer increased genomic instability in certain loci, which compounds the precocious cell cycling problem. This makes it possible, and indeed likely, that such cells will accumulate additional genomic alterations and complete the multi-step process of neoplastic transformation.

Example 4

To determine whether the locus-specific amplification of the DHFR gene occurred as a result of c-Myc overexpression in vivo, an animal model of c-Myc-dependent neoplasia is examined, the mouse plasmacytoma (Potter, et al., 1992). Using plasmacytoma-susceptible Balb/c mice, it is analyzed whether DHFR gene amplification occurred during pristane-induced plasmacytomagenesis. Balb/c mice are examined that were injected i.p. with pristane (Potter, et al., 1992). Control Balb/c mice received i.p. injections of LPS (lipopolysaccharide) that elicites the transient activation of B cells concomitant with a transient upregulation of c-Myc protein levels, but does not lead to PCT genesis which requires the constitutive overexpression of c-Myc (Potter, et al., 1992).

c-Myc protein levels of cells directly isolated from the peritoneal cavity (Potter, et al., 1992) were analyzed by quantitative fluorescent immunohistochemistry. Pristane elicited the elevation of c-Myc protein levels (Table 4). The induction level reached 4 to 10 fold three day post pristane injection and prevailed elevated for the next four weeks. LPS induced a similar, but transient upregulation of c-Myc protein levels in B lineage cells (Table 4). Non-treated peritoneal cavity cells exhibited low c-Myc protein levels (Table 4).

Next the Balb/c mice are examined to determine whether DHFR gene amplification in Balb/c mice was induced as a result of the above treatments. Peritoneal cavity cells were analyzed by fluorescent in situ hybridization (FISH). The amplification of the DHFR gene was observed after a single i.p. injection of pristane (Table 4). Interestingly, LPS did not lead to the amplification of the DHFR gene (Table 4). These findings allow one to conclude that the DHFR gene is a molecular marker of c-Myc-dependent genomic instability in vivo. Moreover, these findings confirm the previous in vitro data on c-Myc-dependent DHFR gene amplification in non-lymphoid and lymphoid cell lines of mouse, hamster, rat and human. Interesting, the fully developed plasmacytoma also exhibited DHFR gene amplification.

Figure 15:
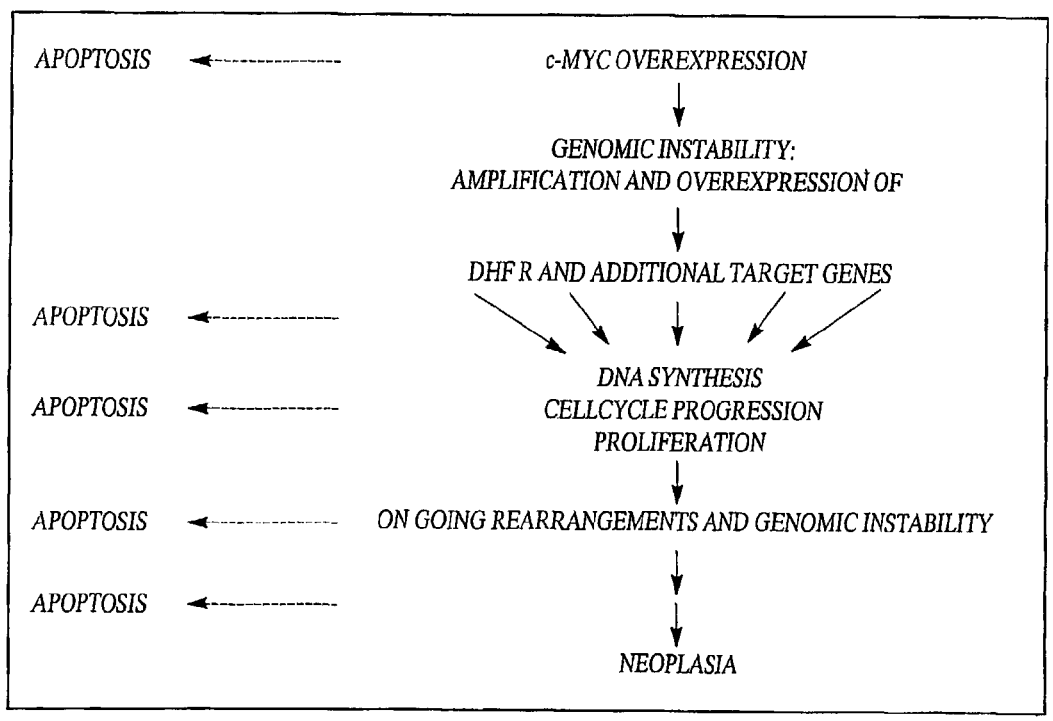
FIG. 15 shows c-Myc deregulation and the initiation of genomic instability.

As shown earlier, DHFR gene amplification and DHFR enzyme overexpression coincide (Luecke-Huhle, et al., 1996). It is not known whether the amplification of the DHFR gene is functionally important in c-Myc-induced genomic instability and neoplasia. Based on the fact that DHFR gene amplification occurs both early and late during pristane-induced plasmacytomagenesis in Balb/c mice, and this amplification event plays a role during the initiation of genomic instability and neoplastic transformation (FIG. 15). It has been described by others that imbalances in the nucleotide pool enhance mutation frequencies (Kunz, et al., 1994). Consistent with these findings, the amplification and overexpression of DHFR enzyme, which is a key enzyme of the folate metabolism, can lead to changes in the nucleotide pool, especially in the dTTP pool, which affect both DNA synthesis and mutation frequencies. Thus DHFR amplification and overexpression can account in part for accelerated acquisition rates of mutations and for further genomic instability. Moreover, DNA synthesis and cellular proliferation and thus the statistically elevated probability to generate a malignant clone can be enhanced due to DHFR amplification and overexpression. It is noteworthy that the potential to amplify the DHFR gene as well as the levels of DHFR gene amplification correlate with the metastatic potential in a rat tumor model (Luecke-Huhle,, 1994).

Example 5

Here, genomic instability in vivo is studied in different organs of $p53^{-/-}$ mice (4–6 weeks old), with age-matched p53 homozygous ($p53^{+/+}$) mice as controls. In all $p53^{-/-}$ tissues examined, a substantial percentage of cells contained abnormal numbers of centrosomes and displayed aneuploidy. Moreover, c-Myc overexpression was observed in 5–15% of $p53^{-/-}$ cells. In these cells, dihydrofolate reductase (DHFR), carbamoyl-phosphate synthetase-aspartate transcarbamoyl-dihydroorotase (CAD) and c-myc genes exhibited gene amplification. Apoptosis of cells, which displayed abnormal numbers of centrosomes, aneuploidy, gene amplification and c-Myc overexpression, was frequently observed.

Figure 16:
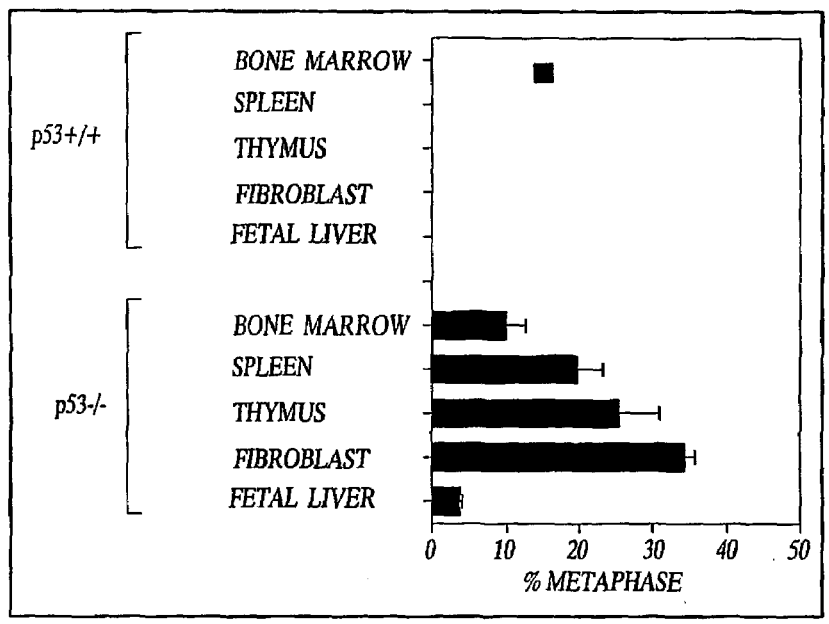
FIG. 16 shows genomic instability in $p53^{-/-}$ mice; Cytogenetic analysis of bone marrow, spleen, thumus-derived cells as well as of fibroblasts (passage 0) isolated from five $p53^{-/-}$ and five parental $p53^{+/+}$ (C57B1/6) mice, and of $p53^{-/-}$ and $p53^{+/+}$ fetal liver hematopoietic cells of 16 day old embryos.

Aneupolidy in $p53^{-/-}$ mice. Genomic instability is examined in different organs of clinically healthy $p53^{-/-}$ mice (4–6 weeks old) by cytogenetically assessing chromosome ploidy. Age-matched parental $p53^{+/+}$ mice were used as controls and then characterized as spleen-, thymus-, and bone marrow-derived cells, as well as skin- and spleen-derived fibroblasts. These analyses revealed aneuploidy; hyperdiploid, hypo-, hypertetraploid, and polyploid metaphase plates were present in all organs examined (FIG. 16). The percentage of aneuploid mitotic plates varied between individual mice; the mean frequencies were 25.6% in the thymus, 34.8% in fibroblasts, 10% in the bone marrow, and 20% in the spleen (FIG. 16). No aneuploidy was observed in $p53^{+/+}$ mice (FIG. 16).

Cytogenetic studies also revealed that five percent of all metaphases present in the $p53^{-/-}$ fetal liver hematopoietic cells were aneuploid (FIG. 16). In contrast, there was no evidence of aneuploidy in age-matched $p53^{+/+}$ fetal liver hematopoietic cells.

Figure 17A:
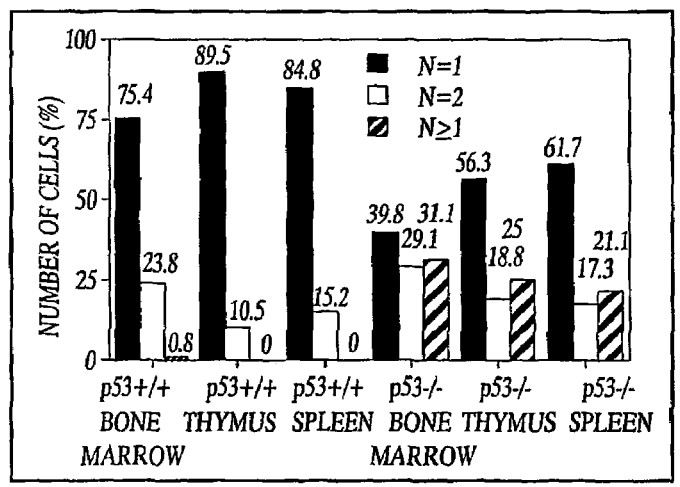
FIG. 17 shows an abnormal amplification of centrosomes in $p53^{-/-}$ mice; (a) Number of centrosomes detected by immunostaining in bone marrow, spleen, and thymic cells isolated from $p53^{+/+}$ and $p53^{-/-}$ mice. N1: one centromere; N2: two centromeres; N≧3: three or more centromeres (see text); (b) Representative picture of normal and aberrant centrosome numbers, the picture illustrates the normal number of centrosomes as found in all organs of $p53^{+/+}$ mice (top panel) as well as aberrant numbers of centrosomes as observed in all organs $p53^{-/-}$ mice in vivo (bottom panel)
Figure 17B:
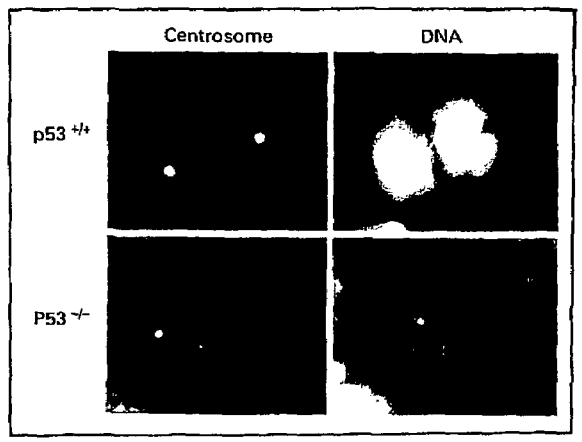
Figure 18A:
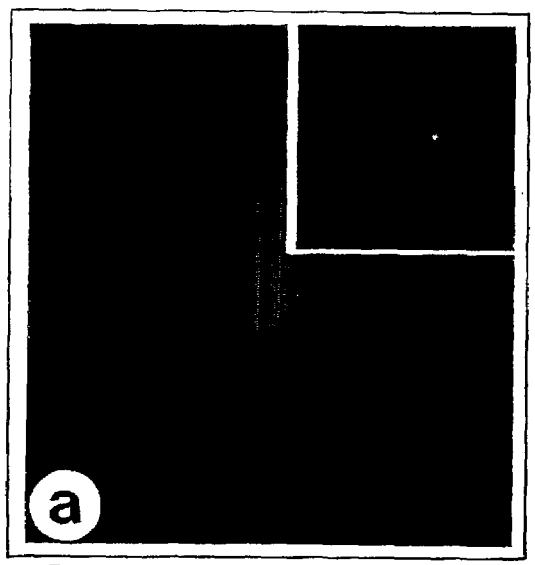
FIG. 18 shows genomic instability in $p53^{-/-}$ mice; Representative images of FISH analyses of DHFR and c-myc gene copies in $p53^{+/+}$ and $p53^{-/-}$ mice; (a) Single copy DHFR signals overlaid on DAPI staining in thymocytes of a parental $p53^{-/-}$ C57BL/6 mouse; (b) Amplified signals of DHFR overlaid on DAPI staining in $P53^{-/-}$ splenocytes; (c) Amplified signals of DHFR and c-myc overlaid on DAPI staining in $p53^{-/-}$ thymocytes; (d) Amplified signals of DHFR and c-myc overlaid on DAPI staining in $p53^{-/-}$ bone marrow cells; (e) Metaphase plate with extrachromosomal elements, indicative of early stages of gene amplification (Wahl, 1989), hybridizing with c-myc and DHFR probes, the most intense hybridization signals are pointed at by arrows, note that there are many tiny hybridization signals as well, filled arrow point to DHFR signals and open arrows to c-myc signals.
Figure 18B:
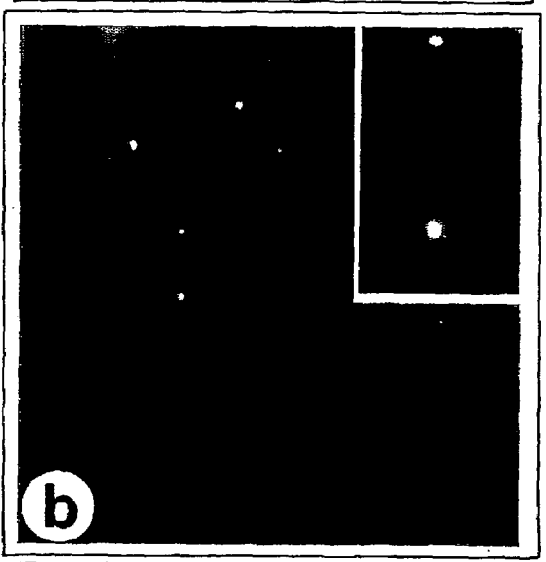
Figure 18C:
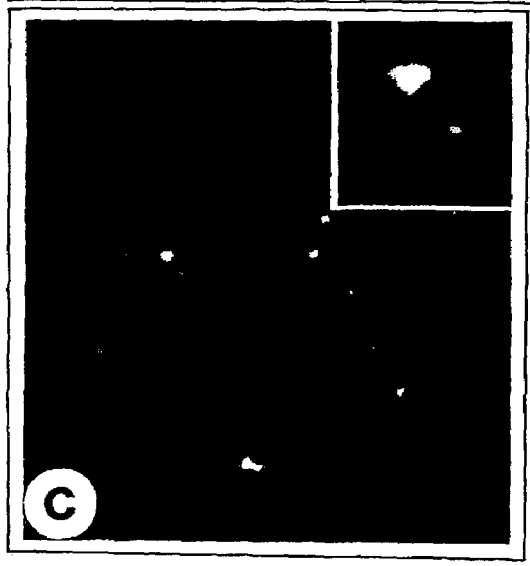
Figure 18D:
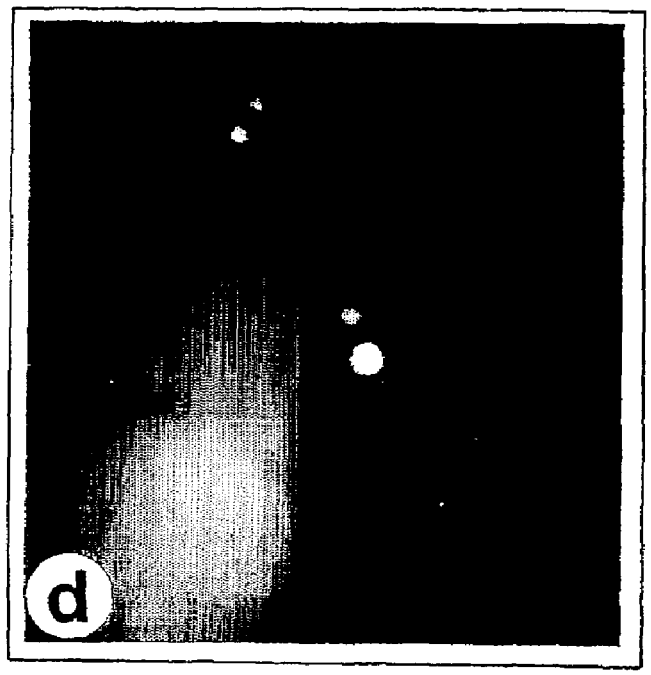
Figure 18E:
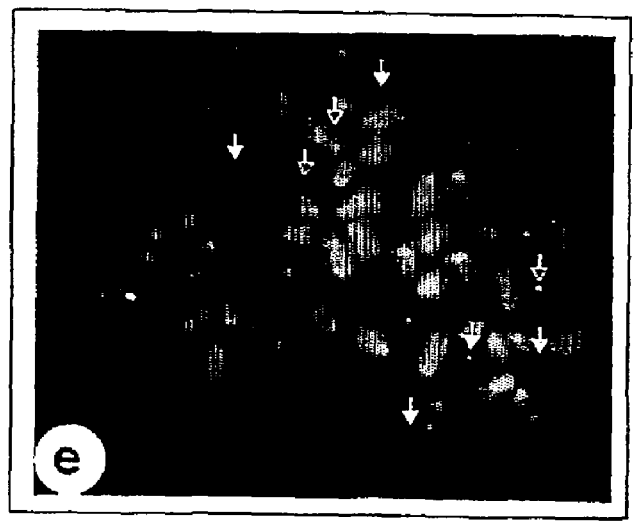
Figure 20A:
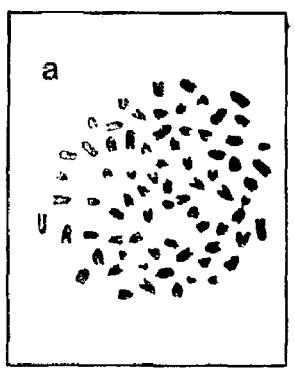
FIG. 20 shows apoptotic $p53^{-/-}$ cells exhibit atypical chromosome morphology, gene amplification, elevated c-Myc protein levels and abnormally amplified centrosomes, metaphase plates were prepared and evaluated as described (Mai, 1994; Mai 35 al., 1995, 1996); (a) shows a $p53^{-/-}$ thymus-derived Giemsa-stained aneuploid metaphase plate; (b) $p53^{-/-}$ spleen-derived chromosomes with atypical morphology, such chromosomes were present in all organs examined; (c) TUNEL assay was performed on $p53^{-/-}$ bone marrow-derived morphologically atypical chromosomes, extensive chromatid fragmentation was observed, as shown by a strong positive TUNEL reaction; DNA was counterstained with propidium iodide, intact DNA stretches can be identified and the fragmented chromatids can be recognized by their staining; (d) FISH analysis of bone marrow-derived chromosomes with atypical morphology, chromosomes were counterstained with DAPI, both c-myc and DHFR were amplified; (e) Spleen-derived interphase cells with chromatin condensation typical of apoptosis (arrows) and DNA fragmentation as determined by the TUNEL assay (dUTP-fluorescein incorporated by TdT), DNA was counterstained with PI, the number of apoptotic cells in P53$^{-/-}$ mice ranges between 2 and 11% in thymus, spleen, fibroblasts and bone marrow; (f) Representative image showing apoptosis in p53$^{-/-}$ thymocytes p53$^{-/-}$ thymocytes were immunostained for c-Myc along with TUNEL assay and DAPI staining, the cell indicated by an arrow shows chromatin condensation staining; (g) shows a p53$^{-/-}$ bone marrow cell displaying a typical apoptotic phenotype immunostained with anti-tubulin, the centrosomes are indicated by arrows.
Figure 20B:
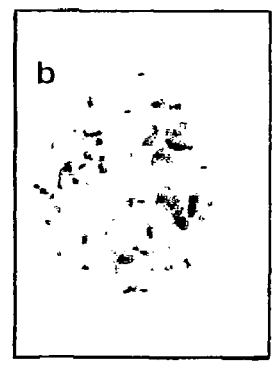
Figure 20C:
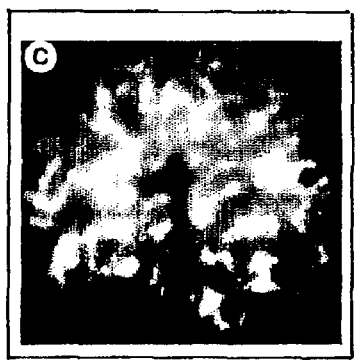
Figure 20D:
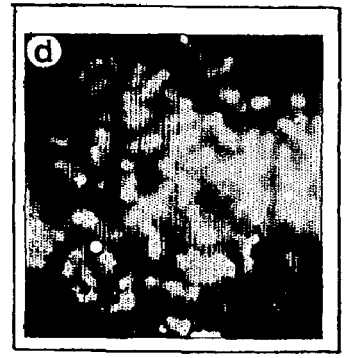
Figure 20E:
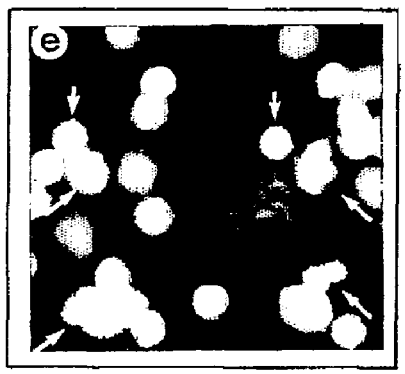
Figure 20F:
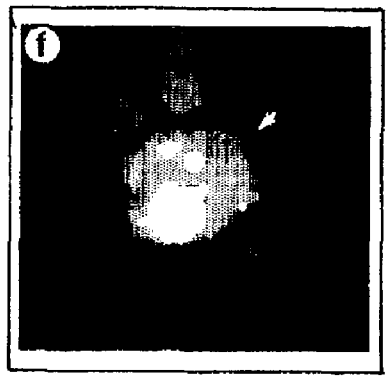
Figure 20G:
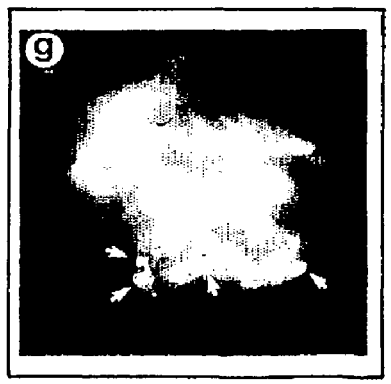

Abnormal centrosome amplification in vivo in $p53^{-/-}$ mice. p53 has been implicated in the regulation of centrosome duplication, and multiple centrosomes are generated in $p53^{-/-}$ embryonic fibroblasts (MEFs) during a single cell cycle (Fukasawa et al., 1996). In the present work, the chromosome instability is tested and observed in p53$^{-/-}$ mice was associated with multiple centrosomes per cell in vivo. Spleen-, thymus-, and bone marrow-derived cells were immunostained with anti-γ-tubulin antibody to identify centrosomes (reviewed in Oakley, 1992; Joshi, 1994), and the number of centrosomes per cell was scored. The numerical distribution of centrosomes in various organs of p53$^{+/+}$ and p53$^{-/-}$ mice is summarized in FIG. 17. More than 99% of the interphase p53$^{+/+}$ cells contained one or two centrosomes, most likely depending on their duplication cycle, while 20–30% of the interphase p53$^{-/-}$ cells contained >2 centrosomes. A typical example of normal vs. Aberrant centrosome duplication is shown in FIG. 17. Thus, as previously observed in vitro in p53$^{-/-}$ MEFs, in vivo that mitotic p53$^{-/-}$ cells frequently displayed abberant spindles, organized by multiple copies of centrosomes. However, as reported (Fukasawa et al., 1996) in some mitotic p53$^{-/-}$ cells, abnormally amplified centrosomes sequestered to the poles to form bipolarity. These results imply that abnormal amplification of centrosomes occurs in vivo, and this can lead to chromosome instability in p53$^{-/-}$ mice.

Gene amplification in p53$^{-/-}$ mice. To evaluate the genomic (in)stability of single genes in p53$^{-/-}$ mice in vivo, fluorescent in situ hybridization (FISH) was performed. Then analysis is conducted on the c-myc gene, which is frequently translocated and/or amplified in tumors (for review, see Marcu et al., 1992; Bishop, 1995), and the DHFR gene, whose genomic instability is altered following either drug selection (Stark, 1993), growth factor (Huang and Wright, 1994) or c-Myc overexpression (Denis et al., 1991; Mai, 1994; Mai et al., 1996). The CAD and the ribonucleotide reductase R1 (R1) genes were also examined. The CAD gene encodes a trifunctional enzyme of the pyrimidine biosynthesis and has been shown to be amplified after exposure to PALA (N-(phosphonoacetyl)-L-aspartate) (Otto et al., 1989; Yin et al., 1992; Livingstone et al., 1992). R1 forms a functional ribonucleotide reductase molecule in association with a second subunit, ribonucleotide reductase R2 (R2). The genomic stability of R1 is maintained even in malignant cells (Mai et al., 1996) and served as a control.

In all p53$^{-/-}$ tissues examined, there was detected an increase in fluorescent signals as observed by FISH for DHFR and c-myc as well as for CAD in both interphases and metaphases (FIG. 18 and FIG. 19). In contrast, no increase in fluorescent signals for the above genes was detected in age-matched control p53$^{+/+}$ mice (FIG. 18). R1 was present as single copy gene in both p53$^{-/-}$ and p53$^{+/+}$ cells.

An increase of fluorescent signals as detected by FISH can be due to two forms of genomic instability, karyotypic instability (gain of chromosomes) and/or gene amplification. The latter can also involve the formation of extrachromosomal elements which is frequently found in early stages of tumorigenesis (Wahl, 1989). Extrachromosomal elements were observed hybridizing with either DHFR or c-myc in all organs of 4–6 week old p53$^{-/-}$ mice; a representative picture is shown in FIG. 18.

c-Myc overexpression and amplification of c-myc, DHFR and CAD in the same p$_{53}$$^{-/-}$ cells. Since c-Myc overexpression has been shown to be associated with locus specific gene amplification, the levels of c-Myc protein in p53$^{-/-}$ bone marrow-, thymus-, spleen-derived cells as well as fibroblasts were examined by quantitative fluorescent immunohistochemistry (Materials and methods). Five to fifteen percent of the p53$^{-/-}$ cells in all tissues examined showed a two- to eightfold increase in c-Myc expression, while less than 1% of p53$^{+/+}$ cells expressed detectable levels of c-Myc protein. To determine whether c-Myc deregulation and genomic instability of single genes occurred within the same p53$^{-/-}$ cell(s) in vivo, the Combined Protein/FISH Analysis (CPFA) (Materials and methods) was developed. This assay allows the simultaneous analysis of c-Myc protein levels and FISH hybridization signals in the identical cell(s) in vivo. It therefore allows one to conclude whether c-Myc overexpression is associated with genomic instability in the same cell(s) in vivo. A similar technique has been independently established by Hessel et al. (1996).

Using CPFA, c-Myc overexpression and amplification of DHFR, c-myc, and CAD genes was observed, but not of the R1 gene within the same individual p53$^{-/-}$ bone marrow-, thymus-, spleen-derived cells as in primary fibroblasts (FIG. 19, panels a–a", b–b"). Thus, locus-specific gene amplification in p53$^{-/-}$ mice appears to be accompanied by c-Myc overexpression.

Apoptosis of genomically altered cells in p53$^{-/-}$ mice. Despite the extensive genomic alterations present in fetal and neonatal life, p53$^{-/-}$ mice develop without apparent abnormalities (Donehower et al., 1992; Jacks et al., 1994). One possibility is that cells with deleterious genomic alterations can be efficiently eliminated by apoptosis. Therefore it was determined that apoptosis occurred in organs and fibroblasts from p53$^{-/-}$ mice. Apoptosis frequently occurred in tissues and fibroblasts of p53$^{-/-}$ mice, with cells displaying chromatic condensation characteristic of apoptosis and a positive TUNEL reaction (FIG. 20). Cytogenetic and FISH analyses of p53$^{-/-}$ cells revealed the frequent presence of morphologically atypical chromosomes (FIG. 20) in contrast to aneuploid plates with the typical chromosome morphology (FIG. 20). Moreover, morphologically atypical chromosomes exhibited a strong positive TUNEL reaction in all organs examined (FIG. 20). Such morphologically atypical chromosomes were exclusively observed in p53$^{-/-}$ mice. They seem to undergo chromatid fragmentation and degradation and often showed gene amplification as well (FIG. 20). Apoptotic cells characteristically displayed multiple copies of centrosomes (FIG. 20), aneuploidy, c-Myc overexpression (FIG. 20), and/or gene amplifications (FIG. 20).

p53$^{-/-}$ mice develop a variety of tumors early in life (Donehower et al., 1992; Jacks et al., 1994), but the mechanisms underlying this tumor predisposition have remained elusive. Here, it is shown that cells directly isolated from p53$^{-/-}$ mice display extensive aneuploidy and gene amplification. This enhanced genomic instability is coupled with the high susceptibility and frequency of tumor development in these mice.

Genomic instability initiates during embryonic development and increases during life; haematopoietic cells of the fetal liver displayed 5% of aneuploidy, while all organs of young (4–6 week old) exhibited higher levels of aneuploidy (FIG. 16).

Abnormal amplification of centrosomes occurs in p53$^{-/-}$ mice in vivo, in all cell types tested. The adverse effects of abnormal centrosome amplification are readily observed in cells undergoing mitosis. For instance, the formation of aberrant mitotic spindles organized by multiple copies of centrosome was frequently observed in p53$^{-/-}$ mice. Such events are likely to impair chromosomal segregation, and induce karyotypic instability and aneuploidy.

Consistent with in vitro studies demonstrating that c-Myc expression is negatively regulated by p53 (Ragimov et al., 1993), it is found that in the absence of p53, all tissues became permissive to c-Myc overexpression. However, only 5–15% of p53 cells expressed high levels of c-My protein, suggesting that the additional event(s) can be required for c-Myc overexpression to occur and/or that cells overexpressing c-Myc undergo apoptosis (FIG. 20; Evan et al., 1992; Packham and Cleveland, 1995).

The absence of p53 and the deregulation of c-Myc expression seem to cooperate during tumor development. For instance, c-Myc overexpression and lack of p53 have synergistic effects during lymphomagenesis in Eµmyc/p53$^{+/+}$ and CD2-myc/p53$^{-/-}$ mice (Blyth et al., 1995; Hsu et al., 1995). Thus, c-Myc can play an important role in the overall tumor susceptibility of p53$^{-/-}$ mice by contributing to genomic instability, such as locus-specific gene amplification as well as increased proliferation rates (Karn et al., 1989).

It has been previously shown that cell lines overexpressing c-Myc display DHFR amplification, independent of species and tissue origins (Mai et al., 1996). Moreover, the c-myc gene was both translocated and amplified, and the protein was overexpressed in mouse plasmacytoma cells (Mai et al., 1995). In this study, the genomic stability of c-myc, DHFR, and CAD were tested, all of which were amplified concomitant with c-Myc overexpression in cells isolated from p53$^{-/-}$ mice.

While no mutagens were used in this study, several groups have shown earlier that the administration of the drug PALA (N-(phosphonoacetyl)-L-aspartate) leads to the selection of drug-resistant cells with amplified CAD genes (Otto et al., 1989; Yin et al., 1992; Livingstone et al. 1992), and this occurs with an enhanced frequency in p53$^{-/-}$ cells (Yin et al., 1992; Livingstone et al., 1992) A role for c-Myc in PALA-induced CAD amplification has not been described. Recent work suggests that c-Myc is involved in the transcriptional regulation of the CAD gene (Boyd and Farnham, 1997). Since c-Myc acts both as a transcription and replication factor, one can propose a role for c-Myc not only in the transcriptional activation, but also in the replication/amplification of the CAD gene. Consistent with this idea, it has recently been observed the PALA-dependent upregulation of c-Myc protein levels in p53$^{-/-}$ fibroblasts. Moreover, PALA-induced c-Myc overexpression occurred prior to CAD gene amplification (SM). C-Myc overexpression can thus precede the genomic instability of the CAD gene as it does for DHFR (Mai and Jalava, 1994; Mai et al., 1996), cyclin D2 (Mai et al., 1997) and ribonucleotide reductase R2 (Kuschak et al., 1997). Further investigation shows that c-Myc deregulation is a necessary and limiting molecular event in CAD gene amplification.

Genomic instability in p53$^{-/-}$ embryos and young mice affects several genetic loci, includes c-Myc overexpression, abnormal centrosome numbers and aneuploidy. Further genomic and molecular alterations, such as changes in the expression and/or half life of additional oncogenes, cell cycle related genes, growth factor-mediated signaling, DNA repair, etc., are conceivable, but have not been examined here. During the multistage process of carcinogenesis, all of the above events can ultimately contribute to the selection and evolution of neoplastic cell(s).

Despite extensive genomic alterations, p53$^{-/-}$ mice mature without discernible abnormalities until tumors start to appear (Donehower et al., 1992; Jacks et al., 1994). As is show here, there is a high incidence of apoptosis in all p53$^{-/-}$ tissues. In addition to interphase cells exhibiting chromosome condensation and a positive TUNEL staining, there is detected chromosomes with atypical morphology. These chromosomes stained in the modified TUNEL reaction and thus shows chromatid fragmentation. It is noteworthy that these apoptotic cells usually contained abnormally amplified centrosomes, expressed high levels of c-Myc protein, and displayed aneuploidy and gene amplifications. Thus, many of the genetically abberant cells can be eliminated through p53-independent apoptosis. This can explain how p53$^{-/-}$ mice seemingly develop normally. However, the yield of p53$^{-/-}$ offspring from heterozygous crosses has been reported to be only ~60% of the expected yield (Jacks et al., 1994), suggesting that some homozygous lethality occurs during embryogenesis. Indeed, genomic alterations were observed in a fraction of embryonic cells (Fukasawa et al., 1996, and this study). Since c-Myc has been implicated in apoptosis (reviewed in, Amati and Land, 1994; Harrington et al., 1994; Packham and Cleveland, 1995) and apoptosis occurs in the presence of elevated c-Myc expression in p53$^{-/-}$ mice.

Mice, cell suspensions, cell culture. Mice were obtained from Taconic farms (Ca, USA), with the exception of two p53$^{+/+}$ parental C57B1/6 mice that were obtained from Charles River (Quebec, Canada). Nine p53$^{-/-}$ and six p53$^{+/+}$ mice between 4 and 6 weeks old were used to prepare single cell suspensions of spleen, bone marrow, and thymus. Ten-day-old skin- and spleen-derived primary fibroblasts (passage 0) were also obtained from these mice by explanting subcutaneous skin tissue pieces and spleen fragments into RPMI 1640 medium supplemented with 10% fetal calf serum, 2 mM L-glutamin, and 1 mM sodiumpyruvate. Hematopoietic cells were prepared from fetal livers of 16-day-old embryos. Ten fetal livers were pooled for further analyses.

γ-tubulin immunostaining. Cells isolated from mice were seeded onto the slides. Samples were fixed in 3.7% formaldehyde in phosphate buffered saline (PBS) for 20 minutes at room temperature (RT). Cells were then incubated in the blocking solution (10% normal goat serum in PBS) for 1 h at RT. The samples were then incubated with anti-γ-tubulin antibody raised against CSREIVQQLIDEYHAATRPDY-ISWGTQ for 1 h at 37° C. The samples were then washed extensively in PBS, followed by incubation with fluorescein isothiocyanate (FITC)-conjugated goat anti-rabbit immunoglobulin G (IgG) for 30 minutes at RT. The samples were then washed extensively in Tris buffered saline (TBS), followed by 4',6' diamidino-2-phenylindole (DAPI) DNA staining (1 µg/ml). For each cell type, >400 cells were examined.

c-Myc determination. Quantitative fluorescent immunohistochemistry was used to determine c-Myc protein levels in single cells directly isolated from the mice. Following immunohistochemistry with 20 ng/slide of a monoclonal anti c-Myc antibody 3C7 (Evan et al., 1985) and a secondary antibody (anti-mouse IgG-Texas Red; Southern Biotechnology Associates, Inc., USA) at 10 ng/slide, images were acquired using a Zeiss Axiophot microscope, coupled to a CDD camera (Optikon/Photometrics), and the relative fluorescence intensity per pixel (one pixel=6.8 µm) was analyzed on a Power Mac 8100, using IPLabSpectrum and Multiprobe software, version 3.1 (Signal Analytics, USA). One hundred to three hundred cells were evaluated per sample.

Cytogenetics and fluorescent in situ hybridization (FISH). Metaphase spreads for cytogenetic analysis, FISH and a modified TUNEL assay (see below) were performed according to standard protocols (Mai, 1994; Mai et al., 1996) using cells directly isolated from the mice. Analyses of interphase cells by FISH, CPFA (see below) and the TUNEL assay (Li et al., 1995) were carried out on cytospin preparations. FISH determination of metaphase chromosomes and interphase cells was performed as described (Mai, 1994; Mai et al., 1996). All probes used have been described elsewhere (Mai et al., 1996), except the CAD probe (a generous gift from Dr.

George Stark, The Cleveland Clinic Foundation, OH). The number of metaphase plates evaluated for cytogenetic analyses was 50 per organ and 100 per fetal liver cells. The number of metaphase plates and interphases evaluated for FISH analyses was 100 per sample. Using the IPLabSpectrum and Multiprobe softwares (Signal Analytics, USA), amplified signals were determined with the 'Line Measurement' function; relative fluorescent intensities per pixel (one pixel=6.8 μm) were measured for single and amplified hybridization signals. As signal is classified as amplified if the ratio between the relative fluorescent intensity per pixel of amplified vs. the relative fluorescent intensity per pixel of single copy signals is >2 in one hundred interphase cells.

Combined protein/FISH analysis (CPFA). To visualize c-Myc protein expression and genomic (in)stability within the same cells, immunohistochemical analysis and FISH are combined. Cells immobilized on slides were fixed (3.7% formaldehyde), permeabilized (0.2% Triton X-100), incubated with 20 ng/slide of the anti-c-Myc monoclonal antibody (3C7, Evan et al., 1985), followed by the secondary Texas Red-conjugated goat anti-mouse IgG (Southern Biotechnology Associates, Inc., USA) (10 ng/slide). The nuclei were counterstained with DAPI (1 μg/ml in PBS), photographed, and the positions were recorded. Thereafter, the slides were processed for FISH analysis as described (Mai, 1994; Mai et al., 1996). Cells in the recorded positions were re-evaluated for their respective gene copy numbers. A microscopic field of $10^4$ to $10^5$ cells was analysed, and 100 cells were evaluated per sample. As above, relative fluorescent intensity per pixel was determined using the IPLab-Spectrum software (Signal Analytics, USA).

Apoptosis assays. The TUNEL assay was performed on interphase cells as described (Li et al., 1995). A modified TUNEL assay was designed to visualize gaps and DNA fragmentation on metaphase chromosomes. Metaphase chromosomes were prepared as described (Mai, 1994; Mai et al., 1996). Briefly, the slides underwent fixation, RNAse and pepsin treatments, and postfixation. Thereafter, the apoptotic assay was performed using dUTP-fluorescein and the terminal deoxynucleotidyl transferase (TdT) enzyme according to the suppliers (Boehringer Mannheim, Canada). Chromosomes were counterstained with propidium iodide (1 μg/ml) and analysed as described (Mai, 1994; Mai et al., 1996). Chromatin condensation was visualized with DAPI (1 μg/ml). One hundred to three hundred cells were evaluated per sample.

Example 6 c-Myc-dependent locus-specific genomic instability. In this study, the focus has been on the modulation of cellular proliferation as determined by the presence of elevated c-Myc protein levels. Furthermore, the presence of c-Myc-dependent locus-specific genomic (in)stability has been examined. Genomic instability is a hallmark of pre-malignant and neoplastic cells. However, current knowledge about the genomic changes that occur in a cell or cell population at the initiation of the carcinogenic process is still limited, and therefore no exact definition of "genomic instability" relevant to neoplastic transformation has been possible to date. In this example, the term "genomic instability" refers to c-Myc-dependent locus-specific genomic instability. In tissue culture as well as in animal models, it has been shown that the deregulated expression of the c-Myc oncoprotein mediates locus-specific genomic instability (Mai, 1994, Mai et al., 1996a, 1999, Kuschak et al., 1999; Taylor and Mai, 1998) as well as karyotypic instability (Mai et al., 1996b). Locus-specific genomic instability affects a number of genes, among them are the dihydrofolate reductase (DHFR) (Mai, 1994, Mai et al., 1996, Taylor and Mai, 1998), cyclin D2 (Mai et al., 1999) and ribonucleotide reductase R2 (R2) (Kuschak et al., 1999) and carbomoyl-phosphate synthetase-aspartate transcarbarnoyl-dihydroorotase (CAD) (Fukasawa et al., 1997) genes. At the same time, other genes such as syndecan-1, ribonucleotide reductase R1, ornithine decarbocylase (ODC) and cyclin C, remain unaltered in their genomic stability (Mai et al., 1996a). c-Myc-dependent karyoptypic instability is reflected by the generation of extrachromosomal elements, centromere-telomere fusions, DNA breakage and the presence of ring chromosomes (Mai et al., 1996b, Felsher and Bishop, 1999). These chromosomal changes are directly associated with the tumorigenic potential of the genomically unstable cells (Felsher and Bishop, 1999).

Based on these findings, it was thought to examine in human cervical cancer with well-defined stages of pre-neoplasia (dysplasia) as well as carcinoma whether c-Myc played a role in tumorigenesis and affected a target gene of c-Myc in genomic instability, the DHFR gene.

Materials and Methods

Thirty-six patients referred to the Colposcopy Clinic in the University of Manitoba's Department of Obstatrics, Gynecology and Reproductive Sciences, that is located at the Health Sciences Centre (HSC), were enrolled for the study. This study has ethics approval from The University of Manitoba Faculty Committee on the Use of Human Subjects in Research and a written consent was obtained. The study protocol included: A standardized history on each patient, collection of exfoliated cervical cells for the Pap smear and a colposcopically directed cervical biopsy and/or endocervical curretage (ECC), when clinically indicated.

Following collection of the cervical cells and preparation of Pap smears, the cervix was treated with 5% acetic acid and a colposcopic examination was performed using a Zeiss Colposcope OP-1 or OP-9, or a photocolposcope. The findings were recorded in a standardized form. Colposcopically directed biopsies and/or ECCs were performed and the cervical biopsy specimen was divided in two parts; one part was put in 10 formalin and the other kept fresh; both were sent to Pathology immediately.

The fresh tissue was then frozen in a cryostat (company) at −26° C. and serially sectioned at 5μintervals. The first few sections were stained by hematoxylin and eosin (H and E) and microscopically examined to make sure that the sections contained perpendicularly cut tissue from the transformation (T) zone. The following 5–6 sections were kept unstained and air dried for up to 24 hours, before being examined by fluorescent immunohistochemistry and fluorescent in situ hybridization (FISH). The remaining of the frozen tissue was put in 10% formalin and sectioned and stained together with the originally obtained and formalin-fixed tissue, dehydrated and paraffin embedded overnight.

The pap smear obtained at the time of colposcopic evaluation of the patient was fixed and stained by the classical Papaniscolaou method. It was screened at the Cytology laboratory of the Department of Pathology at HSC. The smear was reviewed and reported according to the combined Walton classification (no abnormal cells, reactive, atypical, mold, moderate, severe dysplasia, carcinoma in situ and invasive carcinoma) and the Bethesda system (no abnormal cells, reactive, ASCUS, low grade squamous intraepithelial lesion (LSIL), high grade squamous intraepithelial lesion (HSIL) and carcinoma).

The histologic sections were cut from the paraffin blocks at 8μ intervals and stained by H/E. These sections were reviewed and reported by one of the authors (M.P.). The degree, if any, of dysplasia present was reported as mild if the squamous epithelium contained enlarged, hyperchromatic, mitotically active cells occupying the lower third of squamous epithelium. Dysplasia was reported as moderate, if the dysplasia involved ⅔ of the thickness of squamous epithelium and severe/CIS if it involved the total thickness of the squamous eithelium. Any evidence of koilocytic surface changes and/or individual cell keratinization was noted and, in their presence, the diagnosis of HPV infection was suggested. Breaking of basal membrane of the surface squamous epithelium by neoplastic tissue and extension into the underlying stroma was taken as evidence of early (micro) or frank invasion, depending on the depth of invasion.

For the molecular and cytogenetic studies, sections were positioned on coated slides. The slides were coated with 3-aminopropyltriethoxy-silane (Sigma). The slides were dipped in 2% silane (in acetone), rinsed two times in distilled water, dried at 37° C. for two hours and stored at room temperature. All sections were then placed onto these slides and were analyzed in the following way. 5μ thick parallel sections were examined by quantitative fluorescent immunohistochemistry as described (Fukasawa et al., 1997). The antibody used was an anti-human Myc antibody (Oncogene Research). Images were acquired using a Zeiss Axiophot microscope, a CCD camera (Photometrics) and analyzed with IPLab Spectrum software (v3.1) (Scanalytics, Fairfax, Va.). Parallel sections were processed for fluorescent in situ hybridization (FISH) using a digoxigenin-labeled human dihydrofolate reductase (DHFR) probe (CHB204, obtained from ATCC). Detection of the hybridization was carried out using a FITC-conjugated sheep-anti-digoxigenin antibody (Roche Diagnostics). FISH analysis was performed with IPLab Spectrum software.

All images taken were matched with the respective areas of the parallel sections of the H and E stained slides.

Myc protein levels were assessed in the following way: elevated c-Myc protein levels were assessed with +, ++, +++ depending on the amount of c-Myc protein present in the nuclei of the cervical cells. No detectable nuclear immunofluorescence was recorded as negative, +; less than one third of all cells in the section displayed elevated c-Myc protein, ++; ⅔ of all cells displayed elevated c-Myc protein, +++; every cell displayed elevated c-Myc protein. DHFR gene copy numbers were recorded as negative, if all cells displayed single copy DHFR signals, as +/− when the occasional cell showed additional DHFR copies, + when a limited group of cells manifested DHFR gene amplification, ++ when more than 50% displayed DHFR gene amplification, +++ when >80% of the cells showed DHFR gene amplification.

Results

The results of the colposcopic, cytological and histopathological diagnoses were tabulated and then compared with those of the fluorescent immunohistochemistry and fluorescent in situ hybridization.

Quantitative fluorescent immunohistochemistry of biopsies derived from 36 patients enrolled in the study showed that c-Myc protein levels were elevated in 29 out of 36 patients (80.5%) (Table 1). Seven patients out of 36 (19.4%) without significant c-Myc protein elevation were found to have either no deectable cervical lesion (five patients out of 36 or 13.8%) or had CIN1 (one patient of 36 or 2.7%). One patient was CIN 3 (one patient out of 36 or 2.7%). In general, c-Myc protein levels were upregulated in early and late cervical lesions. Among the biopsies that were classified as negative, five showed elevated c-Myc protein (5/10 or 50%). The exact test was used to analyze the data. When negative and CIN1 (group A) was compared to CIN2, CIN3, and carcinoma (group B), c-Myc levels were significant ([=0.098). When the exact trend test was performed, the one tailed result for c-Myc was significant as well (p=0.032).

DHFR gene copy numbers were examined in 29 patients (Table 2) who were also studied by quantitative fluorescent immunohistochemistry. The presence of DHFR gene amplification was indicative of early and late malignancy (five out of 29 patients (17.2%) did not show DHFR gene amplification, two of these had no detectable cervical lesion (6.8%), three out were CIN1 (10.3%)). The level of DHFR gene amplification was associated with stage of disease. It is noteworthy that out of seven patients that were classified as negative, five showed DHFR gene amplification (one had low level amplification), the other one had high level with areas of very strong amplification (DHFR++/+++). The PAP smear of this patient was CIN3. Statistical analysis was carried out for the above results. The exact test gave significant values for DHFR (p=0.041) as did the one tailed trend test (p<0.0001).

Discussion

The data presented in this work shows that the assessment of c-Myc-dependent DHFR gene amplification is suitable as a molecular biomarker for cervical intraepithelial lesions. This biomarker is useful both for the detection of early cervical cancer and for tumor progression. If compared to other biomarkers, the genomic instability of the DHFR gene is one of the earliest markers available to date.

No studies have been performed on the genomic stability of the DHFR gene in cervical cancer. In contrast, a series of studies have been carried out on the amplification and expression of c-Myc. The data reported on c-Myc in cervical cancer are controversial. When evaluating the published reports, one has to distinguish between those that examined c-myc gene amplification and those that described c-Myc protein elevation or both. Both molecular alterations do not necessarily coincide. While indicative of genomic instability, the amplification of a gene without its overexpression is functionally irrelevant (see also Kuschak et al., 1999).

c-Myc gene amplification in cervical cancer. Some studies have suggested that c-Myc amplification is one of the early events in cervical intraepithelial lesions (Aoyama et al., 1998). However, Choo et al. (1989) reported that a Chinese group of cervical patients did not show c-Myc gene amplification. These data are supported by a more recent study that reports on low c-Myc amplification in invasive carcinoma, stages I and II of cervical cancer (Kersemaekers et al., 1999). In contrast, a French study found c-Myc amplification and protein overexpression associated with early stages of cervical cancer and related to the risk of relapse (Riou et al., 1990). The authors further report on the significant overexpression of the oncoprotein in later stages and suggest that c-Myc can be both an early marker and a progression marker (Riou et al., 1990). Bourhis et al. (1990) essentially come to similar conclusions. In a different study, Wu (1996) reported that c-Myc can be a valuable biomarker for cervical cancer.

c-Myc overexpression in cervical cancer. In studies performed on Mexican cervical cancer patients, c-Myc protein deregulation was found in 90% of the lesions (Ocadiz et al., 1989). Indian patients also displayed >90% overexpression of c-Myc. A Swiss study showed elevated levels of c-Myc by immunostaining, with the highest level of c-Myc found in high grade CIN (Dellas et al., 1997). These findings were contrasted by studies in Japan where the incidence of c-Myc protein deregulation was significantly lower (Iwasaka et al., 1992), however, c-Myc protein level was suggested as a prognostic marker for disease progression. A study carried out by Sowani et al., (1989) also suggested that c-Myc has prognostic value in treatment decisions. In contrast, Slagle et al. (1998) found no elevated c-Myc protein levels in normal to high grade cervical lesions (dysplasia). Work by Dellas et al. (1998) suggests that c-Myc expression is associated with proliferation in pre-cancerous lesions, but not with overall survival in invasive carcinoma (see also Symonds et al. 1992). In support of the c-Myc-induced proliferative potential is the study by Helm et al. (1993). The authors inhibited growth of ovarian and cervical carcinomas in situ by the use of a c-myc-targeted triplex forming oligonucleotide.

Trisomy of chromosome 8. Trisomy of a specific chromosome in cancer cells is usually associated with the overexpression of gene(s) involved in transformation. An example is trisomy chromosome 12 in a subset of chronic lymphocytic leukemia patients (Auer et al., 1999; Liso et al., 1999; Dohner et al., 1999; Van Kessel et al. 1999). Interestingly, Mark et al. (1999) have recently reported on trisomy 8 in cervical cancer. Chromosome 8 carries the c-Myc proto-oncogene (8q24).

HPV and integration sites. Preferential sites of HPV integration have been reported (Popescu and Di Paolo, 1989). Interestingly, HPV has been shown to integrate next to the N-Myc gene (2p24) and c-Myc gene (8q24.1) (Couturier et al., 1991). This integration can result in the deregulated expression of the Myc proteins. Co-amplification of HPV and c-Myc has been observed in a newly established cervical carcinoma line (Gotoh et al. 1991). Recently, Maeville et al. (1999) reported on HPV18 integration sites next to the c-Myc locus in HeLa cells. The authors also detected 8q24 amplification by CGH and confirmed the amplification of c-Myc by FISH. Additional chromosomes carry HPV copies next to 8q24-derived material (Maeville et al. 1999).

c-Myc protein levels in cervical biopsies determined by quantitative fluorescent immunohistochemistry. This data shows that c-Myc protein levels play a role in early and late cervical lesions. Therefore a prolonged overexpression of c-Myc in early lesions allows for the stable amplification of DHFR, which shows increased gene amplification over time and remains an indicator of tumor progression.

c-Myc-induced DHFR gene amplification determined by FISH. The amplification of the DHFR gene correlates best with the pathological and cytological evaluations. In cell lines and in a mouse model of c-Myc-dependent genomic instability, DHFR is amplified as a consequence of deregulated c-Myc expression (Mai, 1994, Mai et al., 1996a, Taylor and Mai, 1998). For this example, it is concluded that c-Myc overexpression is also associated with enhanced copy numbers of DHFR in cervical cancer.

Conclusions

This work shows that c-Myc-dependent DHFR gene amplification as a suitable marker of early and late cervical cancer.

The invention has been described in an illustrative manner, and it is to be understood that the terminology which has been used is intended to be in the nature of words of description rather than of limitation.

Example 7

Recently, greater advances have been made in the characterization of amplified genes and specifically EEs. Each of the more sophisticated technologies currently used can be applied to greater potential following additional purification of EE samples. Recently, it was demonstrated that functional EEs carried active histone proteins (Wiener et al., 1999). The presence of histones on functional Ees was used to develop a method enabling the isolation of EEs that carry genes. To facilitate the isolation of functional EEs extracted from tissue culture cells or clinical samples, the Hirt protocol (Hirt, 1967) was adapted that was originally designed to isolate polyoma virus particles. Preparations of EEs are frequently contaminated with varying amounts of genomic DNA and/or apoptotic DNA fragments (Regev et al., 1998). The contamination of EEs with genomic and apoptotic DNA was addressed by Gaubatz and Flores (Gaubatz et al., 1990), who described the use of exonuclease III, an enzyme that removes linear DNA molecules from these preparations. Exonuclease III also digests open and nicked circular extrachromosomal DNA molecules, potentially eliminating some of the EEs. Therefore, the use of this enzyme can compromise the isolation of a true and representative population of potentially transcriptionally or replicationally active EEs from a cell.

There are several advantages to immunopurifying EEs prior to their analysis. First, this immunoprecipitation method can be utilized as a primary post-extraction purification step following Hirt isolation of EEs. This immunopurification method allows for a number of analytical procedures to be conducted on a pure and heterogeneous population of EEs without genomic contaminants, derived from cultured cells, primary tissue, or tumor samples. In the experiments, immunopurified samples showed an enriched population of EEs that carry DHFR gene sequences and are free of genomic contaminants. Second, this purification method allows further experimentation with a greater degree of resolution. In the past, classical karyotype analysis was only able to show that EEs were present in the karyotype, though the sequence content of these EEs was not characterized. Recently, FISH-EEs (Kuschak et al., 1999) was successfully applied to test for the presence of genes on freshly isolated EEs. Using the ability to immunopurify EEs prior to performing FISH-EEs, it is now possible to identify potentially active genes that are (co)localized on a selected, but representative population of potentially functional EEs.

SKY has proven invaluable in visually identifying chromosomal re-arrangements in tumor cells and in showing the presence of EEs as well as the chromosomal origin(s) of those EEs (Ariyama et al., 1998). SKY analysis of EEs can be refined by probing immunopurified EEs specifically for histone-carrying and potentially active genes that are amplified or deleted from whole chromosomes, as opposed to the SKY analysis of all extrachromosomal DNA that is not necessarily associated with active chromatin.

CGH is a technology that is capable of detecting amplifications and deletions in genomic DNA (Kallioniemi et al., 1992). CGH can also be used to examine extrachromosomal DNA. Comparative analysis of CGH on immunopurified EEs in combination with CGH on genomic DNA can together resolve (i) the degree of amplification found on EEs, (ii) answer mechanistic questions about whether certain EEs are extrachromosomal amplification products derived from HSRs or the products of a chromosomal deletion. Thus, CGH can be used more precisely as a tool when only potentially active populations of EEs are compared. The isolation of large quantities of potentially active EEs using the immunoprecipitation method also facilitates the use of more traditional approaches such as Southern analysis of extrachromosomal DNA. Finally, the immunopurification of EEs expedites the isolation of sufficient quantities of purified and potentially active EEs, allowing for the creation of EE libraries, which was not previously possible.

Materials and Methods

Cell Culture

A mouse Pre-B ABM cell line was used for the generation and isolation of extrachromosomal DNA purification. This is a Myc-regulatable cell line that carries a Myc-ER™ that is activated by the addition of 100 nM 4-hydroxytamoxifen (4-HT) (Sigma-Aldrich Canada, Winston, ON, Canada). For simplicity, non-activated Pre-B cells are referred to as Pre-B− and 4-HT-activated Pre-B cells are referred to as Pre-B+ cells. The origin of Pre-B cells (Mai et al., 1996) and their culture conditions (Kuschak et al., 1999) have been described.

Isolation of EEs

Ees were isolated from Pre-B+ cells following activation as described in (Kuschak et al, 1999). The procedure for EE isolation is based on the protocol of Hirt (Hirt, 1967) and modified as previously described (Kuschak et al, 1999). The Hirt extract contains the bulk of the EEs and the total cellular RNA, but it can also be contaminated with small linear fragments of genomic DNA, and apoptotic DNA fragments which have been estimated to comprise 0.5 ñ 1.0% of the total amount of EEs isolated (Regev et al., 1998). Following isolation, all manipulations of EEs were performed in sterile, siliconized micro-centrifuge tubes (Fisherbrand, Fisher Scientific, Pittsburgh, Pa., USA).

Determination of Apototic or Genomic DNA Contamination in Non-Immunopurified Pre-B− and Pre-B+ Cell-Derived EEs Preparations of EEs were made from Pre-B− and Pre-B+ cells in triplicate. 4',6' diamidino-2-phenylindole (DAPI) (Sigma-Aldrich Canada, Winston, ON, Canada) (1 µgmL$^{-1}$ in PBS) was used to counter-stain both the EEs and any genomic DNA contaminants. The samples were then visualized and photographed using a Zeiss Axioplan2 microscope (Carl Zeiss Canada, Inc., Ottawa ON, Canada) under a 63× oil immersion objective and a UV filter. The images were acquired using Northern Eclipse 5.0 software (Empix Imaging Inc., Mississauga, ON, Canada) and a Sony (model XC75) CCD camera. The percentage of contaminating DNA was assessed in each of the preparations by manually counting and totaling EEs and signals from contaminating apoptotic or genomic DNA (Khaira et al., 1988). It was determined that Pre-B− and Pre-B+ cell-derived EE preparations carried 10.8±2.5% and 12.1±4.9% apoptotic or genomic DNA contamination, respectively.

Purification of Histone-Containing Extrachromosomal DNA Molecules

The Protein G sepharose beads were pretreated and (Amersham Pharmacia Biotech, Inc, Baie dÍUrfÈ, PQ, Canada), used for the immunopurification of the EEs. 1 µg of Protein G sepharose beads was washed in 5 mL Buffer A (100 mM KCl, 10 mM Trizma pH 7.4, 1 mM Na$_2$EDTA, 1 mM DTT, 1 mM AEBSF) by placing on a rotating platform for 10 minutes at room temperature. KCl, Trizma base, and Na$_2$EDTA were purchased from Sigma-Aldrich Canada, Winston, ON, Canada. DTT was purchased from FLUKA through Sigma-Aldrich Canada, Winston, ON, Canada. AEBSF was purchased from Roche Diagnostics, Laval, PQ, Canada. The beads were centrifuged at 13,000 rpm (16,000× g) for 10 minutes at room temperature and the supernatant was removed and discarded. This washing procedure was performed a total of three times. The non-specific binding sites on 40 µL of beads were blocked by resuspending the beads in 300 µL of Buffer B (Buffer A +4% (w/v) Bovine Serum Albumin) (FLUKA purchased through Sigma-Aldrich Canada, Winston, ON, Canada).

Immunopurification of extrachromosomal elements was used to perform the isolation of the Hirt-extracted histone-bound EEs from the impurities found in the Hirt-extracted EE sample. Freshly extracted EEs were dialyzed against 1×TE buffer (10 mM Trizma base, 1 mM Na$_2$EDTA, pH 8.0) overnight at 4° C. The EEs were then incubated in 500 µL Buffer B on a rotating platform for 10 minutes at room temperature. 1 µg of sheep polyclonal anti-core histone antibody was added per µg of EEs and incubated the mixture for 30 minutes at room temperature on a rotating platform. The blocked beads were then added to the antibody-treated EEs and incubated overnight on a rotating platform at room temperature. Following this incubation, the EE/beads were centrifuged at 13,000 rpm for 10 minutes at room temperature to remove any unbound material. The EE/beads were washed three times with Buffer A to remove any residual unbound material. The bound histone-containing EEs were eluted by adding 300 µL of 100 mM glycine (Sigma-Aldrich Canada, Winston, ON, Canada) (pH 2.3) to the beads and mixing gently by inverting the tube 5–10 times. The tube was centrifuged at 13,000 rpm for 10 minutes at room temperature and the supernatant (eluate) was removed and collected. This eluate was immediately neutralized to pH 7.2 using 1 M Trizma, pH 8.0. The elution step was repeated once more and the two collected eluates were pooled together. The sample was concentrated to approximately 40 µL by roto-evaporation.

Analyses of Immunopurified Extrachromosomal Elements

The following protocol allows the fixation of the EEs onto glass microscope slides and it ensures that the EEs are contained within a small area. Briefly: 40 µL of Hirt extract (Hirt, 1967) or immunopurified and concentrated EEs are diluted 1:1 in a fixative solution (freshly prepared 3:1 methanol:actetic acid) and then delivered onto pre-cooled (60 seconds on dry ice) slides (O. Kindler, Germany). The slides are immediately moved onto a slide warmer (37° C.). The fixation procedure was completed as described previously (Kuschak et al., 1999). Methanol was purchased from FLUKA through Sigma-Aldrich Canada, Winston, ON, Canada.

Non-immunopurified and immunopurified Hirt-extracted Ees were visualized by immunohistochemical staining (Kuschak et al, 1999). For this procedure, a sheep anti-core histone antibody diluted 1:200 and incubated for 30 minutes at room temperature was used. This was followed by incubation with a secondary antibody, a FITC-conjugated donkey anti-sheep IgG antibody (Sigma-Aldrich Canada, Winston, ON, Canada) diluted 1:400 in lamb serum (Gibco/BRL, Life Technologies, Inc., Burlington, ON, Canada) and incubated for 30 minutes at room temperature. Immunofluorescent analysis of histone-bound EEs was performed as previously described (Kuschak et al, 1999), the only modification being the omission of the permeabilization step. Anti-bleach (Mai, 1994) was added to preserve the fluorescence of the sample and to function as a mount for the cover slip. The immunostained EEs were analyzed using a Zeiss Axioplan2 microscope (Carl Zeiss Canada, Inc., Ottawa ON, Canada) under a 63× oil immersion objective and a UV filter.

The images were acquired using Northern Eclipse 5.0 software (Empix Imaging Inc., Mississauga, ON, Canada) and a Sony (model XC75) CCD camera. Adaptive thresholding tools (Northern Eclipse version 5.0 from Empix Imaging Inc., Mississauga, ON, Canada) were used to remove all dots from the DAPI-stained images that were ≦5×5 pixels in size when visualized using a 63× oil immersion objective lens and a 0.63× adapter.

FISH-EEs (Kuschak et al, 1999) was performed on Hirt-extracted EEs and on immunopurified EEs using a DHFR probe (Mai, 1994). The EEs were analyzed using a Zeiss Axiophot microscope (Carl Zeiss Canada, Inc., Ottawa ON, Canada) under a 100× oil immersion objective, a 1× magnification adapter, and a UV filter. The images were acquired using IPLab software (Scanalytics, Fairfax Va., USA) Photometrics (CH250/a) CCD camera equipped with a KAF-1400–50 sensor chip (1317×1035 pixels, Kodak).

Results

The isolation of the histone-bound population of extrachromosomal DNA extracted from Pre-B+ cells (Hirt, 1867) was performed by immunoprecipitation. Pre-B+ cells contain a 4-HT-responsive MycER™ construct and have been activated with 4-HT to overexpress c-Myc (Kuschak et al, 1999). This induces the activation of EEs from c-Myc activated Pre-B+ cells (Kuschak et al, 1999, Mai et al., 1999). These EEs were isolated, first by Hirt extraction (Hirt, 1967) and then followed by immunoprecipitation of histone-bound EEs.

Binding of Anti-Core Histone Antibody to Protein G Sepharose Beads

Sheep anti-core histone antibody was bound to Protein G sepharose beads according to manufacturer's instructions. Briefly, the anti-histone antibody was eluted from the Protein G sepharose beads by incubating in 100 mM glycine buffer, pH 2.3. The eluate was immediately neutralized to pH 7.2 using 1 M Trizma Buffer, pH 8.0.

Immunostaining Shows Enrichment of Histone-Bound EEs Following HIP-EEs

In the antibody-purified population, there was observed an enrichment in histone-bound EEs. In contrast, the sheep anti-core histone antibody was amplified by the FITC-conjugated donkey anti-sheep secondary antibody, giving a greater relative signal intensity in comparison to the weaker DAPI signal intensity. The data show that there are fewer DAPI signals in the immunopurified sample, indicating fewer EEs in the immunopurified sample, as compared to the non-immunopurified EEs. However, of the EEs isolated by immunopurification, the majority is co-localized with bright yellow or white signals indicative of histone protein. This demonstrates an enrichment of histone-bound EEs.

FISH-EEs Shows Enrichment of DHFR Sequences on EEs Following HIP-EEs

To assess the value of this EE immunopurification method, it was assayed for the enrichment of an extrachromosomally amplified gene. It was demonstrated previously that c-Myc deregulation results in amplification of DHFR in mouse, rat, hamster, and human cell lines (Mai et al., 1996). There was shown by the FISH-EEs method, that DHFR was present on extrachromosomal DNA from Pre-B+ cells (Kuschak et al, 1999). It was hypothesized that the enrichment of the Hirt-extracted EEs by the immunopurification method can increase the relative ratio of DHFR-containing EEs when comparing non-immunoprecipitated against immunoprecipitated EE sample populations.

The overlay shows an increased proportion of DHFR-containing EEs in comparison to the non-purified EE sample. There is shown an increase in the number of co-localized DAPI-FITC signals in comparison with the proportion of DAPI-FITC co-localized signals in the non-purified sample shown previously. In addition, there was also observed a number of DAPI signals that did not show co-localization with a FITC signal. These are likely histone containing EEs that do not contain DHFR sequences, but can contain sequences from other gene families (Coller et al., 2000, Kuschak et al, 1999, Mai et al., 1996).

Overall, these data indicate enrichment in the number of EEs that carry DHFR sequences, and presumably sequences of other c-Myc target genes, such as ribonucleotide reductase R1 and R2 genes (Kuschak et al, 1999), cyclin D2 (Mai et al., 1999), and potentially other, as yet unidentified genes (Coller et al., 2000).

Discussion

The immunopurification of the active population of extrachromosomal DNA molecules is advantageous in studying functional EEs since it enriches for a potentially active population of EEs, removing the non-histone-bound and presumably inconsequential population of EEs from the extrachromosomal DNA population. The value of this method as a primary means of isolating potentially functional EEs from a large population of extrachromosomal DNA amplicons was assessed by two methods.

It was first determined the percentages of contaminating apoptotic or genomic DNA in each EE preparation. Ees were prepared from non-immunopurified Pre-B– and Pre-B+ cells. The results indicate the Pre-B– and Pre-B+ had 10.8±2.5% and 12.1±4.9% genomic DNA contaminant, respectively. Immunoprecipitation of histone-bound EEs helps eliminate these contaminants.

Non-immunopurified and immunopurified EEs were examined by immunostaining for histone protein and comparing the ratio of DAPI-stained DNA molecules that co-hybridized with the signal from an anti-histone antibody. An enrichment of histone-bound Ees was seen in the immunopurified samples. Nearly all of the EEs in the sample of immunopurified EEs showed co-localization with FITC, indicating that the majority of the EEs in the purified samples contained histone proteins. The results of the immunostaining assay shows that this method is successful in isolating histone-bound EEs from a large pool of EEs that do not contain histone protein.

Then the number of EEs that hybridize with a gene of interest, in this case DHFR, was assessed. The experiments show that immunopurified EEs carry a larger relative number of DHFR sequences, indicating an overall enrichment of specific extrachromosomal amplicons. There was shown that although there is an increase in the proportion of EEs that hybridize with a DHFR probe, there are also a number of EEs where no FITC signal is seen to co-localize with DAPI stained EEs. This is expected since previous work has shown that a number of genes can be found on EEs from Myc-ERô-activated mouse Pre-B+ cells. These include ribonucleotide reductase R1 and R2 (Kuschak et al, 1999), cyclin D2 (Mai et al., 1999), as well as DHFR (Mai, 1994) sequences. It is likely that there are others as well (Coller et al., 2000).

In conclusion, it has been shown that the present method for immunopurification of EEs is useful as a means of studying extrachromosomal gene amplification phenomena as well as amplification-mediated expression of oncogenes, drug-resistance genes, and potentially others. The immunopurification of EEs is a novel tool that is ideally suited as a first step purification of EEs for a variety of studies in cultured cells, primary cells, and tumor samples. These analyses and procedures include generating libraries of EEs from cells, analyses of EEs by electron microscopy, fluorescent in situ hybridization (FISH-EEs) (Khaira et al., 1988, Kuschak et al, 1999, Mai, 1994, Mai et al., 1999), mRNA FISH (Start et al., 1984, Von Hoff, 1991), cloning, and Southern blotting.

Example 8

The activation of the c-myc gene is key to the development of all murine plasmacytomas (PCTs), resulting in deregulated levels of endogenous c-Myc protein expression (Cory, 1986; Ohno et al., 1979; Potter et al., 1992). In the majority of pristane-induced mouse PCTs, the deregulation of c-myc transcription is achieved by chromosomal translocation that juxtaposes the c-myc/pvt-1 locus on chromosome 15 to one of the immunoglobulin (Ig) loci: on chromosome 12 (IgH), 6(IgK) or 16(IgL) (Ohno et al., 1979; Potter et al., 1992). More than 90% of PCTs carry the typical T(Janz et al. 1997; Wang et al., 1971) translocation, whereas the variant T(corcoran et al., 1984; Wang et al., 1971) or T(Wang et al., 1971: Committee, 1969) translocation is present in fewer than 10% of PCTs (Potter et al., 1992).

In a few PCTs, classical G-banding analysis could not identify any of the plasmacytoma-associated typical or variant translocations (Potter et al., 1992). Molecular and cytogenetic analysis of two translocation-negative PCTs, ABPC22 and RFPC 2782 (Shaughnessy et al., 1993), revealed that the overexpression of the c-myc gene was achieved by promoter/enhancer insertion brought about by retroviral insertion into the 5' flanking region of c-myc. Such retroviral deregulation of the c-myc gene is not unique. It was shown to operate in avian bursal lymphomas and also in MuLV induced lymphomas of T-cell origin (Hayward et al. 1981; Corcoran et al., 1984; Graham et al., 1985). Unusual gene rearrangements have been described in two other translocation-negative PCTs that lack retroviral insertion, namely in ABPC45 and DCPC21 (Fahrlander et al., 1984; Ohno et al., 1989; Ohno et al., 1991). In both cases, it has been reported that the c-myc-IgHjuxtapositon was achieved via complex rearrangements that resulted in a new gene order on the myc-activated chromosome (Fahrlander et al., 1984; Ohno et al., 1989; Ohno et al., 1991), different from that found at the chromosomal breakpoint of typical T (Janz et al. 1997;1 5) PCTs (Muller et al., 1995, Janz et al. 1997). For both of these translocation-negative PCTs, molecular analysis revealed that the 5' flanking region of c-myc is juxtaposed either to 3' Sa or to 3' Smjt, respectively, in 5' to 3' ("head to tail") orientation. This is in striking contrast to the "head to head" (5' to 5') configuration of the Ch locus and the c-myc gene that is present in every PCT of the typical T(Janz et al., 1997; Wang et al., 1971) type.

Although fewer than 1% of the PCTs analyzed to date belong to the group of translocation-negative plasmacytomas, they are of interest because they reveal a new mechanism of plasmacytomagenesis that is unrelated to viral LTR insertion, or to the interchromosomal recombination that has been implicated in virtually all PCT-associated deregulation of c-myc transcription. Consequently, the lack of cytogenetically identifiable translocations suggests alternate pathways by which c-Myc overexpression is achieved in this group of tumors.

To examine the mechanism(s) of c-Myc deregulation in translocation-negative PCTs, the investigation was focused on DCPC21, a plasmacytoma that had been induced by intraperitoneal implantation of a plastic diffusion chamber into a BALB/c female mouse (Ohno et al., 1989). Previous work by these authors had suggested that DCPC21 exhibited complex molecular rearrangements leading to the IgH-myc gene juxtaposition by the insertion of the myc and pvt-1 loci-containing chromosome 1 5 segment into the IgH locus on Chr 12(Ohno et al., 1991). The realization of such a complex rearrangements requires the occurrence of a paracentric inversion, a deletion/insertion, and multiple translocations both on chromosome and gene levels during the process of the IgH-myc illegitimate recombination (Ohno et al., 1991).

Here it is shown that the results of classical and molecular cytogenetic analyses show that the DCPC21 plasmacytoma lacks any type of interchromosomal recombination that could cause the constitutive activation of the c-myc gene. However, chromosomal segments containing c-myc and IgH sequences are present, either alone or jointly, on extrachromosomal elements (EEs) in the DCPC21 plasmacytoma. It is demonstrated that the deregulated expression of c-myc occurs on EEs, and this appears to be sufficient to sustain the malignant phenotype of the DCPC21 tumor.

Material and Methods

Tumor cells. DCPC21 was induced in a female BALB/c mouse by i.p. implantation of a Millipore diffusion chamber (Merwin et a., 1963).

Trypsin-Giemsa Banding. Metaphase spreads were prepared without colcemid treatment. Trypsin-Giemsa banding was performed as described previously (Wang et al., 1971) and adapted to mouse chromosomes. Chromosome identification followed the recommendations of the Committee on Standardized Genetic Nomenclature for Mice (Committee, 1969).

Molecular cytogenetics. Chromosomes were analyzed by FISH (fluorescent in situ hybridization ) as previously published (Mai, 1996, Fukasawa et al., 1997). Analysis of slides was performed using a Zeiss Axiophot microscope, a PowerMacintosh 8100 computer, and a CCD camera (Photometrics); the analytical software used was IPLabSpectrum Version 3.1 (Signal Analytics, USA).

FISH probes and detection of hybridization. The following probes were used, c-myc (Mai, 1994), IgH (pJII; Greenberg et al., 1982) and pvt-1 (Huppi et al, 1990). The probes were labeled by random priming with either digoxigenin- or biotin-dUTP (Roche Diagnostics, Laval, Quebec, Canada). The detection of hybridization signals with digoxigenin-labeled probes was carried out using a fluorescein conjugated polyclonal sheep anti-digoxigenin-antibody (Roche Diagnostics). For the detection of hybridization signals obtained with biotinylated probes, a monoclonal anti-biotin antibody (Roche Diagnostics) was used, followed by a Texas Red-conjugated goat anti-mouse-IgG secondary antibody (Southern Biotechnology Assoc., Inc., Birmingham, USA).

FISH-EEs (FISH on purified extrachromsomal DNA molecules). The total population of extrachromosomal elements (EEs) was purified and examined by FISH as described in (Kuschak et al., 1999). EEs were hybridized with c-myc, IgH and pvt-1. The specificity of these hybridizations was confirmed by the absence of hybridization signals with a negative control, cyclin C (Mai et al., 1996; Kuschak et al., 1999) and hybridization signals obtained with a positive control, cot-i DNA.

Chromosome painting. The chromosome paints used (CedarLane, Laboratories Limited, Hornby, Ontario, Canada) were a FITC-conjugated mouse chromosome 15 and a biotinylated mouse chromosome 12-specific paint. Hybridization of chromosome paints, alone or in combination with FISH probes, was carried out as described in the general FISH protocol. Chromosome 12 hybridization signals were detected with a monoclonal anti-biotin antibody (Roche Diagnostics) at 0.5 ng/slide followed by a Texas Red conjugated goat anti-mouse-IgG secondary antibody (Southern Biotechnology Assoc., Inc., Birmingham, USA) at 2.5 ng/slide. The hybridization signals of the FITC-labeled chromosome 15 paint were amplified using a rabbit anti-FITC antibody (CedarLane), followed by a FITC-labeled goat anti-rabbit IgG secondary antibody (Sigma). Both antibodies were used at 1:40 dilution.

SKY. Spectral karyotyping was performed using the ASI (Applied Spectral Imaging, CA, USA; Migdal Ha'Emek, Israel) kit for mouse spectral karyotying and the suppliers' hybridization protocols. Analyses were carried out using the Spectra CubeTM on a Zeiss Axiophot 2 microscope and the SkyView 1.2 software on a PC (P11-3 50).

mRNA track studies. mRNA tracks studies were carried out as described in (Szeles et al., 1999) on freshly isolated ascitic DCPC21 tumor cells. The cells were cytospun onto microscopic slides (10 ~cells/slide) and fixed in formaldehyde (1% in 1×PBS/5OmM $MgCl_2$). The slides were washed in 2×SSC, dehydrated sequentially in 70%, 90% and 100% ethanol. A denatured mouse c-myc probe, pMycEx2, a 460 bp PstI-fragment of myc exon 2 (gift from Dr. K. Huppi, NIH), was added in 50% formamide/2×SSC/5OmM phosphate buffer, 10% dextran sulfate for overnight hybridization at 37° C. in a humidified incubator. As expected, subsequent RNAse treatment removed any hybridization signals, and hybridization to chromosomes or extrachromosomal material was only achieved after the slides had been treated with RNAse and pepsin and denatured prior to the addition of FISH probes (see also Lawrence et al., 1989).

Fluorescent immunohistochemistry. Immunohistochemistry was performed as described (Fukasawa et al., 1997). The following antibodies were used, a monclonal anti-c-myc antibody, 3C7 (Evan et al, 1985) at 20 ng/slide. Visualization of this antibody was achieved with a Texas Red—conjugated secondary goat anti-mouse IgG antibody (Southern Biotechnology Assoc., Inc., Birmingham, USA) at 2.5 ng/slide. A sheep anti-CORE histone antibody (US Biological) was used at 5 ng/slide and visualized with a FITC-conjugated donkey anti-sheep IgG antibody (Sigma) at 2.75 ng/slide, and an anti-histone H3P antibody that were received. The anti-histone H3P used is a histone H3-phophoserine monoclonal antibody from Dr. Z. Darzynkiewicz (Juan et al, 1998). It was used at 4.0 ng/slide and visualized with a Texas Red-conjugated goat anti-mouse IgG antibody (Southern Biotechnology Assoc., Inc., Birmingham, USA) at 2.5 ng/slide.

Southern analysis. For Southern analyses, 10 ~tg DNA from primary BALB/cRb6.15 spleen or DCPC21 tumor DNA was digested was digested overnight with 40 units of either HindIII or Sad restriction endonucleases (Roche Diagnostics) and electrophoretically separated on a 0.8% agarose gel, blotted onto Hybond XL membrane (Amersham Pharmacia Biotech), and baked at 80° C. for 2 hours. Hybridizations and washes were carried out according to standard procedures (Sambrook et al., 1989). The probes used were, c-myc (Mai, 1994), pJi i (Greenberg et al., 1982) pvt-i (Huppi et al., 1990; Mai et al., 1995), JQ2 (Ohno et al., 1991).

Electroporations. Spleen cells of BALB/cRb6. 15 mice were harvested for extrachromosomal gene transfer studies as follows. Green fluorescent protein (GFP, pEGFP-N1 Clontech, Mississauga, Ontario, Canada) was used as a tracer molecule for determination of gene transfer efficiencies. Lymphocytes isolated from one spleen were divided into three groups: electroporation of GFP plus c-myc/IgH-carrying EEs (2.5 ~tg), electroporation of GFP (2.5 jig), and "mock" electroporation. Electroporations were carried out in OPTI-MEM solution (Canadian Life Technologies, Burlington, Ontario, Canada) using 1 ml Gene PulserR cuvettes, 0.4 cm (Bio-Rad, Hercules, Calif., USA) using a Bio-Rad electroporator, model #1652076, and a Bio-Rad Capacitance Extender, model #1652087. The settings used were: 960K, 240V, cap. 25 units. Subsequent to electroporation, the cells were washed in complete medium (RPMI164O with 10% fetal calf serum (Canadian Life Technolgies, Burlington, Ontario, Canada), 2 mM Lglutamine, 5 IU/ml of penicillin and 5 ~g/ml streptomycin and 50 ~tM/ml~3-mercaptoethanol and allowed to grow in complete medium in a humidified incubator at 37° C. and in the presence of 5% $CO_2$. 24 hours after transfer, cells were cytospun onto microscope slides (10 ~cells/slide), and c-Myc protein expression was determined in splenic B cells that also expressed GFP. A FITC-conjugated anti-B220 antibody (Pharmingen, Mississauga, Ontario, Canada) was used to visualize splenic B cells on cytospin preparations. Fluorescent immunohistochemistry of the electroporated cells was carried out as previously described (Fukasawa et al., 1997).

Results

DCPC21 is a Translocation-Negative Plasmacytoma Harboring Extrachromosomal Elements Karyotyping of DCPC21 metaphase spreads by standard G-banding revealed that chromosomes 15, 12, 6, and 16, regularly involved in mouse PCT-specific translocations, were not part of reciprocal translocation events. To confirm the results provided by G-banding, DCPC21 metaphases were further examined by chromosome painting, fluorescent in situ hybridization (FISH), and spectral karyotyping (SKY). Since the most frequent translocation (>90%) in pristane-induced mouse PCT transposes the c-myc containing segment of chromosome 15 into the neighborhood of the IgH gene loci on chromosome 12 (Potter et al., 1992), chromosome painting was performed to ascertain whether chromosomes 12 and 15 are carriers of cryptic rearrangements. The painting with chromosome 15- and 12-specific probes revealed the presence of four copies of chromosome 15 (green) and chromosome 12 (red) in the majority of the DCPC21 plates analyzed. More importantly, neither chromosome 15- nor chromosome 12-derived genetic material was found to be translocated or inserted into any other chromosome of DCPC21 metaphases.

When either chromosome 12 paint was combined with FISH using a c-myc probe or chromosome 15 paint used in combination with an IgH probe (pJi i), it was also evident that chromosomes 12 and 15 were not involved in reciprocal translocations. However, extrachromosomal elements (EEs) carrying either cmyc or IgH genes alone or c-myc and IgH genes jointly became apparent.

The possible involvement of the IgK- and IgL-carrying chromosomes 6 and 16 in Ig/myc translocation was analyzed by SKY. SKY corroborated the data obtained by standard cytogenetics, painting and FISH, namely, that DCPC21 does not carry any plasmacytoma-associated c-myc-activating translocation.

In addition, SKY revealed the nature and structure of the chromosomal aberrations detected by G-banding. Noteworthy, SKY showed that the duplicated D2 band on one of the chromosomes 15 contained only chromosome 15-derived genetic material, excluding the likelihood of an interchromosomal rearrangement involving chromosome 15. The additional band on chromosome 9 was identified as derived from chromosome 16, while one copy of chromosome was centromerically fused with one chromosome 19. A "hidden" chromosomal aberration, undetected by classical G-banding, was the insertion of chromosome 3-derived material into one chromosome 2. Since the aberrations involving chromosomes 9 and 2, as well as the fusion of chromosomes 16 and 19, were not consistently seen in all metaphases, they are likely chromosomal aberrations acquired during tumor progression, rather than during tumor initiation.

Classical cytogenetics, chromosome painting, FISH and SKY establish that the DCPC21 plasmacytoma lacks any chromosomal aberration that could reasonably be involved in the constitutive activation of the c-myc gene. However, the presence of IgH and c-myc sequences on extrachromosomal elements (EEs) suggests that these genetic entities can be responsible for the deregulation of c-Myc in this tumor.

Southern Blot Analysis Shows Rearrangements within the IgH Locus and in the 5' Flanking Region of c-Myc.

Southern blot analysis was performed with normal mouse spleen DNA and DCPC21 tumor DNA. The c-myc gene, visualized by using a mouse exon 2-specific probe, showed no rearrangement(s) and exhibited identical hybridization patterns in HindIII- and SacI-digests of normal spleen and DCPC21 DNA. Similarly, pvt-1 showed no evidence of rearrangements. The stronger hybridization signals of cmyc andpvt-i in DCPC21 DNA reflect both the duplication of the myc/pvt-i-containing 1 5D2 band of one of the chromosome 15 and the additional copies of chromosome 15. In contrast to the germ line bands observed with c-myc and pvt-i, rearrangements within the IgH sequences and in the 5' flanking region of c-myc became apparent when using the IgHprobe (pJii) as well as a 5' flanking probe of the c-myc gene (JQ2).

Since none of the bands that hybridized with pJii cohybridized with JQ2, it can be excluded that any of the additional bands represent a cryptic transposition of sequences detected by pJi 1 and JQ2. Furthermore, a transposition ofpvt-1 and c-myc within the chromosomal DNA ofDCPC21 is unlikely, since these two genes were not involved in translocation and or rearrangement events detectable in genomic DNA. These results suggest that the rearranged genomic bands represent intrachromosomal rearrangements, possibly due to the excison of c-myc and IgH sequences from the relevant chromosomes rather than interchromosomal recombination.

c-Myc and IgH Co-Localize on Extrachromosomal Elements (EEs) and are Functional Genetic Units Extrachromosomal c-myc and IgH hybridization signals in DCPC21 metaphases were observed. To analyze these EEs further, FISH was performed on the total population of EEs. In the majority of the cases, c-myc and IgH were found together on the large EEs (0.1–0.2 ~tm in diameter, as determined by electron microscopy (EM) measurements). Noteably, c-myc and IgH were also found alone on EEs of smaller sizes (0.01 ~tm in diameter). pvt-I could be detected on some of the EEs, together with c-myc and IgH.

The co-localization of c-myc/IgH on some of the EEs raised the question whether these EEs are biologically active structures. To investigate this hypothesis, it was analyzed whether these EEs were associated with active chromatin, could transcribe c-myc mRNA and confer c-Myc overexpression to resting primary B cells in extrachromosomal gene transfer studies.

To determine whether the EEs contained active genes, first examined was: i) the presence of histones and of the transcription-associated phosphorylated form of histone H3 (H3P) (Juan et al., 1998; Juan et al., 1999) on the EEs and ii) carried out mRNA track studies. Using a pan-histone antibody that detects all histones irrespective of chromatin activation, histones were found on the large, but not on the small EEs. To determine whether the former were also transcriptionally active, the presence of H3P was examined using a monoclonal anti-histone H3P antibody (Materials and Methods). In over 90% of the pan-histone-containing EEs it was found that they also stained with the monoclonal anti-histone H3P antibody, indicating that these EEs contained active chromatin.

To examine whether c-myc mRNA was produced from these EEs, mRNA track studies were carried out. Multiple short c-myc RNA tracks were observed, typical of episomal (extrachromosomal) gene transcription (Szeles et al., 1999), were generated from DCPC21-EEs. To unequivocally demonstrate that the mRNA was derived from the EEs, the identical slides were processed for FISH after RNAse and pepsin treatment and following slide denaturation. Co-localizing c-myc mRNA (red signals) and c-myc-EEs DNA signals (green). All c-myc mRNA tracks were consistently observed to be colocalized with EEs that showed c-myc DNA by FISH. However, the number of c-myc-carrying EEs in a DCPC21 cell was higher than the amount of EEs that were transcribing c-myc mRNA.

To further examine the functional activity of DCPC2 1 EEs, purified EEs were electroporated into normal BALB/cRb6. 15 spleen cells together with a vector expressing green fluorescent protein (GFP). The latter served as tracer molecule for gene transfer efficiency. The B lineage-specific marker B220 was used to determine the lineage origin of the electroporated cells. When purified DCPC21 EEs were introduced into normal BALB/cRb6. 15 spleen cells, they conferred c-myc expression to GFP-expressing B220-positive B cells. However, within 24 hours, the DCPC-21 EEs induced cell death in the majority of the GFP-expressing B cells (>90%), while cells electroporated with GFP only surivived. Cell death was associated with c-Myc overexpression and visible by the appearance of apoptotic bodies.

Discussion c-Myc/IgH-Carrying EEs Represent an Alternative Mechanism of c-Myc Overexpression in DCPC21 Plasmacytoma.

In the present study, there was demonstrated, by classical cytogenetics, chromosome painting, FISH and SKY, that the DCPC21 plasmacytoma lacks any of the chromosomal translocations involved in the deregulation of the c-myc gene in this malignancy. The presence of extrachromosomal c-myc and IgH-carrying EEs in this tumor raised the question whether these EEs could replace the function of chromosomal translocation in PCT-genesis. A series of experimental approaches have confirmed that the c-myc/IgH-carrying EEs are functional genetic units capable of c-myc transcription.

The evidence that the deregulated expression of c-Myc in the DCPC21 plasmacytoma can be attributed to DCPC21-EEs is further supported by the presence of H3P histone, by c-myc mRNA tracks derived from the EEs, and by extrachromosomal gene transfer studies. The phosphorylated form of histone H3 (H3P) is associated with active chromatin found during transcription and replication (Juan et al., 1998, Juan et al., 1999, Wei et al., 1999). The mRNA-track studies followed by FISH show that the c-myc gene is transcribed in the EEs and this confirms that the generation of Myc RNA initiates outside the chromosomal location of the c-myc gene. The later was further confirmed by extrachromosomal gene transfer experiments. The introduction of DCPC21-EEs into primary mouse B cells was associated with c-Myc overexpression in the electroporated cells and was followed by cell death.

Based on the above findings, it was concluded that the deregulation of c-Myc in plasmacytomas can occur by a mechanism alternative to chromosomal translocation or viral insertion. This novel pathway of c-Myc deregulation involves the formation of extrachromosomal elements that allow c-Myc deregulation similar in extent to that of juxtaposed Ig/myc sequences generated by chromosomal translocation in conventional plasmacytomas.

Models for the Generation of DCPC21-EEs Carrier of Myc/Pvt-1 and IgH Sequences.

Extrachromosomal DNA is found in all organisms analyzed to date (for review see, Gaubatz, 1990). Normal cells seem to carry repetitive sequences on their extrachromosomal DNA and their role in the cells as well as their mechanisms of generation have been widely discussed, but are essentially unknown. EEs can be generated transiently during normal developmental processes (Iwasato et al., 1990; Matsuoka et al., 1990). The size of extrachromosomal elements (EEs) varies (Brothman et al, 1987; Gaubatz, 1990; Gaubatz et al., 1990) as does their number which increases following genotoxic treatments (Cohen et al., 1996; Cohen et al., 1997; Regev et al., 1998). Tumor cells often harbour EEs (Wahl, 1989; Cox et al., 1965). Some of the genes found on EEs have been studied; they include oncogenes and drug resistance genes (Fegan et al., 1995; Wullick et al., 1993; Chen et al., 1989; Delinassios et al., 1983; Rowland et al., 1985; Stahl et al., 1992; Wettergren et al., 1995).

Previous work has indicated that a T(Janz et al., 1997; Wnag et al., 1971) translocation-carrying plasmacytoma cell line, MOPC26S, also contains c-myc and pvt-i genes in duplicated units on chromosome 15 and on extrachromosomal elements (Mai et al., 1995). However, DCPC21-EEs represent the first reported case of functional c-myc-transcribing genetic units in a plasmacytoma that allow c-Myc expression to initiate outside the chromosomes, i. e., the usual chromosomal translocation units. The presence of c-myc/IgH-containing EEs raises the question about the mechanism(s) that account for their formation in the DCPC21 plasmacytoma.

Model 1 assumes a transposition/insertion of myc/pvt-i into the IgH locus on chromosome 12, followed by the release of the juxtaposed sequences from chromosome 12 and their survival as EEs. This model requires one single illegitimate recombination event between c-myc and IgH leading to their juxtaposition on chromosome 12 only, followed by their release from chromosome 12. In the present study, none of the approaches applied detected an insertion of chromosome 15-derived sequences into chromosome 12.

Model 2 proposes reciprocal chromosomal translocation between IgH and c-myc genes. The juxtaposed unit is released from the reciprocally translocated chromosomes T(Janz et al. 1997; Wang et al., 1971) and T(Wang et al., 1971; Janz et al. 1997) in the from of independently replicating EEs. This model, although probable, requires additional molecular events to be consistent with the experimental data obtained in this work. For example, one predicts to find that all EEs contained both c-myc and IgH. Since EEs of various sizes are found which carry both c-myc and IgH or either one alone, replication, recombination and/or breakage of extrachromosomal DNA would have to occur.

Model 3 assumes the independent generation of myc/pvt-i and IgH-carrying EEs that recombine to generate myc/Ig-carrying EEs. This model postulates the sequence of two events, namely the recombination between c-myc- and IgH-containing EEs that were generated concomitantly. Such illegitimate extrachromosomal recombination events are not unlikely, since Ig-sequences-containing EEs are generated as circular extrachromosomal elements during switch recombination in normal B cell development (Iwasato et al., 1990). Following such recombination(s), selective processes allow survival of those extrachromosomal units that confer a growth/survival advantage to the DCPC21 tumor cells. Those EEs that allow deregulated c-Myc expression presumably have favored DCPC21 tumor growth. This model is most consistent with the data obtained. In the absence of any detectable chromosomal translocation involving c-myc and Ig loci, EEs of various sizes were found by hybridizing with C-myc and/or IgH.

Currently, the significance of EEs for tumorigenesis is poorly understood, although they are present in a variety of human tumors and presumably involved either in the initiation of the tumorigenic process or during tumor progression (Trent et al., 1986; Martinsson et al., 1988; Von Hoff et al, 1988). The elimination of amplified c-myc or N-myc located on double minutes from human and mouse tumors contributes to the reduction of tumorigenicity in vitro and in vivo. These studies provided the first indication that EEs can be involved either in initiation or progression of malignancy. Recently, it has been suggested that the amplification of the rearranged C-myc gene and its integration into novel chromosomal sites can involve the formation of extrachromosomal elements (Coleman et al., 1999).

A large number of human neoplasia were found to belong (Von Hoff et al., 1992; Eckhardt et al., 1994; Shimizu et al., 1994) to the translocation negative group. Recent analyses of a series of chronic myelogenous leukemia (CML) revealed an incongruity between the overexpression of the oncogenic fusion product involved in malignant transformation of the precursor cell, and the absence of cytogenetically detectable T(Ohno et al., 1989; Kuschak et al., 1999)(q34;q11) carrier Philadelphia (Ph) chromosome (van der Plas et al., 1989; Kurzrock et al., 1990; Costello et al., 1995; Selleri et al., 1990; Janssen et al., 1992; Estop et al., 1997). In a recent study of adult and childhood acute lymphoblastic leukemia (ALL), the authors investigated the relationship between the T(Muller et al, 1995; Merwin et al., 1963) translocation and the overexpression of the MLL-AF4 gene implicated in the leukemogenesis of infant ALL (Uckun et al., 1998). Nested polymerase chain reaction (NT-PCR) revealed that in 7 out of 18 patients, the generation of the chimeric oncogenic MLL-AF4 protein occurs without cytogenetically detectable T(Muller et al., 1995 ;Merwin et al., 1963) translocation. As in mouse PCTs and rat immunocytomas, Burkitt lymphomas (BLs) are also carrier of Ig/myc-juxtaposed sequences resulting from chromosomal translocation between myc and Ig gene carrier chromosomes (for review see, Klein, 1989; Klein, 1993; Klein, 1995). Notably, in one of the translocation-negative BLs that were analyzed, c-Myc overexpression was found similar to that found in translocation-carrying BLs. c-myc and IgH sequences were found on EEs, and the c-myc gene was germ line.

In conclusion, the results provide evidence that the EEs represent functional genetic units that play essential roles both in the initiation and/or promotion of the malignant phenotype of the translocation-negative DCPC21 plasmacytoma. The findings also show that different experimental and human neoplasms with fusion transcripts or oncogenic activation, although cytogenetically classified as "translocation-negative", can indeed carry specific translocation(s), however in an extrachromosomal form.

Obviously, many modifications and variations of the present invention are possible in light of the above teachings and following Examples. It is, therefore, to be understood that within the scope of the described invention, the invention can be practiced otherwise than as specifically described.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

TABLE 1

Myc protein levels as determined by quantitative fluorescent immunohistochemistry.

|           | Negative | Myc+ | Myc++ | Myc+++ | Total |
|-----------|----------|------|-------|--------|-------|
| Negative  | 5        | 4    | 0     | 1      | 10    |
| CIN1      | 1        | 7    | 0     | 2      | 11    |
| CIN2      | 0        | 4    | 1     | 0      | 4     |
| CIN3      | 1        | 4    | 2     | 3      | 10    |
| Carcinoma | 0        | 0    | 0     | 1      | 1     |
| Total     | 7        | 19   | 3     | 7      | 36    |

TABLE 2

DHFR gene copy numbers in cervical neoplasia as determined by FISH.

|           | DHFR− | DHFR+/− | DHFR+ | DHFR++ | DHFR+++ | Total |
|-----------|-------|---------|-------|--------|---------|-------|
| Negative  | 2     | 3       | 0     | 2***   | 0       | 7     |
| CIN1      | 3     | 2       | 2     | 0      | 0       | 8     |
| CIN2      | 0     | 1       | 1     | 3      | 0       | 4     |
| CIN3      | 0     | 0       | 0     | 4      | 5       | 9     |
| Carcinoma | 0     | 0       | 0     | 0      | 1       | 1     |
| Total     | 5     | 6       | 3     | 9      | 6       | 29    |

*Pap was CIN3
**Strong maplification in limited areas

References

Mai S., Hanley-Hyde J. and Fluri M. C-Myc overexpression associated DHFR gene amplification in hamster, rat, mouse and human cell lines. Oncogene, 12:277–288 (1996).

Luecke-Huhle C., Mai S. and Moll J. C-myc overexpression facilitates radiation-induced DHFR gene amplification. Int. J. Radiat. Biol., 71:167–175 (1997)

Mai S., Fluri M., Siwarski D. and Huppi, K. Genomic instability in MycER-activated Rat1A0MycER cells. Chromosome Res. 4:365–371 (1996).

Fukasawa, K., Wiener, F., Vande Woude, G. F., and Mai, S. Genomic instability and apoptosis are frequent in p53 deficient young mice. Oncogene, 15:1295–1302 (1997).

Inaba, T., Matsushime, Valentine, M., Roussel, M. F., Sherr, C. J. & Look, A. T. Genomic organization, chromosomal localization, and independent expression of human cyclin D genes. Genomics 13:565–574 (1992).

O'Brief S., del Giglio A., Keating M. Advances in the biology and treatment of B-cell chronic lymphocytic leukemia. Blood 85:307–318 (1995).

Rai J. L., Sawitsky A., Cronkite E. P., Chanana A. D., Levy R. N., Pasternack, B. S. Clinical staging of chronic lymphocytic leukemia. Blood 46:219–234 (1975).

Montserrat E., Sanchez-Bisono, J., Vinolas, N. and Rozman, C. Lymphocyte doubling time in chronic lymphocytic leukemia. Analysis of its prognostic significance. Br. J. Haematol. 62:567–575 (1986).

Schena, M., Larsson, L. G., Gottardi, D., et al. Growth- and differentiation-associated expression of bcl-2 in B-chronic lymphocytic leukemia cells. Blood 79:2981–2989 (1992).

Hanada M., Delia, D., Aiello, A., Stadtmauer, E., Reed, J. C. Bcl-2 gene hypomethylation and high-level expression in B-cell chronic lymphocytic leukemia. Blood 82:1820–1828 (1993).

Johnston, J. B., Daeninck, P., Verburg, L., Lee, K., Williams, G., Israels, L. G., Mowat., M. R. A., and Begleiter, A. P53, MDM-2, Bax and Bcl-2 and drug resistance in chronic lymphocytic leukemia. Leuk. Lymph. 26435–449 (1997).

Juliusson, G., Gahrton, G. Chromosome abnormalities in B-cell chronic lymphocytic leukemia. In: Cheson B. D., ed. Chronic lymphocytic leukemia; Scientific advances and clinical developments. Marcel Dekker, Inc. 83–103 (1993)

Juliusson, G., Oscier, D. G., Fitchett, M., et al. Prognostic subgroups in B-cell-chronic lymphocytic leukemia defined by specific chromosome abnormalities. N. Engl. J. Med. 323:720–724 (1990).

Geisler, C., Philip, P., Hansen, M. B-cell chronic lymphocytic leukemia: Clonal chromosome abnormalities and prognosis in 89 cases. Eur. J. Haematol. 43:397–403 (1989).

Oscier, D. G., Stevens, J., Hamblin, T. J., Pickering, T. M., Lambert, R., Fitchett, M. Correlation of chromosome abnormalities with laboratory features and clinical course in B-cell chronic lymphocytic leukaemia. Br. J. Haematol. 76:352–358 (1990).

Kay, N. E., Ranheim, E. A., Peterson, L. C. Tumor suppressor genes and clonal evolution in B-CLL. Leuk. Lymph. 8:416. Kay, N. E., Ranheim, E. A., Peterson, L. C. Tumor suppressor genes and clonal evolution in B-CLL. Leuk. Lymph. 8:41–49 (1995).

Oscier, D., Fitchett, M. Herbert, T., Lambert, R. Karyotypic evolution in B-cell chronic lymphocytic leukaemia. Genes, Chromosomes and Cancer 3:16–20 (1991).

Peterson, L., Blackstadt, M., Kay, N. Clonal evolution in chronic lymphocytic leukemia. In: Cheson B D, ed. Chronic lymphocytic leukemai; Scientific advances and clinical developments. Marcel Dekker, Inc. 181–196 (1993).

Crossen, P. D. Genes and chromosomes in chronic B-cell leukemia. Cancer Genetics Cytogenetics 94:45–51 (1997).

Dohner, H. et al. 11q deletions identify a new subset of B-cell chronic lymphocytic leukemia characterized by extensive nodal involvement and inferior prognosis. Blood 89:2516–2522 (1997)

Corcoran, M. M., Rasool, I., Liu, Y. et al. Detailed molecular delineation of 13q14.3 loss in B-cell chronic lymphocytic leukemia. Blood. 91:1382–1390 (1998).

Kalachikov, Migliazza, Cayanis, E., et al. Clonging and gene mapping of the chromosome 13q14 region deleted in chronic lymphocytic leukemia. Genomics, 42:369–377 (1997).

Matutes, E., et al. Trisomy 12 defines a group of CLL with atypical morphology: correlation between cytogenetic, clinical and laboratory features in 544 patients. Br. J. Haematol, 92:382–388 (1996).

El Rouby, S., et al. p53 gene mutation in B-cell chronic lymphocytic leukemia is associated with drug resistance and is independent of MDR1/MDR3 gene expression. Blood 82:3452–3459 (1993).

Dohner, H., et al. p53 gene deletion predicts for poor survival therapy with purine analogs in chronic B-cell leukemias. Blood 85:1580–1589 (1995).

Garcia-Marco J. A., Caldas, C., Price C. M., Weidemann, L. M., Ashworth, A., Catovsky, D. Frequent somatic deletion of the 13q12.3 locus encompassing BRCA2 in chronic lymphocytic leukemia. Blood 88:1568–1575 (1996).

Santelli, R. V., Machando-Santelli, G. M., Peuyo, M. T., Navarro-Cattapan, L. D> and Lara F. J. S. Replication and transcription in the course of DNA amplification of the C3 and C8 puffs of Rhynchosciara americana. Mech. Dev. 36:59–66 (1991).

Delikadis, C. and Kafatos, F. C. Amplification enhancers and replication origins in the autosomal chorion cluster of Drosophila. The Embo. J. 8:891–901 (1989).

Stark, Y. and Wahl, G. M. Gene amplification. Ann. Rev. Biochem. 53:447–491 (1984).

Prody, C. A., Dreyfus, P., Zamir, R., Zakut, H. and Soreq, H. De novo amplification within a "silent" human cholinesterase gene in a family subjected to prolonged exposure to organophosphorus insecticides. Proc. Natl. Acad. Sci. USA 86:690–694 (1989).

Lucke-Huhle, C. Review: Gene amplification—a cellular response to genotoxic stress. Mol. Toxicol. 2:237–253 (1989).

Wright, J. A., Smith, H. S., Watt, F. M., Hancock, M. C., Hudson, D. L., and Stark G. R. DNA amplification is rare in normal human cells. Proc. Natl. Acad. Sci. USA 87:1791–1795 (1990).

Tisty, T. D. Normal diploid cells lack a detectable frequency of gene amplification. Proc. Natl. Acad. Sci. USA 87:3132–3136 (1990).

Stark, G. R., Regulation and mechanisms of mammalian gene amplification. Adv. Cancer Res. 61:87–113 (1993).

Huang, A., Jin, H., and Wright, J. A. Aberrant expression of basic fibroblast growth factor in NIH-3T3 cells alters drug resistance and gene amplification potential. Exp. Cell. Res. 213:335–339 (1994).

Huang, A., and Wright, J. A. Fibroblast growth factor mediated alterations in drug resistance and evidence of gene amplification. Oncogene 9:491–199 (1994).

Shah, D. M., Horsch, R. B., Klee, H. J. Kishore, G. M. Winter, J. A., Turner, N. E., Hironaka, C. M., Sanders, P. R., Gasser, C. S., Aykent, S., Siegel, N. R., Rogers, S. G., and Fraley, R. T. Engineering herbicide tolerance in transgenic plants. Science 233:478–481 (1986).

Lucke-Huhle, C. Review: Gene amplification—a cellular response to genotoxic stress. Mol. Toxicol. 2:237–253 (1989).

Lucke-Huhle, C., Pech, M., and Herrlich, P. SV40 CAN amplification and reintegration in surviving hamster cells after 60 Co gamma-irradiation. Int. J. Radiat. Biol. 58:577–588 (1990).

Yalkinoglu, A. O., Zentgraf, H. and Hubscher, U. The origin of adeno-associated virus DNA replication is a target for acrcinogen-induced DNA amplification. J. Virol. 65:3175–3184 (1991).

Mai, S. Overexpression of c-myc precedes amplification of the gene encoding dihydrofolate reductase. Gene 148: 253–260 (1994).

Denis, N., Kitzis, A., Kruh, J., Dautry, F., and Crocos, D. Stimulation of methotrexate resistance and dihydrofolate reductase gene amplification by c-myc. Oncogene 6:145301457 (1991).

Johnston, R. N., Beverley, S. M. and Schmike, R. T. Rapid spontaneous dihydrofolate reductase gene amplification shown by fluorescence-activated cell sorting. Proc. Natl. Acad. Sci USA 80:3711–3716 (1983).

Yin, Y., Tainsky, M. A., Bischoff, F. Z., Strong, L. C. and Wahl, G. M. Wildtype p53 restores cell cycle control and inhibits gene amplification in cells with mutant p53 alleles. Cell 70:937–948 (1992).

Livingstone, L. R., White A., Sprouse, J., Livanos, E., Jacks, T., and Tlsty, T. D. Altered cell cycle arrest and gene amplification potential accompany loss of wildtype p53. Cell 70:923–935 (1992).

Van Der Bliek, A. M., Van Der Velde-Koerts, T., Ling, V., Borst, P. Overexpression and amplification of five genes in a multidrug-resistant Chinese hamster ovary line. Mol. Cell. Biol. 6:1671–1678 (1986).

Zhou, P., Jiang, W., Wergost, C. M., Weinstein, I. B., Overexpression of cyclin D1 enhances gene amplification. Cancer Res. 56:36–39 (1996).

Schwab, M. and Amler, L. C. Amplification of cellular oncogenes. A predictor of clinical outcome in human cancer. Genes Chromosomes and Cancer. 1:181–193 (1990).

Hahn, P. J. Molecular biology of couble minute chromosomes. BioEssays. 15:477–484 (1993).

Stark, G. R., Debatisse, M., Giulotto, E., and Wahl, G. M. Recent progress in understanding mechanisms of mammalian DNA amplification. Cell. 57:901–908 (1989).

Carroll, S. M., DeRose, M. L., Gaudray, P., Moore, C. M. Needham-Vandevanter, D. R., Von Hoff, and Wahl, G. Double minute chromosomes can be produced from precursors derived from a chromosomal deletion. Mol. Cell. Biol. 8:1525–1533 (1988).

Windle, B., Draper, B. W., Yin, Y, O'Gorman, S. and Wahl, G. M. A central role for chromosomes breakage in gene amplification, deletion formation, and amplicon integration. Genes Dev. 5:160–174 (1991).

Hamkalo, B. a. Farmham, P. J., Johnston, R., and Schimke, R. T. Ultrastructural features of minute chromosomes in a methotrexate-resistant mouse 3T3 cell line. Proc. Natl. Acad. Sci. USA 82:1126–1130 (1985).

Esnault, C., Lee, H. and Lai, E. Structure and organization of a stable extrachromosomal element in human cells. Gene. 144:205–211 (1994).

Anderson, R. P. and Roth, J. R. 1977. Tandem genetic duplications in phage and bacteria. Annu. Rev. Microbiol. 31: 473–505.

Ariyama, Y., Sakabe, T., Shinomiya, T., Mori , T., Fukuda, Y., and Inazawa, J. 1998. Identification of amplified DNA sequences on double minute chromosomes in a leukemic cell line KY821 by means of spectral karyotyping and comparative genomic hybridization. J. Hum. Genet. 43:187–190.

Brodeur, G. M. and M. D. Hogarty 1998. pp. 161–179. In .K. Kinzler, W. Brodeur, and B. Vogelstein (Eds.) *The Genetic Basis of Human Cancer* 1st Ed. McGraw-Hill New York., N.Y.

Cohen, S., Regev, A., and Lavi, S. 1997. Small polydispersed circular DNA (spc DNA) in human cells: association with genomic instability. Oncogene 14: 977–985.

Coller, H. A., Grandori, C., Tamayo, P., Colbert, T., Lander, E. S., Eisenman, R. N., and Golub, T. R. 2000. Expression analysis with oligonucleotide microarrays reveals that MYC regulates genes involved in growth, cell cycle, signaling, and adhesion. Proc. Natl. Acad. Sci. USA 97:3260–3265.

Cowell, J. K. 1982. Double minutes and homogeneously staining regions: gene amplification in mammalian cells. Annu. Rev. Genet. 16: 21–59.

Fidler, I. J. and Hart, I. R. 1982. The development of biological diversity and is metastatic potential in malignant neoplasms. Oncodev. Biol. Med. 4:161–76.

Gaubatz, J. W. and Flores, S. C. 1990. Purification of eucaryotic extrachromosomal circular DNAs using exonuclease III. Analyt. Biochem. 184, 305–310.

Hamlin, J. L., Leu, T. H., Vaughn, J. P., Ma, C., and Dijkwel, P. A. 1991. Amplification of DNA sequences in mammalian cells. Prog. Nucleic Acid Res. Mol. Biol. 41:203–239.

Hirt, B. 1967. Selective Extraction of Polyoma DNA from Infected Mouse Cell Cultures. J. Mol. Biol. 26: 365–369.

Kallioniemi, A., Kallioniemi, O. P., Sudar, D., Rutovitz, D., Gray, J. W., Waldman, F., and Pinkel, D. 1992. Comparative genomic hybridization for molecular cytogenetic analysis of solid tumors. Science. 258: 818–821.

Khaira, P., James, C. D., and Leffak, M. 1988. Amplification of the translocated c-myc genes in three Burkitt lymphoma cell lines. Gene. 211: 101–8.

Kuschak, T. I., Paul, J. T., Wright, J. A., Mushinski, J. F., and Mai, S. 1999. FISH on purified extrachromosomal DNA molecules. TTO http://biomednet.com/db/tto. TO1669.

Kuschak, T. I., Taylor, C. T., Mushinski, J. F., Henderson, D. W., Israels, S., McMillan-Ward, E., Wright, J. A., and Mai, S. 1999. The ribonucleotide reductase R2 gene is a non-transcribed target of c-Myc-induced genomic instability. Gene 238: 351–365.

Mai, S. 1994. Overexpression of c-myc precedes amplification of the gene encoding dihydrofolate reductase. Gene 148: 253–260.

Mai, S., Hanley-Hyde J., Rainey J., Kuschak, T. I., Fluri M., Taylor C., Littlewood T. D., Mischak H., Stevens L. M., Henderson D. W., and Mushinski J. F. 1999. Chromosomal and extrachromosomal instability of the cyclin D2 gene is induced by Myc overexpression. Neoplasia, 1: 241–252.

Mai, S., Hanley-Hyde, J., and Fluri, M. 1996. c-Myc overexpression associated DHFR gene amplification in hamster, rat, mouse and human cell lines. Oncogene 12: 277–288.

Nowell, P. C. 1976. The clonal evolution of tumor cell populations. Science 194: 23–28.

Regev, A., Cohen, S., Cohen, E., Bar-Am, I. and Lavi, S. 1998. Telomeric repeats on small polydisperse circular DNA (spcDNA) and genomic instability. Oncogene 17: 3455–3461.

Sanchez, A. M., Barrett, J. T., and Schoenlein, P. V. 1998. Fractionated ionizing radiation accelerates loss of amplified MDR1 genes harbored by extrachromosomal DNA in tumor cells. Cancer Res. 58: 3845–3854.

Schimke, R. T. 1984. Gene amplification in cultured animal cells. Cell 37: 705–713.

Schimke, R. T. 1988. Gene amplification in cultured cells. J. Biol. Chem. 263:5989–5992.

Stark, G. R. 1993. Regulation and mechanisms of mammalian gene amplification. Adv. Cancer Res. 61: 87–113

Stark, G. R. and Wahl, G. M. 1984. Gene amplification. Ann Rev. Biochem. 53: 447–491.

Szeles A., Kerstin, I., Falk, S. I., and Klein, G. 1999. Visualization of alternative Epstein-Barr Virus expression programs by fluorescent in situ hybridization at the cell level. J. Virol. 73: 5064–5069.

Taylor, C. and Mai, S. 1998. c-Myc-associated genomic instability of the dihydrofolate reductase locus in vivo. Cancer Detect. Prev. 22: 350–356.

Tisty T. D., 1990. Normal diploid human and rodent cells lack a detectable frequency of gene amplification. Proc. Natl. Acad. Sci. USA. 87: 3132–3136.

Tisty, T. D., Margolin, B. H., and Lum, K. 1989. Differences in the rates of gene amplification in nontumorigenic and tumorigenic cell lines as measured by Luria-Delbruck fluctuation analysis. Proc. Natl. Acad. Sci. USA. 86: 9441–9445.

Von Hoff, D. D. 1991. New mechanisms of gene amplification in drug resistance (the episome model). Cancer Treat. Res. 57:1–11.

Wiener, F., Kuschak, T. I., Ohno, S., and Mai, S. 1999. Deregulated expression of c-Myc in a translocation-negative plasmacytoma on extrachromosomal elements that carry IgH and myc genes. Proc. Natl. Acad. Sci. USA. 96: 13967–13972.

Wright, J. A., Smith, H. S., Watt, F. M., Hancock, M. C., Hudson, D. L., and Stark, G. R. 1990. DNA amplification is rare in normal human cells. Proc Natl. Acad. Sci. USA 87:1791–1795.

Nonet, G. H., Carroll, S. M., DeRose, M. L., and Wahl, G. M. Molecular dissection of an extrachromosomal amplicon reveals a circular structure consisting of an imperfect inverted duplication. Genomics. 15:543–558 (1993).

Sen, S., Sen., P., Mulac-Jericevic, B., Zhou, H. Pirrotta, V., and Stass, S. A. Microdissected double-minute DNA detects variable patterns of chromosomal localizations and multiple abundantly expressed transcripts in normal and leukemic cells. Genomics, 19:542–551 (1994)

Schneider, S. S., Heimstra, J. L., Zehnbauer, B. A., Taillon-Miller, P., Le Paslier, D. L., Vogelstein, B., and Brodeur, G. M. Isolation and structural analysis of a 1.2-megabase N-myc amplicon from a human neuroblastoma. Mol. Cell. Biol. 12:5563–5570 (1992).

Cohen, S., Regev, A., Lavi, S. Induction of circles of heterogeneous sizes in carcinogen-treated cells: Two dimensional gel analysis of circular DNA molecules. Mol. Cell Biol., 16:2002–2014 (1996).

Cohen, S., Regev, A., Lavi, S. Small poorly dispersed circular DNA (spc DNA) in human cells: Associated with genomic instability. Oncogene. 14:977–985 (1997).

Bentz, M., Huck, K. du Manior, S., Joos, S., Werner, D. A., Fischer, K. Dohner, H., and Lichter, H. Comparative genomic hybridization in chronic B-cell leukemias shows a high incidence of chromosomal gains and losses. Blood. 85:3610–3618 (1995).

Merup, M., Juliusson, G., Wu, X., Jansson, M. Stellan, B., Rascool, O., Roijer, E., Stenman, G., Gahrton, G., and Einhorn, S. Amplification of multiple regions of chromosome 12, including 12q13–15, in chronic lymphocytic leukemia. Eur. J. Haematol, 58:174–180 (1997).

Wang, T., Samples, D. M., Doub, R., and Prakash, O. c-myc and K-ras-2 oncogenes in B cell chronic lymphocytic leukemia with del (12(P13)). Cancer Gent. Cytogenet, 51:125–130 (1991).

Greil, R., Fasching, B., Loidl, P. and Huber H. Expression of the c-myc protooncogene in multiple myeloma nad chronic lymphocytic leukemia: An in situ analyssi. Blood. 78:180–191 (1991).

Sherr, C. J. G1 phase progression: Cycling on due. Cell, 79:551–555 (1994).

Hirama, T., Koeffler, H. P. Role of the cyclin-dependent kinase inhibitors in the development of cancer. Blood, 86:841–854 (1995).

Delmer, A. Ajchenbaum-Cymbalista, F., Tang, R., Raymond, S., Faussat, A-M., Marie, J-P and Zittoun, R. et al. Overexpression of cyclin Dw in chronic B-cell malignancies. Blood. 85:2870–2876 (1995).

Byrd, J. C., Shimm, C. A. Bedi, A., Waselanko, J. K. Fuchs, E., Flinn, IW, Diehl, L. F., Sausville, E., and Grever, MR> Flavopiridol has marked in vitro activity against human B-chronic lymphocytic leukemia and induces apoptosis independent of p53 status. Blood, 90:401a (1997).

Ando, K, Ajchenbaum-Cymbalista, F and Griffin J D. Regulation of G1/S transition by cyclins D2 and D3 in hematopoietic cells. Proc. Natl. Acad. Sci. (USA), 90: 9571–9575. 1993.

Kato, J-Y, and Sherr, C J Inhibition of granulocyte differentiation by G1 cyclins D2 and D3 but not D1. Proc Natl Acad Sci (USA), 90: 11513–11517, 1993.

Vrhovac, R, Delmer, A, Tang, J P, Marie, J P, Zittoun, R and Ajchenbaum-Cymbalista, F. The expression of cell cycle inhibitor p27$^{kip1}$ has a prognostic significance and influences apoptosis in B cell chronic lymphocytic leukemia. Blood, 90:91a, 1997.

Muller, D, Bouchard, C, Rudolph, B, Steiner, P, Stuckmann, I, Saffrich, R, Ansorage, W, Huttner, W and Eilers, M. CDK2 dependent phosphorylation of p27 facilitates its Myc-induced release from cyclin E/CDK2 complexes. Oncogene, 15:2561–2576, 1997.

Blain, S W, Montalvo, E, Massague, J. Differential interaction of the cyclin-dependent kinase (CDK) inhibitor p27$^{kip1}$ with cyclinA-Cdk2 and cyclinD2-cdk4. J Biol Chem, 272:25863–25872,1997.

Kawamata, S, Sakaida, H, Hori, T, Maeda, M and Uchiyama, T. The upregulation of p27$^{kip1}$ by Rapamycin results in G1 arrest in exponentially growing T-cell lines. Blood, 91:561–569, 1998.

Wang, X, Gorospe, M, Huang, Y and Holbrook, N.J. p27$^{kip1}$ overexpression causes apoptotic death of mammalian cells. Oncogene, 15:2991–2997, 1997.

Hoglund, M, Johansson, B, Pedersen-Bjergaard, J, Marynen, P and Mitelman, F. Molecular characterization of 12p abnormalities in hematological malignancies: Deletion of KIP1, rearrangement of TEL, and amplification of CCND2. Bloo, 87:324–330, 1996.

Taylor, C, and Mai, S. C-Myc associated genomic instability of the DHFR locus in vivo. Cancer Detection and Prevention 1998. (in press).

Hirt B: Selective extraction of polyoma DNA from infected mouse cell cultures. J Mol Biol, 26:365,1967.

De Cremous, P, Thious, M, Peter, M, Vielh, P, Michon, J, Delattre, O and Magdelenat, H. Polymerase chain reaction compared with dot blotting for the determination of N-myc gene amplification in enuroblastoma. Int J Cancer, 72:518–521, 1997.

Lawrence, J B, Singer, R H and Marselle, L M. Highly localized tracks of specific transcripts within interphase nuclei visualized by in situ hybridization. Cell, 57:493–402, 1989.

Wijgerde, M, Grosveld, F and raser, P. Transcription complex stability and chromatin dynamics in vivo. Nature, 377:209–213, 1996.

Ashe, H L, Monks, J, Wijgerde, M, Fraser, P and Proudfoot, N. J. Intergenic transcription and transinduction of the human b-globin locus. Genes and Development, 11:2494–2509,1997.

Lukas, J, Bartkova, L J, Welcker, M, Petersen, O W, Peters, G, Strauss, M, and Bartek, J. Cyclin D2 is a moderately oscillating nucleoprotein required for G1 phase progression in specific cell types. Oncogene, 10:2125–2134, 1995.

Larsson L-G, Schena M, Carlsson M, Sallstrom J and Nilsson K. Expression of the c-myc protein is down-regulated at the terminal stages during in vitro differentiation of B-type chronic lymphocytic leukemia cells. Blood 77:1025–1032,1991.

Kubbies, M, Schindler, D, Hoehn, H, and Rabinovitch, P S. BrdU-Hoechst flow cytometry reveals regulation of human lymphocyte growth by donor-age-related growth fraction and transition rate. J Cell Physiol, 125:229–234, 1985.

Schindler, D, Kubbies, M, Hoehn, H, Schinzel, A and Rabinovitch, P S. Confirmation of Fanconi's anemia and detection of a chromosomal aberration (1Q12–32 triplication) via BrdU/Hoechst flow cytometry. Am J Ped Hematol Oncol, 9:172–177, 1987.

Anazodo, M I, Duta, E, Friesen, A D and Wright, J A. Relative levels of inhibition of p24 gene expression by different 20-mer antisense oligonucleotide sequences targeting nucleotides +1129 to +1268 of the HIV-1 gag genome: An analysis of mechanism. Bioch Biophys Res Comm, 229:305–309, 1996.

Mai S and Zjalava A. C-Myc binds to 5' flanking sequence motifs of the dihydrofolate reducatase gene in cellular extracts: Role in proliferation. Nucl Acid Res. 22:2264–2273. 1994.

Fry, C J, Slansky, J E and Farnham, P J. Position-dependent transcriptional regulation of the murine dihydrofolate reductase promoter by the E2F transactivation domain. Mol Cell Biol, 17:1966–1976, 1997.

Zheng, C Y, Pabello, P, Maksymiuk, A W and Skinnider, L F. Establishment of cell lines derived from chronic lymphocytic leukaemic cells by transfection with my cand ras. Br J Haematol, 93:681–683,1996.

Harlow, E and Lane, D. 1988. Antibodies: A Laboratory Manual. Cold Spring Harbor Laboratory, Cold Spring Harbor.

Jun, D Y, Kim, M-K, Kim, I-G and Kim, Y H. Characterization of the murine cyclin D2 gene. Exon/intron organization and promoter activity. Mol Cells, 7:537–543, 1997.

Brooks, A R, Shiffman, D, Chan, C S, Brooks, E E, and Milner, P G. Functional analysis of the human cyclin D2 and cyclin D3 promoters. J Biol Chemistry, 271:9090–9099,1996.

Reynisdottir, I, Massague, J. The subcellular locations of p15(Ink4b) and p27$^{(kip1)}$ coordinate their inhibitory interactions with cdk4 and cdk2. Genes Dev, 11:492–503, 1997.

Bosc, D G, Slominski, E, Sichler, C and Litchfield, D W Phophorylation of casein kinse II by p34cdc2. Identification of phosphorylation sites using phosphorylation site mutants in vitro. J Biol Chem, 270:25872–25878, 1995.

Neubauer, A, De Kant, E, Rochlitz, C, Laser, J, Zanetta, A M, Gallardo, J, Oertel, J, Herrmann, R and Huhn, D. Altered expression of the retinoblastoma susceptibility gene in chronic lymphocytic leukaemia. Br J Haematol, 85:498–503,1991.

Kornblau, S M, Chen, N, del Giglio, A, O'Brien, S and Deisseroth, A B. Retinoblastoma protein expression is frequently altered in chronic lymphocytic leukemia. Cancer Res, 54:242–246, 1994.

Ganter, B, Fu, S and Lipsick, J S. D-type cyclins repress transcriptional activation by the v-Myb but not the c-Myb DNA-binding domain. The EMBO J., 17:255–268. 1998.

Rosenber, N and Baltimore, D. A quantitative assay for transformation of bone marrow cells by Abelson Murine Leukemia Virus. J Exp Med, 143:1453–1463, 1976.

Graham, F L and Prevec, L. Manipulation of adenovirus vectors. Methods in Mol Biol, 7:109–128, 1991.

Santelli, R. V., Machado-Santelli, G. M., Pueyo, M. T., Navarro-Cattapan, L. d., and Lara, F. J. S. (1991). Replication and transcription in the course of DNA amplification of the C3 and C8 puffs of *Rhynochosciara americana*. Mech. Dev. 36: 59–66, 1991.

Delikadis, C. and Kafatos, F. C. (1989). Amplification enhancers and replication origins in the autosomal chorion cluster of *Drosophila*. The EMBO J. 8: 891–901.

Stark, G. R. and Wahl, G. M. (1984). Gene amplification. Ann Rev. Biochem., 53, 447–491.

Yokota, Y., Tsunetsugu-Yokota, Y., Battifora, C. L., and Cline, M. J. (1986). Alterations in myc, myb, ras Ha proto-oncogenes in cancers are frequent and show clinical correlation. Science 231: 261–265.

Mai, S., Hanley-Hyde, J., Fluri, M. (1966). c-Myc overexpression associated DHFR gene amplification in hamster, rat, mouse and human cell lines. Oncogene 12: 277–288.

Mai, S., Fluri, J., Siwarski, D., Huppi, K. (1996). Genomic instability in MycER activated Rat1A-MycER cells. Chromosome Research 4: 365–372.

Mai, S., Hanley-Hyde, J., Coleman, A., Siwarski, D., Huppi, K. (1995). Amplified extrachromosomal elements containing c-Myc and Pvt 1 in a mouse plasmacytoma. Genome 38: 780–85.

Van Der Bliek, A. M., Van Der Velde-Koerts, T., Ling, V., Borst, P. (1986). Overexpression and amplification of five genes in a multidrug-resistant Chinese hamster ovary line. Mol. Cell. Biol. 6: 1671–1678.

Corvi, R., Amler, L. C., Savelyeva, L., Gehring, M., Schwab, M. (1994). MycN is retained in single copy at chromosome 2 band p23–23 during amplification in human neuroblastoma. Proc. Natl. Acad. Sci. (USA) 91: 5523–5527.

Stark, G. R. (1993). Regulation and mechanisms of mammalian gene amplification. Adv. Cancer Res. 61: 87–113.

Schimke, R. T., Kaufman, R. J., Alt, F. W., and Kellems, R. F. (1978). Gene amplification and drug resistance in cultured murine cells. Science 202: 1051–1055.

Shah, D. M., Horsch, R. B., Klee, H. J., Kishore, G. M., Winter, J. A., Turner, N. E., Hironaka, C. M., Sanders, P. R., Gasser, C S., Aykent, S., Siegel, N. R., Rogers, S. G., and Fraley, R. T. (1986). Engineering herbicide tolerance in transgenic plants. Science 233: 478–481.

Huang, A. and Wright, J. A. (1994). Fibroblast growth factor mediated alterations in drug resistance, and evidence of gene amplification Oncogene 9: 491–499.

Huang, A., Jin, H., and Wright, J. A. (1994). Aberrant expression of basic fibroblast growth factor in NIH-3T3 cells alters drug resistance and gene amplification potential. Exp. Cell Res. 213: 335–339.

Huang, A., Jin, H., and Wright, J. A. (1995). Drug resistance and gene amplification potential regulated by transforming growth factor-β 1 gene expression. Cancer Res. 55: 1758–1762.

Lavi, S. (1981) Carcinogen-mediated amplification of viral DNA sequences in simian virus 40-transformed Chinese hamster embryo cells. Proc. Natl. Acad. Sci. (USA) 78: 6144–6148.

Tlsty, T. D., Brown, P. E., and Schimke, R. T. (1984). UV radiation facilitates methotrexate resistance and amplification of the dihydrofolate reductase gene in cultured mouse cells. Mol. Cell. Biol. 4 1050–1056.

Lücke-Huhle, C., Pech, M., and Herrlich, P. (1990). SV40 DNA amplification and reintegration in surviving hamster cells after 60 Co gamma-irradiation. Int. J. Radiat. Biol. 58: 577–588.

Yalkinoglu, A. Ö., Zentgraf, H., and Hübscher, U. (1991). The origin of adeno-associated virus DNA replication is a target for carcinogen-induced DNA amplification. J. Virol. 65: 3175–3184.

Lücke-Huhle, C., (1989). Review: gene amplification—a cellular response to genotoxic stress. Mol. Toxicol. 2: 237–253.

Mai, S. (1994). Overexpression of c-myc precedes amplification of the gene encoding dihydrofolate reductase. Gene 148: 253–260.

Denis, N., Kitzis, A., Kruh, J., Dautry, F., and Crocos, D. (1991). Stimulation of methotrexate resistance and dihydrofolate reductase gene amplification by c-myc. Oncogene 6:1453–1457.

Johnston, R. N., Beverley, S. M., and Schimke, R. T. (1983). Rapid spontaneous dihydrofolate reductase gene amplification shown by fluorescence-activated cell sorting. Proc. Natl. Acad. Sci. (USA) 80: 3711–3715.

Prody, C. A., Dreyfus, P., Zamir, R., Zakut, H., and Soreq, H. (1989). De novo amplification within a "silent" human cholinesterase gene in a family subjected to prolonged exposure to organophosphorus insecticides. Proc. Natl. Acad. Sci. (USA) 86: 690–694.

Wright, J. A., Smith, H. S., Watt, F. M. Hancock, M. C., Hudson, D. L., and Stark, G. R., (1990). DNA amplification is rare in normal human cells. Proc. Natl. Acad. Sci. (USA) 87: 1791–1795.

Tlsty, T. D. (1990). Normal diploid cells lack a detectable frequency of gene amplification. Proc. Natl. Acad. Sci. (USA) 87: 3132–3136,1990.

Yin, Y., Tainsky, M. A., Bischoff, F. Z., Strong, L. C., and Wahl, G. M. (1992). Wildtype p53 restores cell cycle control and inhibits gene amplification in cells with mutant p53 alleles. Cell 70: 937–948.

Livingstone, L. R., White, A., Sprouse, J., Livanos, E., Jacks, T., and Tisty, T. D. (1992). Altered cell cycle arrest and gene amplification potential accompany loss of wildtype p53. Cell 70: 923–935.

Zhou, P., Jiang, W., Wegorst, C. M., and Weinstein, I. B. (1996). Overexpression of cyclin D1 enhances gene amplification. Cancer Research 56:36–39.

Marcu, K. B., Bossone, S. A., and Patel, A. J. (1992). Myc function and regulation. Ann. Rev. Biochem. 61: 809–860.

Cole, M. D. (1986). The myc oncogene: its role in transformation and differentiation. Ann. Rev. Genet. 20: 361–384.

Benevisty, N., Leder, A., Kuo, A., and Leder, P. (1992). An enbryonically expressed gene is a target for c-Myc regulation via the c-Myc binding sequence. Genes Dev. 6: 2513–2523.

Bello-Fernandez, C., Packham, G., and Cleveland, J. L. (1993). The ornithin decarboxylase is a transcriptional target of c-Myc. Proc. Natl. Acad. Sci. (USA) 90: 7804–7808.

Gaubatz, S., Meichle, A., and Eilers, M. (1994). An E-box element localized in the first intron mediates regulation of the prothymosin a gene by c-myc. Mol. Cell. Biol. 14: 3853–3862.

Jansen-Dürr, P., Meichle, A., Steiner, P., Pagano, M., Finke, K., Botz, J., Wessbecher, J., Draetta, G., and Eilers, M. (1993). Differential modulation of cyclin expression by MYC. Proc. Natl. Acad. Sci. (USA) 90: 3685–3689.

Daksis, J. I., Lu, R. Y., Facchini, L. M., Marhin, W. W., and Penn, L. J. Z. (1994). Myc induces cyclin D1 expression in the absence of de novo protein synthesis and links mitogen-stimulated signal transduction to the cell cycle. Oncogene 9: 3635–3645,1994.

Philipp, A., Schneider, A., Västrik, I. Finke, K., Xiong, Y., Beach, D., Alitalo, K., and Eilers, M. (1994). Repression of cyclin D1: a novel function of MYC. Mol. Cell. Biol. 14: 4032–4043.

Galaktionov, K., Chen, X., and Beach, D. (1996). Cdc25 cell-cycle phosphatase as a target of c-myc. Nature 382: 511–517.

Roy, A. L., Carruthers, C., Gutjahr, T., and Roeder, R. G. (1993). Direct role for Myc in transcription initiation mediated by interactions with TFII-I. Nature 365: 359–361.

Li, L.-h., Nerlov, C., Prendergast, G., MacGregor, D., and Ziff, E. B. (1994). c-Myc represses transcription in vivo by a novel mechanism dependent on the initiator element and Myc box II. The EMBO J. 13: 4070–4079.

Mai, S. and Martensoon, I.-L. (1995). The c-myc protein represses λ5 and TdT initiators. Nucl. Ac. Res. 23: 1–9.

Heikkila, R., Schwab, G., Wickstrom, E., Loke, S. L., Pluznik, D. H., Watt, R., and Neckers, L. M. (1987). A c-myc antisense oligodeoxynucleotide inhibits entry into S phase but not progress from Go to G1. Nature 328: 445–449.

Karn, J., Watson, J. V., Lowe, A. D., Green, S. M., and Vedeckis, W. (1989). Regulation of cell cycle duration by c-myc levels. Oncogene 4: 773–787.

Hanson, K. D., Schichiri, M., Follansbee, J. R., and Sedivy, J. M. (1994). Effects of c-myc expression on cell cycle progression. Mol. Cell. Biol. 14: 5748–5755.

Stanton, L. W., Watt, R., Marcu, K. B. (1983). Translocation, breakage, and truncated transcripts of c-myc oncogene in murine plasmacytomas. Nature 303: 401–406.

Potter, M. and Wienr, F. (1992). Plasmacytomagenesis in mice: model of neoplastic development dependent upon chromosomal translocation. Carcinogenesis 13: 1681–1697.

Feo, S., Liegro, C. D., Jones, T., Read, M., and Fried, M. (1994). The DNA region around the c-myc gene and its amplification in human tumour cell lines. Oncogene 9: 955–961.

Alito, K. (1985). Amplification of cellular oncogenes in cancer cells. TIBS 10: 194–197.

Classon, M., Henriksson, M., Klein, G., and Hammaskjold, M.-L. (1987). Elevated c-myc expression facilitates the replication of SV40 in human lymphoid cells. Nature 330: 272–274.

Classon, M., Henriksson, M., Klein, G. and Hammerskjold, M.-L. (1990). The effect of c-myc protein on SV40 replication in human lymphoid cells. Oncogene 5: 1371–1376.

Classon, M., Wennborg, M., Klein, G., and Sümegi, J. (1993). Analysis of c-Myc domains involved in stimulating SV40 replication. Gene 133: 153–161.

Luecke-Huhle, C., Mai, S., Herrlich, P. (1989). UV-inducible early-domain binding factor as the limiting component of Simian Virus 40 DNA amplification in rodent cells. Mol. Cell. Biol. 9: 4812–4818.

Mai, S., Lücke-Huhle, C., Kaina, B., Rahmsdorf, H. J., Stein, B., Ponta, H., and Herrlich, P. (1990):Ionizing radiation induced formation of a replication origin binding complex involving the product of the cellular oncogene c-Myc. In: Ionizing Radiation Damage of DNA. Molecular Aspects. Wiley-Liss., New York, N.Y., 319–331.

Mai, S. and Jalava, A. (1994). c-Myc binds to 5' flanking sequence motifs of the dihydrofolate reductase gene in cellular extracts: role in proliferation. Nucl. Acids Res. 22: 2264–2273.

Wells, J., Held, P., Illenye, S., and Heintz, N. H. (1996). Protein-DNA interactions at the major and minor promoters of the divergently transcribed dhfr and rep 3 genes during the Chinese hamster ovary cell cycle. Mol. Cell. Biol. 16: 634–647.

Luecke-Huhle, C., Mai, S., Moll, J. (1996). Correlation of gene expression and gene amplification. Proc. of the ICRR pp. 560–564.

Kunz, B. A., Kohalmi, S. E., Kunkel, T. A., Mathews, C. K., Mcintosh, E. M., Reidy, J. A. (1994). Deoxyribonucleoside triphosophate levels: a critical factor in the maintenance of genetic stability. Mut. Res. 318: 1–64.

Luecke-Huhle, C. (1994). Permissivity for methotrexate-induced DHFR gene amplification correlates with the metastic potential of rat adenocarcinoma cells. Carcinogenesis 15: 695–700.

Mai, S. and Jalava, A. 1994. c-Myc binds to 5' flanking sequence motifs of the dihydrofolate reductase gene in cellular extracts: role in proliferation. *Nucl. Acids Res*. 22: 2264–2273.

Denis, J., Kitzis, A., Kruh, J., Dautry, F., and Crocos, D. 1991. Stimulation of methotrexate resistance and dihydrofolate reductase gene amplification by c-myc. *Oncogene* 6:1453–1457.

Wells, J., Held, P., Illenye, S., and Heintz, N. H. 1996. Protein-DNA interactions at the major and minor promoters of the divergently transcribed dhfr and rep 3 genes during the Chinese hamster ovary cell cycle. Mol. Cell. Biol 16: 634–647.

Mai, S. 1994. Overexpression of c-myc precedes amplification of the gene encoding dihydrofolate reductase. *Gene* 148: 253–260.

Mai, S., Hanley-Hyde, J., Fluri, M. 1996. c-Myc overexpression associated DHFR gene amplification in hamster, rat, mouse and human cell lines. *Oncogene* 12: 277–288.

Luecke-Huhle, C., Mai, S., Moll, J. 1996. Correlation of gene expression and gene amplification. *Proc. of the ICRR*. pp. 560–564.

Mai, s., Fluri, M., Siwarski, D., Huppi, K. 1996. Genomic instability in MycER activated Rat1A-MycER cells. *Chromosome Research* 4: 1–7.

Fukasawa, K., Wiener, F., Vande Woude, G. f., Mai, S. 1997. Genomic instability and apoptosis are frequent in p53 deficient young mic. *Oncogene* 15: 1295–1302.

Potter and Wiener, 1992. Plasmacytomagenesis in mice: model of neoplastic development dependent upon chromosomal translocation. *Carcinogenesis* 13: 1681–1697.

Mock, B., Krall, M. M., and Dosik, J. K. 1993. Genetic mapping of tumor susceptibility genes in mouse plasmacytomagenesis. *Proc. Natl. Acad. Sci. (USA)* 90: 9499–9503.

Potter, M. Mushinski, E. B., Wax, J. S., Hartley, J., and Mock, B. A. 1994. Identification of two genes on chromosome 4 that determine resistance to plasmacytoma induction in mice. *Cancer Research* 54: 969–975.

Silva, S., Wang, Y., Babonits, M., Imreh, S., Wiener, F., Klein, G. 1997. Spontaneous development of plasmacytomas in a selected subline of Balbc/cJ mice. *Eur. J. Cancer* 33: 479–485.

Evan, G. I., Lewis, G. K., Ramsay, G., Bishop, J. M. 1985. Isolation of monoclanal antibodies specific for human c-myc proto-oncogene product. *Mol Cell. Biol.* 5: 3610–3616.

Chang, A. C., Nunberg, J. H., Kaufman, R. J., Erlich, H. A., Schimke, R. T., Cohen, S. N. 1978. Phenotypic expression in *E. coli* of a DNA sequence coding for mouse dihydrofolate reductase. *Nature* 275: 617–624.

Eckschlager, T. and McClain, K. 1996. Comparison of fluorescent in situ hybridization (FISH) and the polymerase chain reaction (PCR) for detection of residual neuroblastoma cells. *Neoplasma* 43: 301–303.

White, D. L, Hutchins, C. J., Turczynowicz, S., Suttle, J., Haylock, D. N., Hughes, T. P., Juttner, C. A., To, L. B. 1997. Detection of minimal residual disease in an aml patient with trisomy 8 using interphase FISH. *Pathology* 29: 289–293.

Afify, A. and Mark, H. F. 1997. Fluorescence in situ hybridization assessment of chromosome 8 copy number in stage I and stage II infiltrating ductal carcinoma of the breast. Cancer Genet. *Cytogenet* 97: 101–105.

Kunz, J. A. 1994. Deoxyribonucleoside triphosphate levels: a critical factor in the maintenance of genetic stability. *Mut. Res*. 318: 1–64.

Luecke-Huhle, C. 1994. Permissivity for methotrexate-induced DHFR gene amplification correlates with the metastic potential of rat adenocarcinoma cells. *Carcinogenesis* 15: 695–700.

Burke and Olson, "Preparation of Clone Libraries in Yeast Artificial-Chromosome Vectors" in *Methods in Enzymology*, Vol. 194, "Guide to Yeast Genetics and Molecular Biology", eds. C. Guthrie and G. Fink, Academic Press, Inc., Chap. 17, pp. 251–270 (1991).

Capecchi, "Altering the genome by homologous recombination" *Science* 244:1288–1292 (1989).

Davies et al., "Targeted alterations in yeast artificial chromosomes for inter-species gene transfer", *Nucleic Acids Research*, Vol. 20, No. 11, pp. 2693–2698 (1992).

Dickinson et al., "High frequency gene targeting using insertional vectors", *Human Molecular Genetics*, Vol. 2, No. 8, pp. 1299–1302 (1993).

Duff and Lincoln, "Insertion of a pathogenic mutation into a yeast artificial chromosome containing the human APP gene and expression in ES cells", *Research Advances in Alzheimer's Disease and Related Disorders*, 1995.

Huxley et al., "The human HPRT gene on a yeast artificial chromosome is functional when transferred to mouse cells by cell fusion", *Genomics*, 9:742–750 (1991).

Jakobovits et al., "Germ-line transmission and expression of a human-derived yeast artificial chromosome", *Nature*, Vol. 362, pp. 255–261 (1993).

Lamb et al., "Introduction and expression of the 400 kilobase precursor amyloid protein gene in transgenic mice", *Nature Genetics*, Vol. 5, pp. 22–29 (1993).

Pearson and Choi, *Expression of the human $-amyloid precursor protein gene from a heast artificial chromosome in transgenic mice*. Proc. Natl. Scad. Sci. USA, 1993. 90:10578–82.

Rothstein, "Targeting, disruption, replacement, and allele rescue: integrative DNA transformation in yeast" in *Methods in Enzymology*, Vol. 194, "Guide to Yeast Genetics and Molecular Biology", eds. C. Guthrie and G. Fink, Academic Press, Inc., Chap. 19, pp. 281–301 (1991).

Schedl et al., "A yeast artificial chromosome covering the tyrosinase gene confers copy number-dependent expression in transgenic mice", *Nature*, Vol. 362, pp. 258–261 (1993).

Strauss et al., "Germ line transmission of a yeast artificial chromosome spanning the murine"$_1$ (I) collagen locus", *Science*, Vol. 259, pp. 1904–1907 (1993).

Gilboa, E, Eglitis, M A, Kantoff, P W, Anderson, W F: Transfer and expression of cloned genes using retroviral vectors. BioTechniques 4(6):504–512, 1986.

Cregg J M, Vedvick T S, Raschke W C: Recent Advances in the Expression of Foreign Genes in *Pichia pastoris*, Bio/Technology 11:905–910, 1993

Culver, 1998. Site-Directed recombination for repair of mutations in the human ADA gene. (Abstract) Antisense DNA & RNA based therapeutics, February, 1998, Coronado, Calif.

Agrawal, 1996. Antisense oligonucleotides: towards clinical trials, TIBTECH, 14:376.

Akhter et al, 1991. Interactions of antisense DNA oligonucleotide analogs with phospholipid membranes (liposomes). Nuc. Res. 19:5551–5559.

Blaesse, 1997. Gene Therapy for Cancer. Scientific American 276(6):111–115.

Calabretta, et al, 1996. Antisense strategies in the treatment of leukemias. Semin. Oncol. 23:78.

Crooke, 1995. Progress in antisense therapeutics, Hematol. Pathol. 2:59.

Felgner, 1997. Nonviral Strategeies for Gene Therapy. Scinetific American. June, 1997, pgs 102–106.

Gewirtz, 1993. Oligodeoxynucleotide-based therapeutics for human leukemias, Stem Cells Dayt. 11:96.

Hanania, et al 1995. Recent advances in the application of gene therapy to human disease. Am. J. Med. 99:537.

Lefebvre-d'Hellencourt et al, 1995. Immunomodulation by cytokine antisense oligonucleotides. Eur. Cytokine Netw. 6:7.

Lev-Lehman et al., 1997. Antisense Oligomers in vitro and in vivo. In *Antisense Therapeutics*, A. Cohen and S. Smicek, eds (Plenum Press, New York)

Loke et al, 1989. Characterization of oligonucleotide transport into living cells. PNAS USA 86:3474.

Morrison, 1991. Suppression of basic fibroblast growth factor expression by antisense oligonucleotides inhibits the growth of transformed human astrocytes. J. Biol. Chem. 266:728.

Rosolen et al., 1990. Cancer Res. 50:6316.

Uhlmann and Peyman, 1990. Antisense Oligonucleotides: A New Therapeutic Principle. Chem Rev 90(4):543–584.

Wagner et al., 1996. Potent and selective inhibition of gene expression by an antisense heptanucleotide. Nature Biotechnology 14 :840–844.

Wagner, 1994. Gene inhibition using antisense oligodeoxynucleotides. Nature 372:333.

Whitesell et al., 1991. Episome-generated N-myc antisense RNA restricts the differentiation potential of primitive neuroectodermal cell lines. Mol. Cell. Biol. 11:1360.

Yakubov et al, 1989. PNAS USA 86:6454.

Wright & Anazodo, 1995. Antisense Molecules and Their Potential For The Treatment Of Cancer and AIDS. Cancer J. 8:185–189.

Scanlon et al., 1995. Oligonucleotides-mediated modulation of mammalian gene expression. FASEB J. 9:1288.

Galileo et al., 1991. J. Cell. Biol., 112:1285. Gewirtz, 1993. Oligodeoxynucleotide-based therapeutics for human leukemias, Stem Cells Dayt. 11:96.

Eckstein 1985. Nucleoside Phosphorothioates. Ann. Rev. Biochem. 54:367–402. Iyer et al. 1990. J. Org. Chem. 55:4693–4699.

Radhakrishnan et al., 1990. The automated synthesis of sulfur-containing oligodeoxyribonucleotides using 3H-1, 2-Benzodithiol-3-One 1,1 Dioxide as a sulfur-transfer reagent. J. Org. Chem. 55:4693–4699.

Shaw et al., 1991. Modified deoxyoligonucleotides stable to exonuclease degradation in serum. Nucleic Acids Res. 19:747–750.

Spitzer and Eckstein 1988. Inhibition of deoxynucleases by phosphorothioate groups in oligodeoxyribonucleotides. Nucleic Acids Res. 18:11691–11704.

Woolf et al., 1990. The stability, toxicity and effectiveness of unmodified and phosphorothioate antisense oligodeoxynucleotides in *Xenopus oocytes* and embryos. Nucleic Acids Res. 18:1763–1769.

Blackwood E M and Eisenman R T. (1991). Science 251, 1211–1216.

Brooks A R, Shiffman D, Chan C S, Brooks E E and Milner P G. (1996). J. Biol. Chem. 271, 9090–9099.

Citri Y, Braun J and Baltimore D. (1987). J. Exp. Med. 165, 1188–1194.

Cohen S, Regev A and Lavi S. (1997). Oncogene 14 977–985. Cole M D. (1986). Ann Rev. Genet. 20, 361–384.

Coleman A E, Schröck E, Weaver Z, du Manoir S, Yang F, Ferguson-Smith M A, Ried T and Janz S. (1997). Can. Res. 57, 4585–4592.

Daksis J I, Lu R Y, Facchini L M, Marhin W W and Penn L J Z. (1994). Oncogene 9, 3635–3645.

Erisman, M D, Scott J K, Watt R A and Astrin S M. (1988). Oncogene 2, 367–378.

Fan H, Villegas C and Wright J A. (1996). Proc. Natl. Acad. Sci. USA 93, 14036–14040.

Feo S. Liegro C D, Jones T, Read M and Fried M. (1994). Oncogene 9, 955–961.

Fort P, Marty L, Piechaczyk M, E I Sabrouty S, Dani C, Jeanteur P and Blanchard J M. (1985). Nucl. Acids Res. 13, 1431–1437.

Galaktionov K., Chen X and Beach D. (1996). Nature 382, 511–517.

Gurfinkel N, Unger T, Givol D and Mushinski J F. (1987). Eur. J. Immunol. 17, 567–570.

Hamel P A and Hanley-Hyde J. (1997). Cancer Investigation 15, 143–152.

Hanna Z, Jankowski M, Tremblay P, Jiang X, Milatovich A, Francke U and Jolicoeur P. (1993). Oncogene 8, 1661–1666.

Hanson K D, Shichiri M, Follansbee M R and Sedivy J M. (1994). Mol. Cell Biol. 14, 5748–5755.

Hayward W S, Neel B G and Astrin S M. (1981). Nature 290, 475–480.

Heikkila R, Schwab G, Wickstrom E, Loke S L, Pluznik D H, Watt R and Neckers L M (1987). Nature 328, 445–449.

Jaffe B M, Eisen H N, Simms E S and Potter M. (1969). J. Immunol. 103, 872–878.

Jansen-Deurr P, Meichle A, Steiner P, Pagano M, Finke K, Botz J, Wessbecher J, Draetta G and Eilers M. (1993). Proc. Natl. Acad. Sci. USA 90, 3685–3689

Jiang W, Kahn S M, Zhou P, Zhang Y J, Cacace A M, Infante S D, Santella R M and Weinstein I B. (1993). Oncogene 8, 3447–3457.

Jun D Y, Kim M K, Kim I G and Kim Y H. 1997. Mol. Cells 7, 537–543.

Karn J, Watson J V, Lowe A D, Green S M and Vedeckis W. (1989). Oncogene 4, 773–787.

Kiyokawa H, Busquets X, Powell C T, Ngo L, Rifkind R A and Marks P A. (1992). Proc. Natl. Acad. Sci. USA 89, 2444–2447.

Leach F S, Elledge S J, Sherr C J, Willson J K V, Markowitz S, Kinzler K W and Vogelstein B (1993). Cancer Res. 53,1986–1989.

Littlewood T D, Hancock D C, Danielian P S, Parker M G and Evan G I. (1995). Nucl. Acids Res. 23,1686–1690.

Luecke-Huhle C. (1994). Carcinogenesis 15, 695–700.

Mai S. (1994). Gene 148, 253–260.

Mai S, Hanley-Hyde J, Coleman A, Siwarski D and Huppi K. (1995). Genome 38, 780–785.

Mai S. Hanley-Hyde J. and Fluri M. 1996. Oncogene 12, 277–288.

Mai S and Jalava A. (1994). Nucl. Acids Res. 22, 2264–2273.

Mann R, Mulligan R C and Baltimore D. (1983). Cell 33, 153–159.

Marcu K B, Bossone S A and Patel A J. (1992). Ann. Rev. Biochem. 61, 809–860.

Matsushime H, Roussel M F, Ashmun R A and Sherr C J. (1991). Cell 65, 701–713.

Mischak H, Goodnight J, Kolch W, Martiny-Baron G, Schaechtle C, Kazanietz, M G, Blumberg P M, Pierce J H and Mushinski J F. (1993). J. Biol. Chem. 268, 6090–6096.

Morse B, Rotherg P G, South V J, Spandorfer J M and Astrin S M. (1993). Nature 333, 87–90.

Motokura T and Arnold A. Curr. Opin. Genet. Dev. 3, 5–10.

Mushinski J F. (1988). In Cellular Oncogene Activation (ed. Klein) pp. 181–211. Marcel Dekker, New York and Basel.

Mushinski J F, Davidson W D and Morse H C. (1987). Cancer Invest. 5, 345–368.

Pear W S, Wahlstrom G, Nelson S F, Axelson H, Szeles A, Wiener F, Bazin H, Klein G and Sumegi J. (1988). Mol. Cell Biol. 8, 441–451.

Philipp A, Schneider A, Vaestrik I, Finke K, Xiong Y, Beach D, Alitalo K and Eilers M. (1994). Mol. Cell Biol. 14, 4032–4043.

Press M F, Bernstein L, Thomas P A, Meisner L F, Zhou J-Y, Ma Y, Hung G, Robinson R A, Harris C. El-Naggar A, Slamon D J, Phillips R N, Ross J S, Wolman S R and Flom K J. (1997). J. Clin. Oncol. 15, 2894–2904.

Rosenberg N, and Baltimore D. (1976). J. Exp. Med. 143, 1453–1463.

Sambrook J, Fritsch E F and Maniatis T. (1989). A laboratory manual. Cold Spring Harbor.

Shen-Ong G L C, Keath E J, Piccoli S P and Cole M D. (1982). Cell 31, 443–480.

Sinclair A J, Palmero I, Peters G and Farrell P J. (1994). EMBO J 13, 3321–3328.

Southern E M. (1975). J. Biol. Chem. 253, 5852–5860.

Stanton, L W, Watt R and Marcu K B. (1983). Nature 303, 401–406.

Steiner P, Philipp A, Lukas J, Godden-Kent D, Pagano M, Mittnacht S, Bartek J and Eilers M. (1995). EMBO J 14, 4814–4826.

Taub R, Kirsch I, Morton C, Lenoir G M, Swan D, Tronick S, Aaronson S and Leder P. (1982). Proc. Natl. Acad. Sci. USA 79, 7837–7841.

Thelander L and Berg P. (1986). Mol. Cell Biol. 6, 3433–3442.

Wang T C, Cardiff Rd, Zuckerberg L, Lees E, Arnold A and Schmidt E V. (1994). Nature 369, 669–671.

Waters C M, Littlewood T D, Hancock D C, Moore J P and Evan G I. (1991). Oncogene 6, 797–805.

Yokota Y, Tsunetsugu-Yokota Y, Battifora C L and Cline M J. (1986). Science 231, 261–265.

Zhang S-Y, Liu S-C, Goodrow T, Morris R and Klein-Szanto A J P. (1997). Mol. Carcinogenesis 18, 142–152.

Zhou P, Jiang W Zhang Y, Kahn S M, Schieren I, Santella R M and Weinstein I B. (1995). Oncogene 11, 571–580.

Aoyama, C., Peters, J., Senadheera, S., Liu, P. and Shimada, H. Uterine cervical dysplasia and cancer: identification of c-myc status by quantitative polymerase chain reaction. Diagn Mol Pathol 7:324–330, 1998.

Atkin, N. B., Barker, M. C., Fox, M. F. Chromosome changes in 43 carcinomas of the cervix uteri. Cancer Genet Cytogenet 44: 229–241. 1990.

Auer, R. L., Bienz, N., Neilson, J., Cai, M., Waters, J. J., Milligan, D. W. and Fegan, C. D. The sequential analysis of trisomy 12 in B-cell chronic lymphocytic leukaemia. Br J Haematol 194: 742–744. 1999.

Baker, V. V., Hatch, K. D. and Shingleton, H. M. Amplification of the c-myc proto-oncogene in cervical carcinoma. J Surg Oncol 39: 225–228. 1988.

Boon, M. E., Kleinschmidt-Guy, E. D., Ouwerkerk-Noordam, E. PAPNET for analysis of proliferating (MIB-1 positive) cell populations of cervical smears. Eur J Morphol 32: 78–85. 1994.

Boon, M. E. Kleinschmidt-Guy, E. D., Wijsman-Grootendorst, A. and Hoogeveen, M. M. Upgrading unsatisfactory cervical smears with the MiB-1 method. Diagn Cytopathol 15: 270–276. 1996.

Bourhis, J., Le, M. G., Barrois, M., Gerbaulet, A., Jeannel, D., Duvillard, P., Le Doussal, V., Chassagne, D and Riou, G. Prognostic value of c-myc proto-oncogene overexpression in early invasive carcinoma of the cervix. J. Clin Oncol 8: 1788–1796. 1990.

Bulten, J., van der Laak, J. A., Gemmink, J. H. Pahlplatz, M. M., de Wilde, P. C. and Hanselaar, A. G. MIB1, a promising marker for the classification of cervical intraepithelial neoplasia. J. Pathol 178: 268–273. 1996.

Carder, P. J., al-Naufssi, A., Rahilly, M., Lauder, J. and Harrison, D. J. Glutathione S-transferase detoxication enzymes in cervical neoplasia. J Pathol 162: 303–308. 1990.

Cheung, T. H., Chung, T. K., Poon, C. S., Hampton, G. M., Wang, V. W. and Wong, Y. F. Allelic loss on chromosome 1 is associated with tumor progression of cervicalcarcinoma. Cancer 86: 1294–1298. 1999.

Choo, K. B., Chong, K. Y., Chou, H. F., Liew, L. N., and Liou, C. C. Analysis of the structure and expression of c-myc oncogene in cervical tumor and in cervical tumor-derived cell lines. Biochem Biophys Res Commun 158: 334–340. 1989.

Comerci, J. T. Jr., Runowicz, C. D., Flanders, K. C., De Victoria, C., Fields, A. L., Kadish, A. S. and Goldberg, G. L. Altered expression of transforming growth factor-beta 1 in cervical neoplasia as an early biomarker in carcinogenesis of the uterine cervix. Cancer 77: 1107–1114. 1996.

Couturier, J., Sastre-Garau, X., Schneider-Maunoury, S., Labib, A. and Orth, G. Integration ofk papillomavirus DNA near myc genes in genital carcinomas and its consequence for protooncogene expression. J Virol 65: 4534–4538. 1991.

Crawford, R. W., Caldwell, C., lies, R. K., Lowe, D., Shepherd, J. H. and Chard, T. Prognostic significance of the bel-2 apoptotic family of proteins in primary and recurrent cervical cancer. Br J Cancer 78: 210–214. 1998.

Dellas, A., Schultheiss, E., Holzgreve, W., Oberholzer, M., Torhorst, J. and Gudat, F Investigation of the bel2 and c-myc expression in relationship to the Ki-67 labelling index in cervical intraepithelial neoplasia. Int J Gynecol Pathol 16: 212–218. 1997.

Dellas, A., Schultheiss, E., Leivas, M. R., Moch, H. and Torhorst, J. Association of p27Kip1, cyclin E and c-myc expression with progression and prognosis in HPV-positive cervical neoplasma. Anticancer Res 18: 3991–3998. 1998.

Dellas A., Torhorst, J., Jiang, F., Profitt, J., Schultheiss, E., Holzgreve, W., Sauter, G., Mihatsch, M. J. and Moch, H. Prognostic value of genomic alterations in invasive cervical carcinoma of clinical stage IB detected by comparative genomic hybridization. Cancer Re. 59: 3475–3479. 1999.

Dohner, H., Stilgenbauer, S., Dohner, K., Bentz, M. and Lichter, P. Chromosome aberrations in B-cell chronic lymphocytic leukemia: reassessment on molecular cytogenetic analysis. J Mol Med 77: 266–281. 1999.

Felsher, D. W. and Bishop, J. M. Transient excess of MYC activity can elicit genomic instability and tumorigenesis. Proc Natl Acad Sci (USA) 96: 3940–3944. 1999.

Freeman, A., Morris, L. S., Mills, A. D., Stoeber, K., Laskey, R. A., Williams, G. H. and Coleman, N. Minichromosome maintenance proteins as biological markers of dysplasia and malignancy. Clin Cancer Res 5: 2121–2132. 1999.

Gibbons, D., Fogt, F., Kasznica, J., Holden J. and Nikulasson, S. Comparison of topoisomerase II alpha and MIB-1 expression in uterine cervical squamous lesions. Med Pathol 10: 409–413. 1997.

Gotoh, M., Nakajima, T., Yokota, J., Tsunokawa, Y., Terada, M., Shimoyama, Y., Teshima, S., Hirohashi, S. and Shimosato, Y. Newly estasblished uterine cervical carcinoma cell line with co-amplification of human papillomavirus DNA and c-myc gene. Jpn. J. Cancer Res. 82: 1252–1257. 1991.

Hampton, G. M., Penny, L. A. Baergen, R. N., Larson, A., Brewer, C., Liao, S., Busby-Earle, R. M., Williams, A. W., Steel, C. M., Bird, C. C. et al. Loss of heterozygosity in cervical carcinoma: subchromosomal localization of a putative tumor-suppressor gene to chromosome 11q22-q24. Proc Natl Acad. Sci 9 USA) 91: 6953–6957. 1994.

Helm, C. W., Shrestha, K., Thomas, S., Shingleton, H. M. and Miller, D. M. A unique c-myc-targeted triplex-forming oligonucleotide inhibits the growth of ovarian and cervical carcinomas in vitro. Gynecol Oncol 49: 339–343. 1993.

Heselmeyer, K., Macville, M., Schrock, E., Blegen, H., Hellstrom, A. C., Shah, K., Auer, G. and Ried, T. Advanced-stage cervical carcinomas are defined by a recurrent pattern of chromosomal aberrations revealing high genetic instability and a consistent gain of chromosome arm 3q. Genes Chromosomes Cancer 19: 233–240. 1997.

Hesselmeyer, K., Schrock, E., du Manoir, S., Blegen, H., Shah, K., Steinbeck, R., Auer, G and Ried, T. Gain of chromosome 3q defines the transition from severe dysplasia to invasive carcinoma of the uterine cervix. Proc. Natl. Acad. Sci (USA) 93: 479–484. 1996.

Hu, W., Mitchell, M. F., Boiko, I. V., Linares, A., Kim, H. G., Malpica, A., Tortolero-Luna, G. and Hittelman, W. N. Progressive dysregulation of proliferation during cervical carcinogenesis as measured by MPM-2 antibody staining. Cancer Epidemiol Biomarkers Prev 6: 711–718. 1997.

Iwasaka, T., Yokoyama, M., Oh-uchida, M., Matsuo, N., Hara, K., Fukuyama, K., Hachisuga, T., Fukada, K. and Sugimori, H. Detection of human papillomavirus genome and analysis of expression of c-myc and Ha-ras oncogenes in invasive cervical carcinomas. Gynecol Oncol. 46: 298–303. 1992.

Kanai, M., Shiozawa, T., Xin, L., Nikaido, T. and Fujii, S. Immunohistochemical detection of sex steroid receptors, cyclins, and cyclin-dependent kinases in normal and neoplastic squamous epithelia of the uterine cervix. Cancer 82: 1709–1719. 1998.

Kang, S. H., Won, K., Chung, H. W., Jong, H. S., Song, Y. S., Kim, S. J., Bang, Y. J. and Kim, N. K. Genetic integrity of transforming growth factor beta (TGF-beta) receptors in cervical carcinoma cell liones: loss of growth sensitivity but conserved transcriptional response to TGF-beta. Int. J. Cancer 77: 620–625. 1998.

Kersemackers, A. M., Fleuren, G. J., Kenter, G., G., Van den Broek, L. J., Uljee, S. M., Hermans, J. and Van de Vijver, M. J. Oncogene alterations in carcinomas of the uterine cervix: overexpression of the epidermal growth factor receptor is associated with poor prognosis. Clin Cancer Res 5: 577–586. 1999.

Kim, Y. T., Cho, N. H., Park, S. W. and Kim, J. W. Underexpression of cyclin-dependent kinase (CDK) inhibitors in cervical carcinoma. Gynecol Oncol 71: 38–45. 1998.

Kisseljob, F., Semionova, L., Samoylova, E., Mazurenko, N., Komissarova, E., Zourbitskaya, V., Gritzko, T., Kozachenko, V., Netchushkin, M., Petrov. S., Smirnov, A., and Alonso, A. Instability of chromosome 6 microsatellite repeats in human cervical tumors carrying papillomavirus sequences. In J Cancer 69: 484–487. 1996.

Kleter, B., van Doorn, L. J., ter Schegget, J., Schrauwen, L., Van Krimpen, K., Burger, M., ter Harmsel, B. and quint, W. Novel short-fragment PCR assay for highly sensitive broad spectrum detection of anogenital human papillomaviruses. Am J. Pathol 153: 1731–1739. 1998.

Kuschak, T. I., Taylor, C., McMillan-Ward, E., Israels, S., Henderson, D. W., Mushinski, J. F., Wright, J. A. and Mai, S. The ribonucleotide reductase R2 gene is non-transcribed target of c-Myc-induced genomic instability. Gene. 238: 351–365. 1999.

Larson, A. A., Kern, S., Curtiss, S., Gordon, R., Cavenee, W. K. and Hampton, G. M. High resolution analysis of chromosome 3p alterations in cervical carcinoma. Cancer Res 57: 4082–4090. 1997.

Liao, S. Y. and Stanbridge, E. J. Expression of the MN antigen in cervical papanicolaou smears is an early diagnostic biomerker of cervical dysplasia. Cancer Epidemiolo Biomarkers Prev 5: 49–557. 1996.

Liso, V., Capalbo, S., Lapietra, A., Pavone, V., Guarini, A. and Specchia, G. Evaluation of trisomy 12 by fluorescence in situ hybridization in peripheral blood, bone marrow and lymph nodes of patients with B-cell chronic lymphocytic leukemia. Haematologica 84: 212–217. 1999.

Macville, M., Schrock, E., Padilla-Nash, H., Heck, C., Ghadimi, B. M., Zimonjic, D., Popescu, N. and Ried, T. Comparative and definitive molecular cytogenetic characterization of HeLa cells by spectral karyotyping. Cancer Res. 59: 141–150. 1999.

Mai, S., Hanley-Hyde, J., Rainey, G. J. Kuschak, T. I., Paul, J. T., Littlewood, T. D., Mischak, H., Stevens, L. M., Henderson, D. W., Mushinski, J. F. Chromosomal and extrachromosomal instability of the cyclin D2 gene is induced by Myc overexpression. Neoplasia 1: 241–252. 1999.

Mark, H. F., Feldman, D., Samy, M., sun, C., Das, S., Mark, S. and Lathrop, J. Assessment of chromosome 8 copy number in cervical cancer by fluorescent in situ hybridization. Exp Mol Pathol 66: 157–162. 1999.

Mazurenko, N., Attaleb, M., Gritsko, T., Semjonova, L., Pavlova, L., Sakharova, O. and Kisseljov, F. High resolution mapping of chromosome 6 deletions in cervical cancer. Oncol Rep 6: 859–863. 1999.

Milde-Langosch, K., Becker, G. and Loning, T. Human papillomavirus and c-myc/c-erB2 in uterine and vulvar lesions. Virchows Arch Pathol Anat Histopathol 419: 479–485. 1991.

Mitra, A. B., Murly, V. V., Li, R. G., Protop, M., Luthra, U. K., Chaganti, R. S. Alelotype analysis of cervical carcinoma. Cancer Res. 54: 4481–4487. 1994.

Mitra, A. B., Murty, V. V., Singh, V., Li, R. G., Pratap, M., Sodhani, P., Luthra, U. K. and Chaganti, R. S. Genetic alterations at 5p15: a potential marker for progression of precancerous lesions of the uterine cervix. J Natl Cancer Inst 87: 742–745. 1995.

Mitra, A. B. Genetic deletion and human papillomavirus infection in cervical cancer: loss of heterozygosity sites at 3p and 5p are important genetic events. Int. J. Cancer 82: 322–323. 1999.

Mittal, K. Utility of proliferation-associated marker MIB-1 in evaluating lesions of the uterine cervix. Adv Anat Pathol 6: 177–185. 1999.

Mittal, K., Mesia, A. and Demopoulos, R. I. MIB-1 expression is useful in distinguishing dysplasia from atrophy in elderly women. Int J Gynecol Pathol 18: 122–124. 1999.

Mullakondov, M. R., Kholodilov, N. G., Atkin, N. B., Burk, R. D., Johnson, A. B. and Klinger, H. P. Genomic alterations in cervical carcinomas: losses of chromosome heterozygosity and human paiplloma virus status. Cancer Res 56: 197–205. 1999.

Munzel, P., Marx, D., Kochel, H., Schauer, A., Bock, K. W. Genomic alterations of the c-myc protooncogene in relation to the overexpression of c-erbB2 and Ki-67 in human breast and cervix carcinoma. J. Cancer Res Clin Oncol 117: 603–607. 1991.

Ocadiz, R., Sauceda, R., Cruz, M., Graef, A. M. and Gariglio, P. High correlation between molecular alterations of the c-myc oncogene and carcinoma in the uterine cervix. Cancer Res 47: 4173–4177. 1987.

Ocadiz, R., Sauceda, R., Salcedo, M., Ortega, V., Rodriguez, H., Gordillo, C., Chavez, P. and Gariglio, P. Occurrence of human papillomavirus type 16 DNA sequences and c-myc oncogene alterations in uterine-cervix carcinoma. Arch Invest Med (MEX) 20: 355–362. 1989.

Pinto, A. P:., Lin, M. C., Mutter, G. L., Sun, D., Villa, L. L. and Crum, C. P. Allelic loss in human papillomavirus-positive and negative vulvar squamous cell carcinomas. Am J. Pathol 154: 1009–1015. 1999.

Popescu, N. C. and DiPaolo, J. A. Preferential sites for viral integration on mammalian genom. Cancer Genet Cytogenet 42: 157–171. 1989.

Rader, J. S., Gerhard, D. S., O'Sullivan, M. J., Li, Y., Liapis, H. and Huettner, P. C. Cervical intraepithelial neoplasia III shows frequent allelic loss in 3p and 6p. Genes Chromosomes Cancer 22: 57–65. 1998.

Risinger, J. I., Uman, A., Boyer, J. C., Evans, A. C., Berchuk, A., Kunkel, T. A. and Barrett, J. C. Microsatellite instability in gynecological sarcomas and in hMSH2 mutant uterine sarcoma cell lines defective in mismatch repair activity. Cancer Res 55: 5664–5669. 1995.

Riou, G., Le, M. G., Favre, M., Jeannel, D., Bourhis, J. and Orth, G. Human papillomavirus-negative status and c-myc gene overexpression: independent prognostic indicators of distant metastatsis for early-stage invasive cervical cancers. J Natl Cancer Inst 84: 1525–1526. 1992.

Riou, G. F., Bourhis, J. and Le, M. G. The c-myc proto-oncogene in invasive carcinomas of the uterine cervix: clinical relevance of overexpression in early stages of the cancer. Anticancer Res 10: 1225–1231. 1990.

Robertson, G. P. Hufford, A., Lugo, T. G. A panel of transferable fragments of human chromosome 11q. Cytogenet Cell Genet 79: 53–59. 1997.

Rodriguez, J. A., Barros, F., Carracedo, A. and Mugica-van Herckenrode, C. M. Low incidence of microsatellite instability in patients with cervical carcinomas. Diagn. Mol Pathol 7: 276–282. 1998.

Segers, P., Haesen, S., Castelain, P., Amy, J. J., De Sutter, P., Van Dam, P. and Kirsch-Volders, M. Study of numerical aberrations of chromosome 1 by fluorescent in situ hybridization and DNA content by densitometric analysis on (pre)-malignant cervical lesions. Histochem J 27: 24–34. 1995.

Sharma, A., Pratap, M., Sawhney, V. M. Khan, I. U., Bhambhani, S. and Mitra, A. B. Frequent amplification of C-erbB2 (HER-2/Neu) oncogene in cervical carcinoma as detected by non-fluorescent in situ hybridization technique on paraffin sections. Oncology 56: 83–87. 1999.

Slagle, B. L., Kaufman, R. H., Reeves, W. C. and Icenogle, J. P. Expression of ras, myc, and p53 proteins in cervical intraepithelial neoplasia. Cancer 83: 1401–1408. 1998.

Sowani, A., Ong. G., Dische, S., Quinn, C., White, J., Soutter, P., Wasman, J. and Sikora, K. c-myc oncogene expression and clinical outcome in carcinoma of the cervix. Mol Cell Probes 3 117–123. 1989.

Spruck, C. H., Won, K. A. and Reed, S. I. Deregulated cyclin E induces chromosome instability. Nature 401: 297–300. 1999.

Steinbeck, R. G., Heselmeyer, K. M., Moberger, H. B. and Auer, G. U. The relationship between proliferating cell nuclear antigen (PCNA), nuclear DNA content and mutant p53 during genesis of cervical carcinoma. Acta Oncol 34: 171–176. 1995.

Symonds, R. P., Habeshaw, T., Paul, J., Kerr, D. J., Darling, A., Burnett, R. A., Sotsiou, F., Linardopoulos, S. and Spandidos, D. A. No correlation between ras, c-0myc and c-jun proto-oncogene expression and prognosis in advanced carcinoma of cervix. Eur J Cancer 28: 1615–1617. 1992.

Thein, A. T., Han, X., Heyderman, E., Fox, M., Steele, S. J. and Parrington, J. M. Molecular cytogenetic analysis of five newly established cervical cancer lines using G banding and fluorescent in situ hybridization. Cancer Genet Cytogenet 91: 28–36. 1996.

Thein, A., Trkova, M., Fox, M. and Parrinton, J. The application of comparative genomic hybridization to previously karyotyped cervical cancer cells. Cancer Genet Crytogenet 116: 59–65. 2000.

Van Kessel, A. G., Stellink, F., Janssen, I. And Schaap, N>Trisomy 12 resulting from isochromosomes of both 12p and 12q in a case of B-CLL. Cancer Genet Cytogenet 108: 85–86. 1999.

Walboomers, J. M. M., Jacobs, M>V., Manos, M. M., Bosch, F. X., Kummer, J. A. Shah, K. V., Snijders, P. J. F., Peto, J., Meijer, C. J. L. M. and Munoz, N. Human papillomavirus is a necessary cause of invasive cervical cancer worldwide. J Pathol 189: 12–19 1999.

Williams, G. H., Romanowski, P., Morris, L., Madine, M., Mills, A. D., Stoeber, K., Marr, J., Laskey, R. A. and Coleman, N. Improved cervical smear assessment using antibodies against proteins that regulate DNA replication. Proc. Natl Acad. Sci (USA) 95:14932–14937. 1999.

Wu, H. J. The expression of c-myc protein in uterine cervical cancer: a possible prognostic indicator. Nippon Sanka Fujinka Gakkai Zasshi 48: 515–521. 1996.

Yokota, J., Tsukada, Y., Nakijima, T., Gotoh, M., Shimosato, Y., Mori, N., Tsunokawa, Y., Sugimura, T. and Terada, M. Loss of heterozygosity on the shorm arm of chromosome 3 in carcinoma of the uterine cervix. Cancer Res. 49: 3598–35601. 1989.

Zhou, H., Zkuang, J., Zhong, L., Kuo, W. L., Gray, J. W., Sahin, A., Brinkley, B. R. and Sen, S. Tumor amplified kinase STK15.BTAK induces centrosome amplification, aneuploidy and transformation. Nat. genet. 20: 189–193. 1998.

Zur Hausen, H. Papillomavirus and p53. Nature 393: 217. 1998.

Zur Hausen, H. Paillomavirus infections—a major cause of human cancers. Bioch Biophys Acta 1288: F55–78. 1996.

Cory, S. (1986)*Adv. Cancer Res.* 47, 189–234.

Ohno, S., Babonits, M., Wiener, F., Spira, J., Klein, G. and Potter, M. (1979) *Cell* 18, 100 1–1007.

Potter, M. and Wiener, F. (1992) *Carcinogenesis* 13, 168 1–1697.

Shaughnessy, J. D., Jr, Owens, J. D., Wiener, F., Hubert, D. M., Huppi, K., Potter, M. and Mushinski, J. F. (1993) *Oncogene*8, 3111–3121.

Hayward, W., Neel, B. C., Astrin, S. (1981) *Nature* 290, 475–480.

Corcoran, L. M., Adams, J. M., Dunn, A R., Cory, S. (1984) *Cell* 37, 112–122.

Graham, M., Adams, J. M., Cory, S. (1985) *Nature* 314, 740–743.

Fahrlander, P. D., Sumegi, J., Yang, J., Wiener, F., Marcu, K. B., Klein, G. (1984) *Proc.Natl. Acad. Sci. (USA)* 81, 7046–7050.

Ohno, S., Migita, S., Murakami, S. (1989) *Oncogene* 4, 15 13–1517.

Ohno, S., Migita, S., Murakami, S. (1991) mt *J. Cancer* 49, 102–108.

1. MUller, J R, Janz S, Potter M. (1995) *Cancer Res* 55, 5012–5018.

Janz S, Kovaichuk A L, Muller J R, Potter M, (1997) *Curr Top Microbioll mmunol* 224, 24 1–250.

Shaughnessy J, Wiener F, Huppi K, Mushinski iF, Potter M. (1994) *Oncogene* 9, 247–253.

Merwin, R. M. and Redmon, I. W. (1963) *J. Nail. Cancer. Inst.* 31, 998–1007.

Wang, H. C. and Fedoroff, S. (1971)*Nature* 235, 52–54.

Committee on Standardized Genetic Nomenclature for Mice. New rules for nomenclatures of genes, chromosome anomalies and inbred strains. (1969) *Mouse News Letter* 17, 48 1–187.

Mai, S., Hanley-Hyde, J., Fluri, M. (1996) *Oncogene* 12, 277–288.

8. Fukasawa, K., Wiener, F., VandeWoude, G. F., Mai, S. (1997) *Oncogene* 15, 1295–1302.

Mai, S. (1994) *Gene* 148, 253–260.

Greenberg, R., Lang, R. B., Diamond, M. S., Marcu, K. B. (1982) *Nucleic Acids Res*. 10, 775 1–7761.

Huppi, K., Siwarski D., Skurla R., Klinman D., Mushinski J. F. (1990) *Proc Natl Acad Sci (USA)* 87, Kuschak, T. I., Paul, J. T., Wright, J. A., Mushinski, J. F., Mai, S. (1999) TTOL http://www.biomednet.com/db/uo.TO 1669.

Szeles, A., Falk, K. I., Imreh, S., Klein, G. (1999) *J. Virol* 73, 5064–5069.

Lawrence, J B, Singer, R H and Marselle, L M. (1989) *Cell* 57, 493–502. Evan, G. I., Lewis, G. K., Ramsay, G., Bishop. J. M. (1985) *Mol Cell. Biol*. 5, 3610–3616.

Juan, G., Traganos, F., James, W. M., Ray. J. M., Roberge, M., Sauve, D. M., Anderson, H., Darzynkiewicz, Z. (1998) *Cytometry* 32, 71–77.

Sambrook, J., Fritsch, E. F., Maniatis, T. Molecular Cloning. (1989) CSH Laboratory Press.

Mai, S., Hanley-Hyde, J., Coleman, A., Siwarski, D, Huppi, K. (1995) *Genome* 38, 780–785.

Juan, G., Traganos, F., Darzynkiewicz, Z. (1999) *Exp Cell Res*. 246, 2 12–220.

Wei, Y., Yu, L., Bowen, J., Gorovsky, M. A. and Allis, C. D. (1999) *Cell* 97, 99–109.

1. Gaubatz, J. W. (1990) *Mutat. Res*. 237, 27 1–292.

Iwasato, T., Shimizu, A., Honjo, T., Yamagishi, H. (1990) *Cell* 62, 143–149.

Matsuoka, M., Yoshida, K., Maeda, T., Usuda, S., Sakano, H. (1990) *Cell* 62, 35–142.

Brothman, A. R., Cram, L. S., Brothman, L. J. and Kraemer, P. M. (1987) *Cancer Genet Cytogenet* 26, Gaubatz, J. W. and Flores, S. C. (1990) *Mutat. Res*. 237, 29–36.

Cohen, S., Lavi, S. (1996) *Mol. Cell. Biol* 16, 2002–2014.

Cohen, S., Regev, A., Lavi, S. (1997) *Oncogene* 14, 977–985.

Regev, A., Cohen, S., Cohen, E., Bar-Am, I., Lavi, S. (1998) *Oncogene* 17, 3455–3461.

Wahl, G. M. (1989) The importance of circular DNA in mammalian gene amplification. *Cancer Res*. 49, Cox, D., Yuncken, C., Spriggs, A. I. (1965) *The Lancet* 58, 55.

Fegan, C. D., White, D. and Sweeney, M. (1995) *Br. I Haematol*. 90, 486–488.

Wullich, B., Muller, H. W., Fischer, U., Zhang, K. D., and Meese, E. (1993) *Eur J Cancer* 29A, 1991–

Chen, T. L. and Manuelidis, L. (1989) *Genomics* 4, 430–433.

Delinassios, J. G. and Talieri, M. J. (1983) *Experientia* 39, 1394–1395.

Rowland, P 3d, Pfeilsticker, J. and Hoffee, P A. (1985) *Arch Biochem Biophys*. 239, 396–403.

Wettergren, Y., Kullberg, A. and Levan, G. (1995) *Hereditas* 122, 125–134.

Stahl, F., Wettergren, Y. and Levan, G. (1992) *Mol Cell. Biol*. 12, 1179–1187.

Trent, J., Meltzer, P., Rosenblum, M., Harsh, G., Kinzler, K., Marshal, R., Feinberg, A., Vogelstein, B. (1986) *Proc. Natl. Acad. Sci. (USA)* 83, 470–473.

Martinsson, T., Stahl, F., Pollwein, P., Wenzel, A., Levan, A., Schwab, M., Levan, A. (1988) Oncogene 4, Von Hoff, D. D., Needham-Van Devanter, D. R., Yucel, Y., Windle, B. E., Wahl, G. M. (1988) *Proc. Natl. Acad. Sci. (USA)* 85, 4804–4908.

1. Von Hoff, D. D., McGill, J. R., Forseth, B. J., Davidson, K. K., Bradley, T. P., Van Devanter, D. R., wahl, G. M. (1992) *Proc. Natl. Acad. Sci. (USA)* 89, 8 165–8169.

Eckhardt, S. G., Dai A., Davidson, K. K., Forseth, B. J., Wahl, G. M., Von Hoff, D. D. (1994) *Proc. Natl. Acad. Sci. (USA)* 91, 6674–6678.

Shimizu, N., Nakamura, H., Kadota, T., Oda, T, Hirano, T. and Utiyama, H. (1994) *Cancer Res* 54, Coleman, A. E., Kovalchuk, A L., Janz, S., Palini, A., Ried, T. (1999) *Blood* 93, 4442–4444.

van der Plas, D. C., Hermans, A. B., Soekarman, D., Smit, E. M., de Klein, A., Smadja, N., Alimena, G., Goudsmit, R., Grosveld, R., Hagemejer, A. (1989) *Blood* 73, 103 8–1044.

Kurzrock, R., Kantarjian, H. M., Shtalrid, M., Gutterman, J. U., Talpaz, M. (1990) *Blood* 75, 445–452.

Costello, R., Lafage, M., Toiron, Y., Brunel, V., Sainty, D., Amoulet, C., Mozziconacci, M. J., Bouabdallah, R., Gastau, J. A., Maranichi, D. (1 995) *Br. J. Hematol* 90, 346–3 52.

Selleri, L., Milia, G., Luppo, M., Temperani, P., Zucchini, P., Tagliafico, E., Astusi, T., Sari, M., Donelli, A., Castoldi, G. L. (1990) *Hematol. Pathol*. 4, 67–77.

Janssen, J. W., Fonatsch, C., Ludwig, W. D., Bieder, H., Maurer, J., Bartram, C. R. (1992) *Leukemia* 6, 463–1992.

Estop, A. M., Sherer, C., Cieply, K., Groft, D., Burcoglu, A., Jhanwar, S., Thomas, J.(1 997) *Cancer Genet. Cytogenet*. 96, 174–176.

Uckun, F. M., Herman-Hatten, K., Crotty, M. L., Sensel, M. G., Sather, H. N., Tuel-Ajlgren, L., Sarquis, M. B., Bostrom, B., Nachman, J. B., Steinherz, P. G., Gaynon, P. S., Heerema, N. (1998) *Blood* 92, 10–82 1.

Klein, G. (1989) *Genes Chromosomes Cancer* 1, 3–8.

Klein, G. (1993) *Gene* 135,189–196.

Klein, G. (1995)*Int. J. Dev. Biol*. 39, 715–718.

What is claimed is:

1. A method of determining likelihood that a human patient will develop CLL comprising the step of detecting a presence of aberrant extrachromosomal gene amplification of cyclin D2, wherein aberrant extrachromosomal gene amplification of cyclin D2 indicates an increased likelihood that a human patient will develop CLL.

2. A method of determining likelihood that a human patient will develop cervical cancer comprising the step of detecting aberrant extrachromosomal or intrachromosomal gene amplification of a DHFR gene, wherein aberrant extrachromosomal or intrachromosomal gene amplification of the DHFR gene indicates an increased likelihood that a human patient will develop cervical cancer.

* * * * *